(12) United States Patent
Honstein et al.

(10) Patent No.: US 7,338,283 B2
(45) Date of Patent: Mar. 4, 2008

(54) DENTAL PROSTHESES MODELING SYSTEM WITH SYMMETRIC DOUBLE-WELL TRAYS SLIDABLY MOUNTABLE TO ARTICULATOR

(75) Inventors: Jerry P. Honstein, Corona, CA (US); Richard Barnes, Mission Viejo, CA (US); Anthony Siragusa, Anaheim, CA (US); Jason A. Phillips, Corona, CA (US); Kyung Rok Cho, Seoul (KR)

(73) Assignee: Dental Ventures of America Inc., Corona, CA (US)

( * ) Notice: Subject to any disclaimer, the term of this patent is extended or adjusted under 35 U.S.C. 154(b) by 404 days.

(21) Appl. No.: 10/743,673

(22) Filed: Dec. 22, 2003

(65) Prior Publication Data

US 2004/0197729 A1    Oct. 7, 2004

Related U.S. Application Data

(63) Continuation-in-part of application No. 10/461,968, filed on Jun. 12, 2003, now Pat. No. 6,913,462, which is a continuation-in-part of application No. 10/376,375, filed on Feb. 26, 2003, now Pat. No. 7,210,932.

(51) Int. Cl.
    *A61C 11/00* (2006.01)
(52) U.S. Cl. .............................. 433/57; 433/34; 433/60; 433/74
(58) Field of Classification Search .................. 433/60, 433/63, 65, 74, 34
    See application file for complete search history.

(56) References Cited

U.S. PATENT DOCUMENTS

| 5,913,681 | A | * | 6/1999 | Cho | ............................. | 433/60 |
| 6,019,601 | A | * | 2/2000 | Cho | ............................. | 443/60 |
| 2004/0013998 | A1 | * | 1/2004 | Jung et al. | ..................... | 433/57 |

* cited by examiner

*Primary Examiner*—Cris Rodriguez
*Assistant Examiner*—Candice C. Stokes
(74) *Attorney, Agent, or Firm*—William L. Chapin

(57) ABSTRACT

A dental prostheses modeling system includes a molding tray for molding the base of a quadrant or full-arch dental model cast which has a longitudinally disposed partition panel disposed generally between upper and lower surfaces of the tray that forms therewithin an upper well for receiving liquid die stone to mold the base of a dental impression model, and a lower well shaped symmetrically to the upper well for providing clearance for optional manipulating pins installable in the bases of selected die segments modeling individual dental prostheses severed from the hardened die stone base of the model. The partition panel includes peripheral flanges for supporting the base of the dental model, and an openable central portion for enabling a hardened dental model to be ejected from the tray, and for providing access for manipulating pins depending downwardly from die segments. A pair of slide receptacles for slidably receiving a modeling tray is removably attachable to upper and lower arms of a laboratory articulator, from which a pair of molding trays holding a pair of dental models can be slidably removed and attached to a disposable hinge mechanism to comprise a articulateable full-mouth model for a dentist and patient.

24 Claims, 63 Drawing Sheets

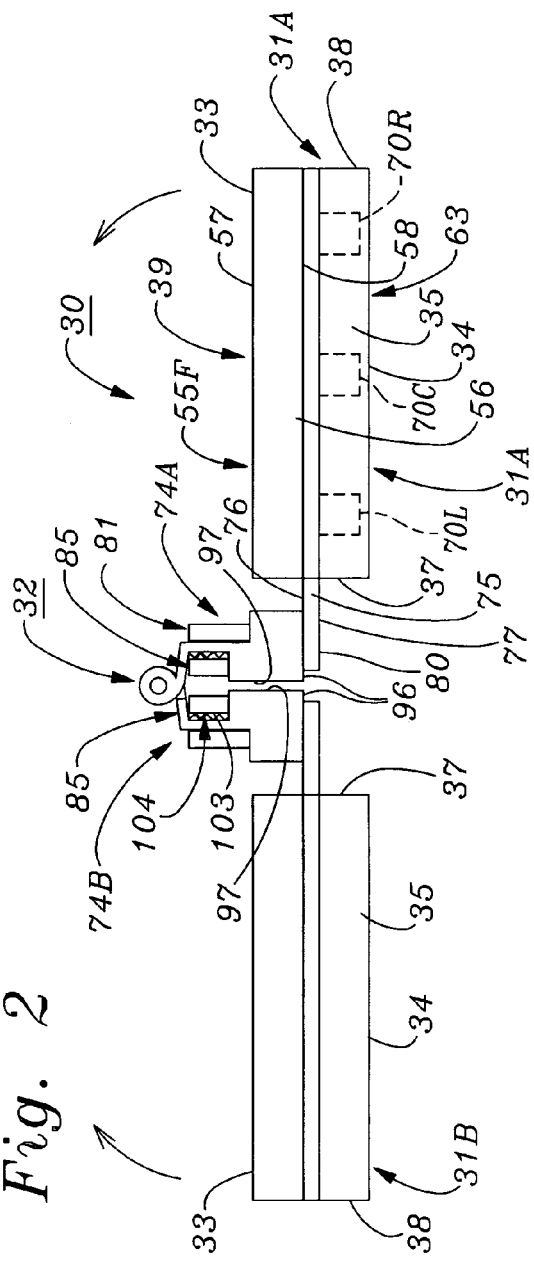
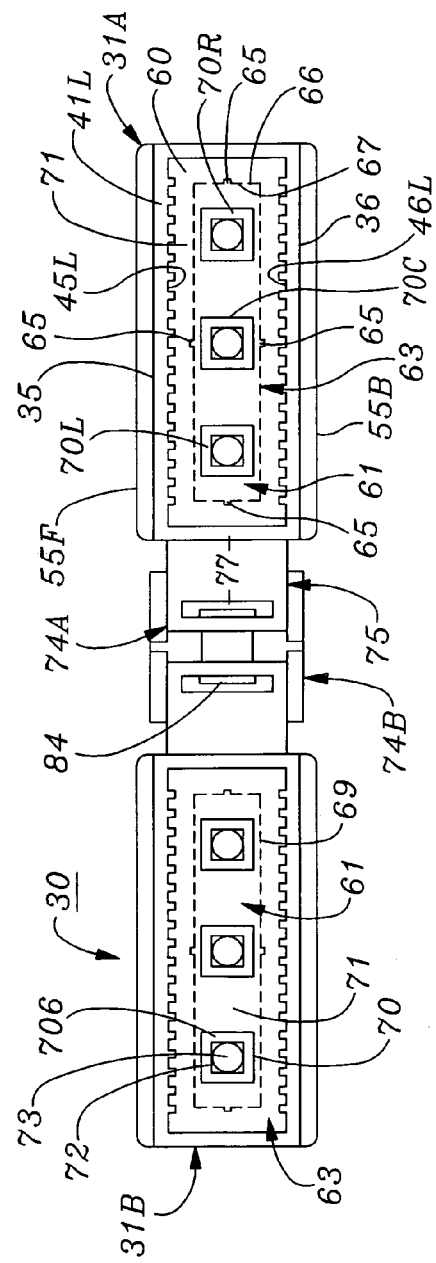

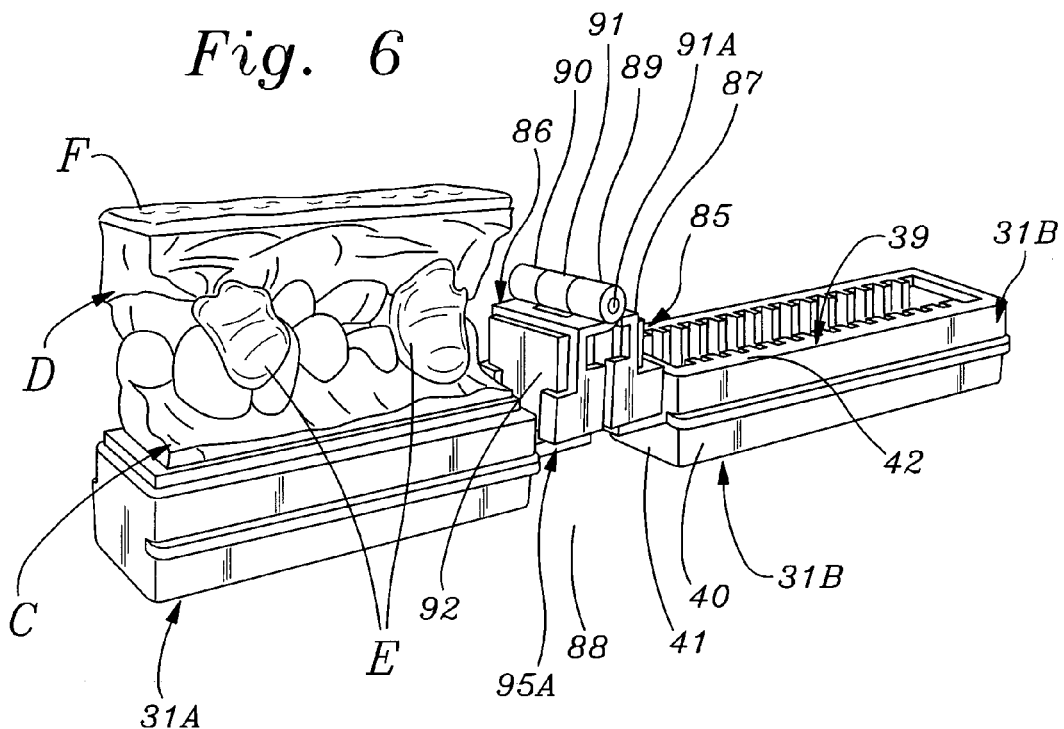
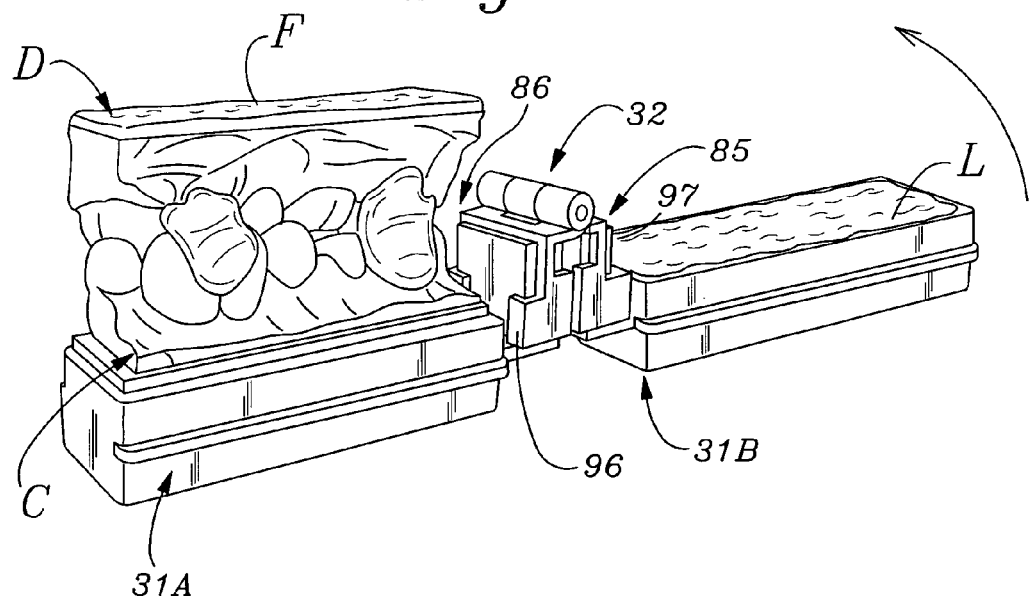

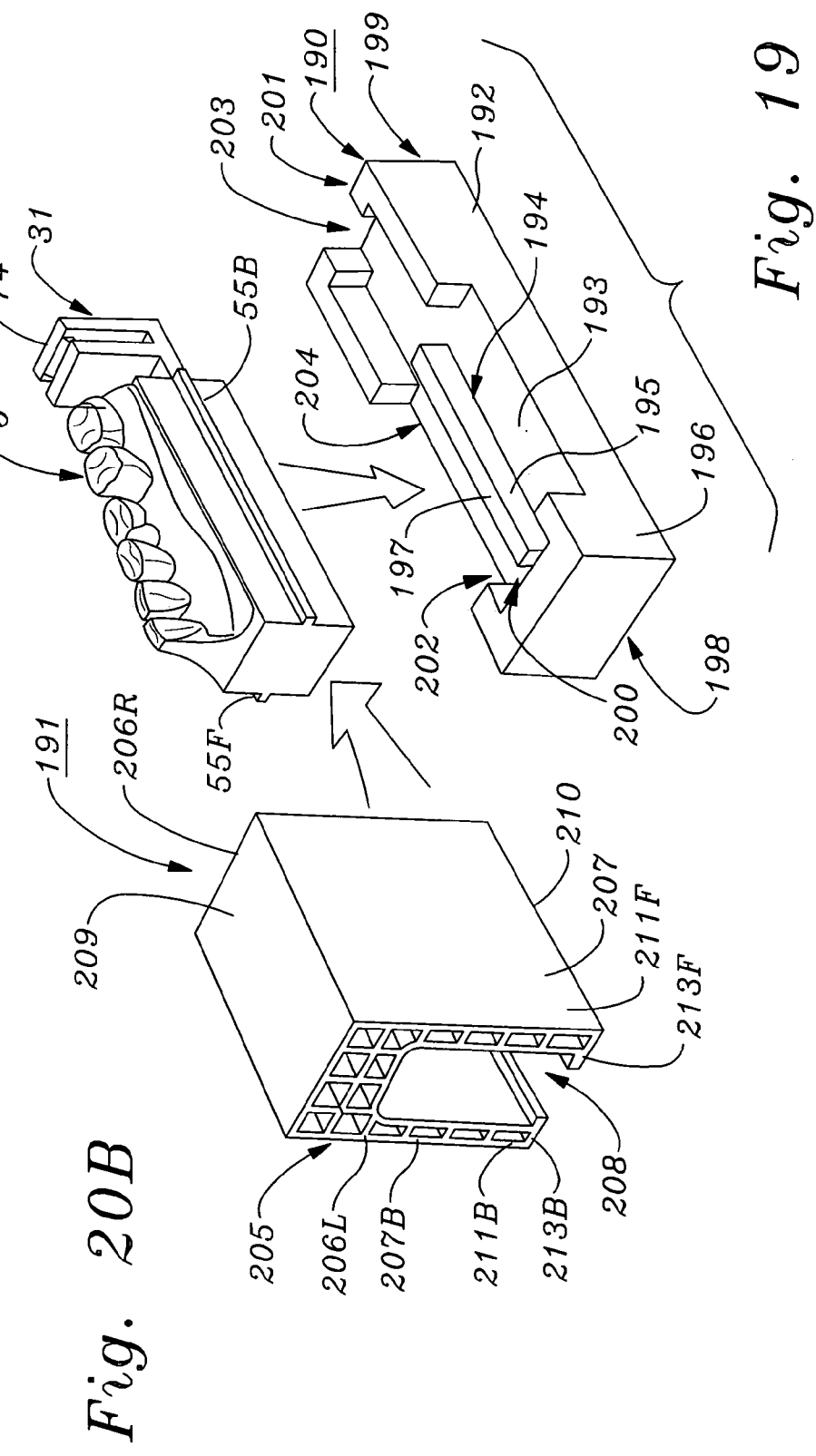

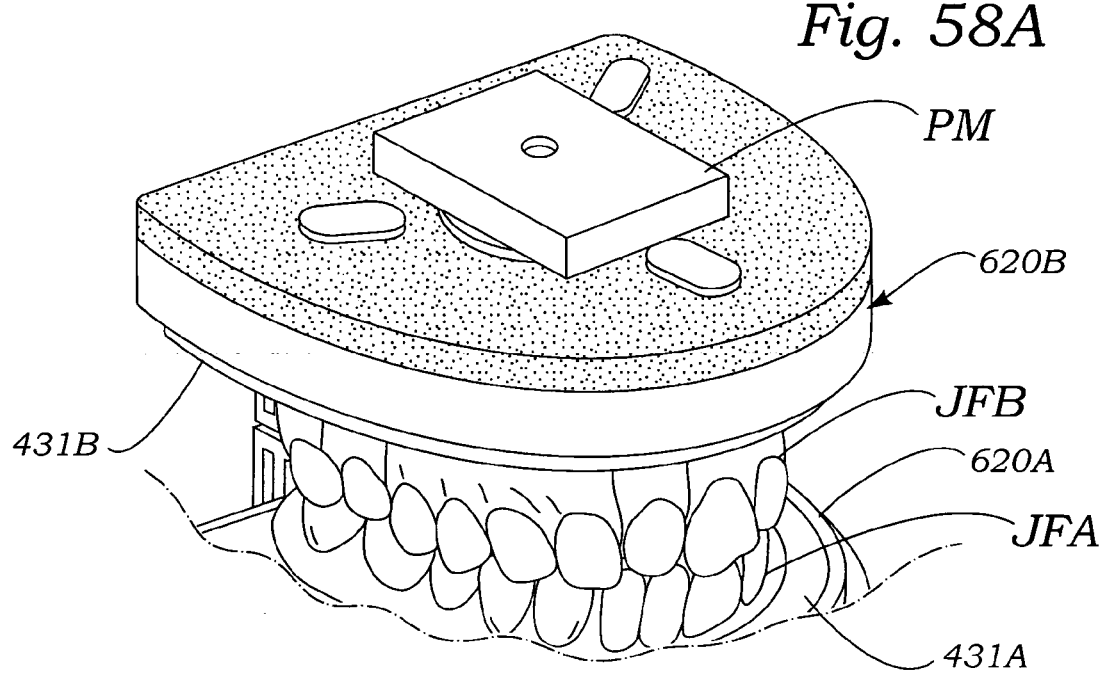

DENTAL PROSTHESES MODELING SYSTEM WITH SYMMETRIC DOUBLE-WELL TRAYS SLIDABLY MOUNTABLE TO ARTICULATOR

RELATED APPLICATION INFORMATION

The present application is a continuation-in-part of application Ser. No. 10/461,968, filed Jun. 12, 2003, now U.S. Pat. No. 6,913,462, which is in turn a continuation-in-part of application Ser. No. 10/376,375, filed Feb. 26, 2003 now U.S. Pat. No. 7,210,932.

BACKGROUND OF THE INVENTION

A. Field of the Invention

The present invention relates to articles and methods used in the fabrication of dental prostheses such as crowns and bridges made of various combinations of metal and ceramic materials and used to overlie or replace imperfect or missing teeth. More particularly, the invention relates to a system for use in fabricating crowns and bridges, the system including an apparatus and method for making from a mold or impression of a patient's teeth a dental model cast which is formed from solidified liquid die stone poured into the mold and an upper portion of a tray. The dental model cast is segmentable into die segments, each of which has both horizontally protruding ribs and grooves for releasably engagement with complementary-shaped grooves and ribs formed in a support tray. Individual die segments are optionally fitted with a pin which protrudes downwardly from the die segment, the pin facilitating gripping and manipulating of the die during various fabrication operations performed by a dental technician.

B. Description of Background Art

A dental procedure which is routinely used to restore function and aesthetic appearance to a person's mouth after a tooth has become broken, structurally degraded by disease or removed entirely, consists of capping or replacing the tooth with a prosthetic restoration, such as a crown or bridge. One form of dental prosthesis or artificial tooth replacement which is widely used consists of a cap or crown for a tooth that is made of a resin, molded ceramic material, a precious metal such as gold or an alloy thereof, or a layered combination of metals and resins or ceramic materials. Various combinations of the foregoing materials provide tooth restorations which possess requisite durability and aesthetic appearance, as well as sufficient hardness to be suitable for chewing foods. The process of fabricating tooth restorations has been in use for a substantially long time, and includes a well-defined sequence of steps, which are briefly summarized below.

According to a first step in existing methods of fabricating dental prostheses or artificial replacement teeth, a negative impression mold is made of a group of a patient's teeth, including missing, broken or decayed teeth which are to be repaired or replaced and teeth which are laterally adjacent to the defective teeth. Such impressions are typically made by positioning within the mouth of a patient, adjacent to teeth to be restored, a shallow curved tray which contains a polymer material such as alginate, elastomer, hydrocolloid or a polyether, which is capable of being indented by a tooth, and forming and retaining a stable impression of the tooth. The impression material is initially in the form of a putty, slurry or thick paste which rapidly solidifies at ambient room temperature and pressure. The tray is inserted into a patient's mouth positioned generally horizontally and in vertical alignment with a subject area of the teeth, and the patient bites down on the tray, or the tray is pressed into contact with the teeth, thus pressing the teeth into the viscous semi-liquid mold impression material held by the tray. After a few minutes, the mold impression material solidifies into a rubber-like elastomeric state which has formed therein precise negative impressions of teeth in a subject area of the patient's mouth.

Dental impression trays for use as described above are available in a variety of styles. One type tray has an arcuately curved plan-view shape which is similar to the curved arrangement of teeth in the jaw. The curved arc length of the tray approximates that of about one half an upper or lower jaw and hence is referred to as a quadrant tray. A flat, paddle-like handle protruding horizontally outwards from one end of the tray is usually provided, to facilitate inserting and removing the tray from a patient's mouth. A typical quadrant tray has on one side thereof a curved trough for receiving impression mold material, may be used to make impressions of upper or lower jaw quadrants and is referred to as a standard quadrant or single-bite tray.

Since an important structural feature of a dental prosthesis is proper registration and biting contact or occlusion between the prosthesis and teeth located in the opposing jaw, it is desirable to make an impression of occluding teeth in the opposing jaw in addition to the impression made of teeth that are to be restored. Therefore, it has been a trend in dentistry for the dental professional to simultaneously make impressions of teeth that are to be restored and occluding teeth in the opposing jaw. A convenient method for simultaneously making restorative and opposing impressions utilizes a tray which has a plan-view shape similar to that of a single-bite, standard quadrant impression tray, but which has upper and lower troughs for holding mold impression material in both upper and lower sides of the tray. Both the upper and lower troughs of these "double-bite" or "triple" trays are filled with viscous impression material and inserted into the patient's mouth between the upper and lower jaws in vertical alignment with teeth to be restored, whereupon the patient bites down on the tray, simultaneously forming impressions of upper and lower teeth.

After impressions of teeth have been made in the manner described above, and the mold impression material solidified, the tray holding solidified mold impression material containing negative impressions of a patient's teeth is removed. The mold, typically referred to as an "impression," is then used to make positive replicas of teeth by pouring a semi-liquid molding material such as plaster of Paris, or die stone, into the depressions formed in the impression, which are accurate negative replicas of the teeth. After the die stone has solidified into a hard stone-like casting, or cast, the cast is removed from the impression, a task which is facilitated by the fact that the impression material is elastomeric, enabling it to be readily peeled away from the die. The casting is then used to fabricate one or more tooth restorations or prostheses in the following manner.

A master cast, i.e., a cast which includes replicas of teeth which are to be restored, is partitioned into one or more individual segments and/or dies, each consisting of a replica of a tooth which is to be replaced by or fitted with a dental prosthesis. Partitioning of a master cast into die segments is typically accomplished by making parallel vertical saw cuts through the master cast. The individual die segment or segments are then used as three-dimensional models or templates for fabricating crowns or bridges. In general, the exterior surfaces of the prosthesis cannot simply replicate those of the die segments. This is because the occlusal surface of the prosthetic tooth restoration, and to a lesser extent, lateral surfaces of the restoration, may require contouring which is different from that of the die segment. For example, the process of fabricating crowns for diseased or damaged teeth entails grinding decayed or broken outer portions of the tooth down until a stump of healthy dentin or enamel remains, a procedure referred to as "prepping" the tooth. Obviously, a crown which is fabricated to fit onto a stump must have a substantially different, tooth-like shape rather than a stump-like shape.

From the foregoing discussion, it can be appreciated that the fabrication of dental prosthesis models from die segments is a labor-intensive task requiring the skills of a prosthodontist or skilled, experienced, dental lab technician. Fabrication of prosthetic dental models typically requires that die segments be contoured by applying a workable material to exterior portions of the die segment, and sculpting the material. The die segment is then replaced into the space in the master cast from which it has been removed, and proper occlusion of the sculpted prosthetic model confirmed by bringing model teeth replicated in the opposing cast into bite-like contacting registration with the occlusal surfaces of the prosthetic model and adjacent teeth replicas of the master cast. This registration check generally must be repeated several times, to ensure proper sculpting of the occlusal surface of the die segment which serves as a model for fabricating a dental prosthesis. Moreover, it is essential that the biting contact or occlusion between the teeth replicated by the master cast and opposing cast precisely duplicate occlusion of the patient's teeth. Therefore, the master cast and opposing cast must be precisely and repetitively pivotably contacted against one another in a motion which simulates the opening and closing of a patient's jaws. Upon satisfactory completion of sculpting of lateral and occlusal surfaces of die segments, the die segment is used as a mold pattern for casting a metal, ceramic, or metal-ceramic composite dental prosthesis.

One type of device which is used to pivotably register master and opposing dental models or arches is referred as an articulator. For example, Cho, U.S. Pat. No. 6,019,601, Tray Modeling System With Articulator Assembly And Ejection Mechanism For Producing A Dental Model, discloses a pair of trays which are removably and pivotably joined together by detachable hinge members. Each tray has formed upon an upper surface thereof a rectangularly-shaped, trough-like depression, the longest inner facing side walls of the trough having formed therein alternating vertically disposed ribs and grooves. The device is used by pouring a thick paste of liquid die stone slurry into both a dental impression and the tray, and inverting the impression to enable the liquid die stone slurries in the impression and tray to commingle. When the die stone has solidified, the impression is removed from the cast, and the cast removed from the tray by punching through a frangible base panel in the tray, forcing the cast vertically outwards from the trough. The cast is then sawed into segments, which are returnable to precisely repeatable locations within the trough because of the interlocking ribs and grooves formed in the vertical walls of the cast by die stone solidifying in the grooves and ribs, respectively, of the trough side walls, during hardening of the die stone. In the same manner, an opposing cast is made in the other tray, and the trays pivoted towards one another on the hinge pins to precisely and repeatedly bring the occlusal surfaces of the opposing cast and master cast into occlusal registration.

The Cho modeling system and articulator provide a convenient means for preparing and articulating dental models. However, some dental technicians prefer working with die segments which have an elongated cylindrical pin protruding from the base of the die segment. In modeling systems using pinned die segments, the pins are insertably received in holes provided in the base of a tray, and are used to reproducibly position or relate individual die segments to adjacent portions of the master cast. Moreover, a pin protruding from a die segment provides a convenient handle which enables the dental technician to hold a die segment while working on it, including rotating the die segment a full 360 degrees by twisting the die segment pin between the thumb and forefinger of the dental technician. Thus, Sim, U.S. Pat. No. 6,402,513, Dental Model Articulator, discloses a dental model articulator which has pinned die segments. The dental model articulator disclosed in Sim utilizes a top insert which has front and rear upwardly protruding ridges that have grooved upper surfaces. The insert is detachably supported on a lower frame. To pour a master cast of a dental impression, a middle frame must be fastened to a lower frame and around the top insert by engaging slots on left and right sides of the middle frame with retentive latches which protrude upwards from the lower frame, on left and right sides of an upper opening in the lower frame which holds the top insert. According to the disclosure of Sim, the middle frame is discarded after completion of a second pour of liquid die stone through a bottom opening of lower frame, to form a perforated matrix for receipt of pins installed in the base of the first impression casting. The grooved insert is discarded after the first pour.

In U.S. patent application Ser. No. 10/376,325, filed Feb. 26, 2003, three of the present inventors disclosed an improved dental modeling system which includes a modeling tray that molds die segment bases which each have short ribs and grooves that enable removal of the die segments from a dental model cast in the tray, and re-insertion of the segments into the tray in precise re-registration with adjacent portions of the cast. That capability is provided by a combination of alignment forces between complementary-shaped grooves and ribs in vertical walls of a shallow trough-like depression in the upper part of a modeling tray, in combination with alignment forces provided by a tapered pin which protrudes downwardly from the die segment and which is received in a pin bore formed in a hardened die stone base matrix cast located in a relatively deep, lower concave opening of the tray. Also, in U.S. patent application Ser. No. 10/461,968, filed Jun. 12, 2003, the aforementioned three inventors disclosed a further improved dental modeling system which employed re-usable modeling trays.

Although the above-disclosed systems function admirably in accomplishing their intended purposes, there are occasions in which it would be desirable to provide a dental prostheses modeling system which does not require a second pour of liquid die stone to form a stone base matrix, in addition to the first pour required for molding the dental cast itself, while still enabling die segments to be removed and re-inserted into precise, stable relationship with adjacent portions of a dental impression cast, without requiring that die segments be provided with pins. Also, it would be desirable to provide a dental modeling system in which selected die segments are optionally fitted with a pin which depends downwardly from a die segment, to facilitate manipulation of the segment by a technician during the manufacture of a dental restoration. It would also be desirable to provide a dental modeling system for full arch casts in addition to quadrant casts, with the aforementioned capabilities. Morever, it would be desirable to provide a means for attaching pairs of full arch casts in an adjustably articulatable fashion to a rugged, dimensionally stable three-dimensional clinical dental articulator of the type used in dental labs, in the usual manner of using molded plaster or other conventional means to attach the casts to upper and lower articulator arms, yet enabling the full arch casts and/or restorations made therefrom to be easily removed from the lab articulator, returned to the dentist, and re-attached to a low cost, disposable display or presentation articulator hinge mechanism for viewing by the dentist and his or her patient. The present invention was conceived of to fulfill the foregoing needs.

OBJECTS OF THE INVENTION

An object of the present invention is to provide a dental prostheses modeling system for fabricating models of human teeth, in which individual die segments of the models may optionally be provided with a downwardly depending manipulating pin for facilitating handling the die segment in the process of making a dental restoration using the model.

Another object of the invention is to provide a dental modeling system which includes a tray having in an upper part thereof an upper well which has an openable base panel or wall for receiving a semi-liquid modeling material or casting material such as plaster of Paris or die stone, the well having relatively high opposed vertical walls, the inner facing surfaces of the walls having formed therein alternating vertically disposed ribs and grooves for forming a dental model casting, a base portion of which casting has in outer walls thereof alternating vertically disposed grooves and ribs shaped complementarily to the ribs and grooves, respectively, in the inner facing tray wall surfaces, interlocking of the casting ribs and grooves with the tray grooves and ribs enabling vertically upward removal of the casting and/or die segment portions thereof from the tray, and vertically downward movement of the casting or die segments thereof into precisely relocatable positions within the tray, the base of the upper well overlying a lower well of sufficient depth to position lower surfaces of pins optionally installed in die segments and protruding perpendicularly downwards therefrom above the lower surface of the tray.

Another object of the invention is to provide a dental prostheses modeling system tray in which the openable base wall thereof comprises one or more elongated panels located generally midway between and parallel to upper and lower faces of the tray, the panels being joined by frangible members at outer edges thereof to peripheral base flange walls, whereby the frangible members may be broken to enable a panel to be removed and leave in its place an elongated, panel-shaped aperture through the flange walls, the aperture joining symmetric, approximately equal depth upper and lower wells of the tray.

Another object of the invention is to provide a dental prostheses modeling system tray having between lower and upper edge walls thereof an elongated removable panel which serves as a base wall for a trough-shaped pouring well in an upper half of the tray, the panel being provided with an elongated thin rib which protrudes upwardly from an upper surface of the panel, the rib being located generally midway between longitudinally disposed sides of the tray comprising an inner, lingual and an outer, labial side, whereby an elongated longitudinally disposed groove is formed in the base of a dental model cast molded in the tray, the groove serving as a guide or pilot groove for guiding insertion into the cast base of a drill bit used to drill a hole for inserting a manipulating pin centered in a selected portion of the cast which is segmented into a die.

Another object of the invention is to provide a re-usable symmetric double-well dental modeling tray which includes a resilient insert member of the proper size and shape to fit resiliently within an aperture which joins upper and lower wells of the tray, the resilient insert member having an upper surface which fits substantially flush with peripheral flange walls which surround the aperture and thereby form therewith a temporary base wall impervious to liquid die stone, the insert being removable from the tray after a dental base cast formed therein has hardened, and the cast removable from the tray to thereby enable re-use of the tray and insert for fabricating other dental model castings.

Another object of the invention is to provide knock-out tools and templates for efficiently removing dental castings which have solidified in quadrant and full arch modeling trays.

Another object of the invention is to provide an articulator slide receptacle for slidably and releasably receiving and holding in place a full arch dental model cast retained in a modeling tray, the articulator slide receptacle being fixedly securable by plaster of Paris or the like to an upper or lower arm of a three dimensional laboratory or clinical articulator, the tray being slidably removable from the articulator slide to enable a pair of related, full arch dental models to be slidably removed from a pair of slide receptacles detached from the lab articulator, and the trays and models transferred from a dental lab to a dentist's office and re-attached to a lighter duty, presentation/demonstration articulator for viewing by a dentist and/or patient.

Various other objects and advantages of the present invention, and its most novel features, will become apparent to those skilled in the art by perusing the accompanying specification, drawings and claims.

It is to be understood that although the invention disclosed herein is fully capable of achieving the objects and providing the advantages described, the characteristics of the invention described herein are merely illustrative of the preferred embodiments. Accordingly, we do not intend that the scope of our exclusive rights and privileges in the invention be limited to details of the embodiments described. We do intend that equivalents, adaptations and modifications of the invention reasonably indexable from the description contained herein be included within the scope of the invention as defined by the appended claims.

SUMMARY OF THE INVENTION

Briefly stated, the present invention comprehends a dental prostheses modeling system which includes an apparatus and method for fabricating models of human teeth; the models are subsequently used in the fabrication of dental prostheses such as crowns and bridges made of various combinations of metal and ceramic materials and used to overlie or replace imperfect or missing teeth. According to the invention, methods and apparatus are provided for making casts of dental impressions, which are segmentable into die segments for use as models in fabricating individual dental prostheses.

According to one aspect of the invention, a modeling or molding tray for molding the base of a quadrant or full arch dental model cast has a longitudinally elongated rectangular or arch-shaped plan view, and has formed in opposed inner vertically disposed longitudinal perimeter walls of a relatively deep well formed in the upper side of the tray, horizontally outwardly protruding protrusions alternating with horizontally inwardly protruding depressions. Complementary-shaped depressions and protrusions are formed in opposed inner facing walls of the base of a dental model cast formed when liquid die stone is poured into the upper well of the tray, and allowed to solidify.

According to the invention, the tray includes at least one horizontally disposed, break-away base plate or panel which is located approximately midway between and parallel to upper and lower surfaces of the tray. The break-away base plate is joined at outer peripheral edges thereof by frangible members to flanges which protrude radially inwardly from inner facing surfaces of the vertical well walls, the flanges having upper and lower surfaces generally coplanar with upper and lower surfaces of the break-away panel. The break-away base panel serves as a support base for the lower or base portion of a dental model cast formed by solidification of liquid die stone poured within the well in the upper portion of tray. Semi-liquid die stone is poured to overflowing into a dental impression mold containing imprints of a patient's teeth and also poured to overflowing into the upper opening of the upper well in the upper portion of the tray. The filled impression mold is then inverted, positioned over the tray, and pressed down into semi-liquid die stone in the tray. The liquid die stone in the impression and tray co-mingle and cohere, eventually hardening to form a unitary cast which consists of a lower, base portion molded within the tray and having ribs and grooves molded into opposite vertical walls thereof, and an upper portion which protrudes upwardly from the base and which replicates teeth that imprinted the impression mold.

After a dental mode cast has hardened in a tray, an upwardly directed force is exerted on the underside of the break-away base plate, breaking the frangible members joining the base plate to the well walls and ejecting the hardened cast upwardly out of the tray. The hardened dental model cast if then segmented by a saw into individual die segments or "dies" which are cast replicas of selected teeth which are to serve as models for fabricating individual dental prostheses. Optionally, individual die segments are individually fitted with a manipulating pin which protrudes downwardly from the base of a die segment and which provides a convenient appendage for a laboratory technician to grasp during the course of fabricating a dental prostheses from a die segment. In this case, the hardened cast die segments are inverted, and blind bores are drilled into the lower surface of individual die segments, the bores being positioned in vertical alignment with cast replicas of selected teeth which are to serve as models for fabricating individual dental prostheses. A cylindrically-shaped manipulating pin is then inserted into each bore and secured in the bore with an adhesive such as glue. The cast is then flipped over to an upright position, with pins protruding perpendicularly downwards from the base of the cast, and reinserted into the upper opening of the tray. Ribs and grooves molded into opposite longitudinally disposed vertical sides of the cast base vertically slidably engage with the relatively long, complementary-shaped grooves and ribs in the inner side walls of the tray which formed the ribs and grooves of the cast. This arrangement ensures that when the cast is reinserted into the tray, the cast is returned to a previously predetermined lateral index position within the tray. Moreover, the cast is relocated at a previously predetermined vertical position within the tray because of abutting contact between the lower surface of the hardened cast base of the cast and upper surfaces of the base panel flanges.

A dental modeling the tray according to the present invention has formed in a lower portion thereof a relatively deep upwardly concave lower cavity or well located below the break-away base panel which has a shape and size similar to and preferably symmetric with that of the upper well in the upper portion of the tray. The lower well is of sufficient depth to position lower surfaces of pins optionally installed in die segments above the lower surface of the tray, and therefore, above a surface used to support the tray. The cast is typically segmented into individual die segments for modeling individual dental prostheses, by making one or more pairs of saw cuts vertically through the cast, adjacent to a selected die segment. Individual die segments are once again reinserted into the upper opening of the tray, to thereby re-assemble a complete cast comprised of individual die segments and adjacent portions of the cast within the tray. Precise placement of die segments within the tray is facilitated by alignment of mating ribs and grooves in the inner sides of the tray and the outer sides of the die segments. The aligning forces provided by insertion of ribs of the casting base into tray grooves enables individual die segments to be quickly and easily removed from the tray, subjected to various prosthesis modeling operations, and returned to a precisely repeatable, indexed positions within the cast, as many times as is required.

A preferred embodiment of a dental prostheses modeling system according to the present invention includes an opposing tray for making a casting of a dental impression which was made of teeth opposed to those which are to be fitted with or replaced by prostheses. The preferred embodiment also includes components which hingedly couple a master tray holding a master impression cast to an opposing tray holding an opposing impression cast and forming therewith an articulator mechanism which enables the occlusal surfaces of the master and opposing casts to be brought into pivotable contact with one another, thereby simulating closure of a patient's jaws and proper occlusion of the teeth modeled in the two casts. If dental prostheses are required only for one jaw, the cast made of the opposing jaw does not have to have removable die segments. Therefore, the opposing tray need not be provided with the previously described structural features which enable die segments to be removed and replaced within the tray. However, to minimize the number of different type parts required by the present system, the opposing tray may be constructed identically to the master tray, even though the break-away base panel and indexing grooves and ribs are not required for the opposing cast, since it may remain permanently affixed to the tray.

In any event, both the master and opposing trays, which may be of identical construction, are provided with a hinge coupler bracket which extends longitudinally outwards from a short end of each tray. The bracket has the shape of a bifurcated L-bracket including a flat longitudinally disposed horizontal floor plate which extends perpendicularly outwards from a short vertical end wall of the tray. The floor plate of the bracket has a flat horizontally disposed upper surface which is recessed slightly below the upper surface of the perimeter edge wall of the tray. A pair of rectangularly-shaped connector plates protrudes upwardly from an outer longitudinal end portion of the floor plate. The outer connector plates from a pair of trays are releasably joined together by a hinge coupler member that has an upper piano-type hinge, and opposed horizontal upper support plates located on opposite sides of a horizontally disposed hinge pin. The hinge coupler has protruding perpendicularly downwardly from outer ends of each support plate a vertical connector plate which has at the lower end thereof a pair of inwardly facing C-shaped channel members which have therein opposed vertically disposed C-shaped channels adapted to insertably receive an outer upstanding end plate of a tray coupler. This construction enables the outer slotted ends of the hinge coupler to be readily slipped removably over the upstanding connector flange plates of a longitudinally aligned pair of trays, i.e., a master tray and an opposing tray, and thereby hingedly coupling the two trays together so that upper surfaces of the trays which protrude horizontally inwardly from inner vertical wall surfaces of the tray trough, may be pivoted towards and away from one another to simulate closure and opening of a patient's jaws.

According to another aspect of the present invention a dental prostheses modeling system utilizes a re-usable modeling or molding tray for fabricating cast dental models. A re-usable molding tray according to the present invention is substantially similar in construction to the molding tray described above, but does not have a break-away center panel located between upper and lower surfaces of the tray. The re-usable molding tray has instead of a break-away center panel a rectangular ring-shaped base wall formed of flanges and has through its thickness dimension a rectangularly-shaped aperture. Thus constructed, the re-usable tray according to the present invention can be fabricated as an injection molded part, or by removing the break-away center panel from a tray constructed as described above.

A dental modeling system with re-usable tray according to the present invention also includes a re-usable resilient insert which has a rectangular plate-shaped base and a rectangular boss lug which protrudes upwardly from the base, the lug being adapted to be resiliently inserted upwardly through the entrance opening to the lower well in the tray into the aperture through the base wall of the tray.

The lug has a flat upper surface located at a height above the upper surface of the insert base plate such that when the lower edge wall of the tray is seated on the upper surface of the insert base plate, the upper surface of the lug is parallel to the base plate and is substantially flush with the upper surface of the rectangular ring-shaped base wall of the tray. The lug fits within the tray aperture in a resilient liquid-tight seal, thus forming with adjacent inner side walls of the upper portion of the tray a rectangular box-shaped upper well which serves as a mold for receiving liquid die stone to form the base of a dental model cast. After liquid die stone has hardened to form a cast, the insert is withdrawn from the tray aperture and the lower well in the tray. The tray and cast are then processed by any of the various methods discussed above for the tray provided with a break-away base panel, to fabricate individual, optionally pinned die segments comprising individual dental prostheses models which are repeatedly removable and returnable to precisely pre-determined index positions within remaining portions of a cast held in the tray.

According to another aspect of the invention, the break-away panel or insert is provided with a thin, longitudinally elongated rib which protrudes upwardly from the upper surface of the break-away panel or insert. The rib is preferably disposed midway between inner, or lingual and outer, or labial sides of the panel or insert, and is disposed longitudinally nearly the full arch length of the tray. Thus, dental model casts made in trays in which the break-away panel or insert which serves as the base of a well or trough for receiving liquid die stone is provided with a rib have formed in the lower surface of the base of the cast a longitudinally disposed groove. The groove protrudes upwardly into the base of a dental model cast from the lower surface of the base, and has a cross sectional shape complementary to that of the rib, e.g., rectangular. Also, the groove formed in the base of a dental model cast is longitudinally elongated, is located generally midway between the inner and outer surfaces of the dental model cast, and extends nearly full length of the cast, i.e., nearly to opposite transverse sides of the cast. Preferably, the rib and groove thickness approximates the diameter of the reduced diameter knurled end of a manipulating pin which is to be inserted into a base portion of a dental model cast severed from the cast to comprise an individual die segment for modeling a dental prosthesis. Thus formed, the groove serves as a pilot or starter indentation for insertably receiving and guiding into the base of a cast the point of a drill bit used to drill a pin bore into a selected die segment portion of the cast. Therefore, pin bores may be easily drilled into the base of a dental model cast at selected longitudinal locations of the cast, without requiring a drilling fixture, by visually aligning the drill bit approximately midway between transversely disposed sides of a die segment, inserting the tip of the bit into the pilot groove, and drilling the pin bore. Pin bores formed using the pilot groove in the foregoing manner are thus centered both laterally and longitudinally with respect to sides of a dental prosthesis die segment.

According to another aspect of the present invention, a novel slide receptacle fixture and method for use are provided which enable a pair of related, i.e., upper and lower, full-arch dental models to be affixed to the upper and lower arms of a three-dimensional laboratory articulator with the requisite stability and dimensional placement accuracy required for precision dental lab procedures to be performed in the fabrication of dental restorations, while providing a capability for replaceably removing the full-arch from the dental model laboratory articulator upon completion of dental lab tasks, whereupon the models may be returned to the dentist and re-attached to a less expensive, lighter duty articulator for viewing by a dentist and his or her patient. According to this aspect of the invention, a full-arch dental model does not have to be removed from a modeling tray in which it is formed, or be directly attached by plaster of Paris or the like to upper and lower arms of a laboratory articulator, as is done in the prior art. Instead, according to the present invention, a semi-elliptically-shaped heel-like articulator slide receptacle is provided, the receptacle having a flat base and an upstanding elliptically curved rail or flange wall which has a radially inwardly curved lip or flange that overlies and is parallel to the base plate, and forms therewith an arcuately curved channel which is adapted to receive a similarly-shaped, horizontally disposed abutment flange which protrudes outwardly from the outer curved front vertical surface of a full-arch dental modeling tray according to the present invention. In use, a full-arch dental tray containing a cast dental model is slid forward into the articulator slide receptacle channel, where it is retained in an interference fit. The articulator slide receptacle includes fastening means on the side of its base opposite to that of the rail which enable the receptacle to be securely fastened to an upper or lower laboratory articulator arm. In a preferred embodiment, the fastening means including a disk-shaped pot magnet embedded in a well formed in the lower wall surface of the articulator slide base plate, with the upper surface of the magnet flush with the adjacent base plate wall surface, and a similarly shaped magnet embedded in a cast plaster plate attached to an articulator arm.

BRIEF DESCRIPTION OF THE DRAWINGS

FIG. 2 is a side elevation view of a pair of trays of the type shown in FIG. 1, the trays being joined by a hinge coupler.

FIG. 3 is a lower plan view of the trays and coupler of FIG. 2.

FIG. 6 is a perspective view showing a third step of making a dental model cast in which a completed master dental model casting residing in a first tray in which it was cast, an opposing cast positioned above the master cast with occlusal surfaces of upper and lower replica teeth in the opposing and master casts temporarily adhered together in proper occlusal registration by blobs of wax, and the first, master tray coupled to a second, opposing tray by a hinge coupler.

FIG. 7 is a view similar to that of FIG. 6, but showing a fourth step in which semi-liquid die stone is applied to both the upper surface of the opposing cast, and the upper surface of the opposing tray.

FIG. 19 is a perspective view of a knock-out template for removing a break-away base panel of the tray shown in FIGS. 1-3.

FIG. 20B is a side perspective view of the tool of FIG. 20A.

FIGS. 50A-50L illustrate a prior art 3-D laboratory or clinical dental articulator, and a prior art method of attaching full-arch dental model casts to an articulator, in which:

FIG. 50A shows a pair of full-arch dental models casts in a prior art trays and temporarily adhered together by wax in proper occlusion.

FIG. 50B is an upper perspective view of a 3-D articulator mechanism and plastic mounting plate adapted to be fastened to the upper or lower surface, respectively, of a support base lower arm or upper arm of the articulator mechanism.

FIG. 50C is a lower plan view of the plastic mounting plate of FIG. 50B.

FIG. 50D is an upper plan view of the plastic mounting plate of FIG. 50C.

FIG. 50E is a lower perspective view of the plastic mounting plate of FIG. 50D, showing semi-liquid die stone adhered to the upper surface of the mounting plate.

FIG. 50F is a lower perspective view of the full-arch dental model of FIG. 50A, showing a ferromagnetic or magnetized disk being affixed to a lower surface of a prior art molding tray holding an inverted lower full-arch dental model.

FIG. 50G is a view similar to that of FIG. 50F, showing a pot magnet magnetically attached to the lower surface of the magnetic disk of FIG. 50F.

FIG. 50H is a view similar to that of FIG. 50G, showing a silicone pin-protection dam being adhered to a lower surface of the molding tray.

FIG. 50J is a view showing the mounting base plate of FIGS. 50C and 50D attached by screw to the lower arch support arm of a 3-D articulator, the lower arch of FIG. 50H having had semi-liquid die stone smeared onto the lower surface of the lower arch support tray, pressed into the semi-liquid die stone on the upper surface of the plastic mounting base plate, and allowed to harden.

FIG. 50K is a perspective view showing semi-liquid die stone applied to the upper surface of the upper arch support tray and to the lower surface of an upper mounting plate secured to an upper pivotable arm of the articulator preparatory to pivoting the arm downwardly to press the two semi-liquid, die-stone coated surfaces together to cohere and harden.

FIG. 50L is a perspective view showing a finished pair of upper and lower full-arch dental model casts properly occluded and removably attached to upper and lower arms of the 3-D articulator.

FIG. 58A is a perspective view showing the lower slide receptacle of FIG. 57, which has had a magnet magnetically attached to a magnetic disk in the center of the lower surface of the lower slide receptacle.

DESCRIPTION OF THE PREFERRED EMBODIMENTS

A. Drawing Description Summary

Figure 20A:
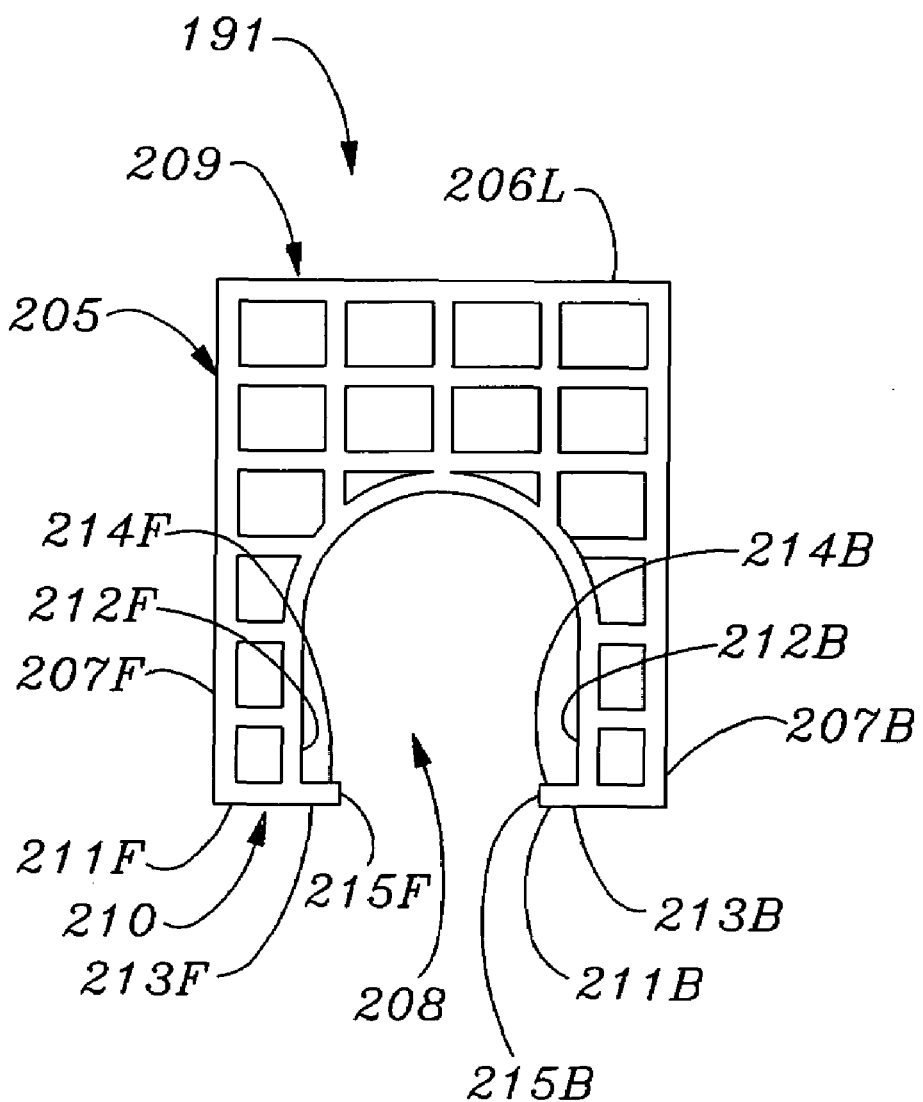
FIG. 20A is a side elevation view of a knock-out tool useable with the template of FIG. 18 to remove a break-away base panel from the tray of FIGS. 1-3.
Figure 21:
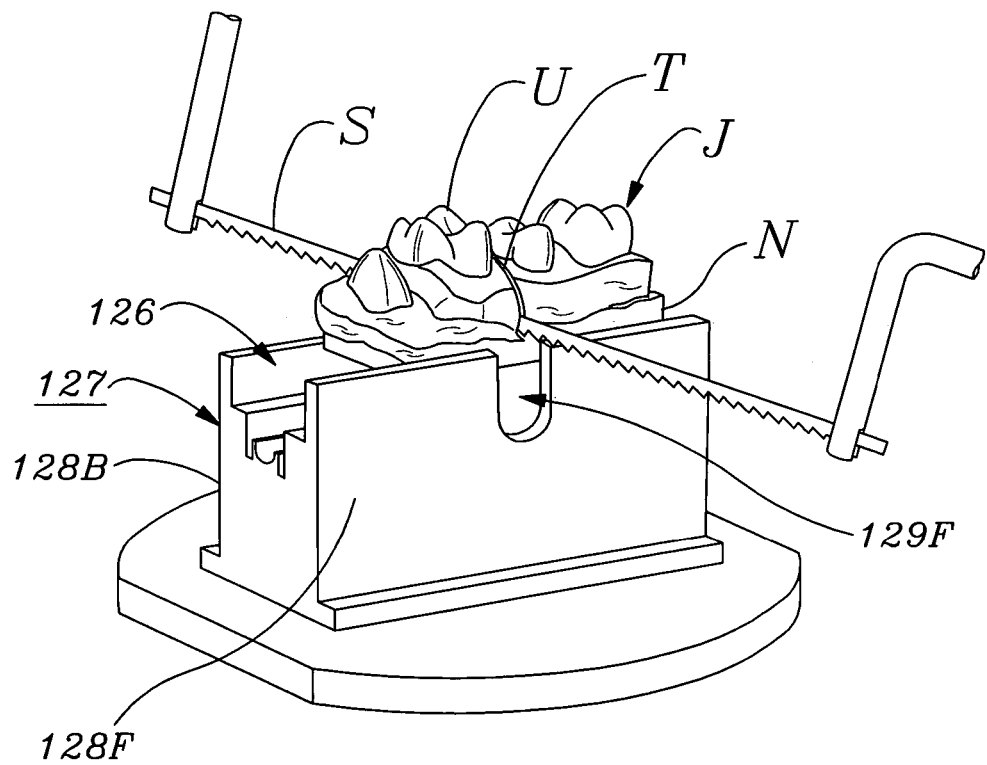
FIG. 21 is a perspective view of a sawing stand for use in segmenting a dental model cast according to a method of the present invention.
Figure 22:
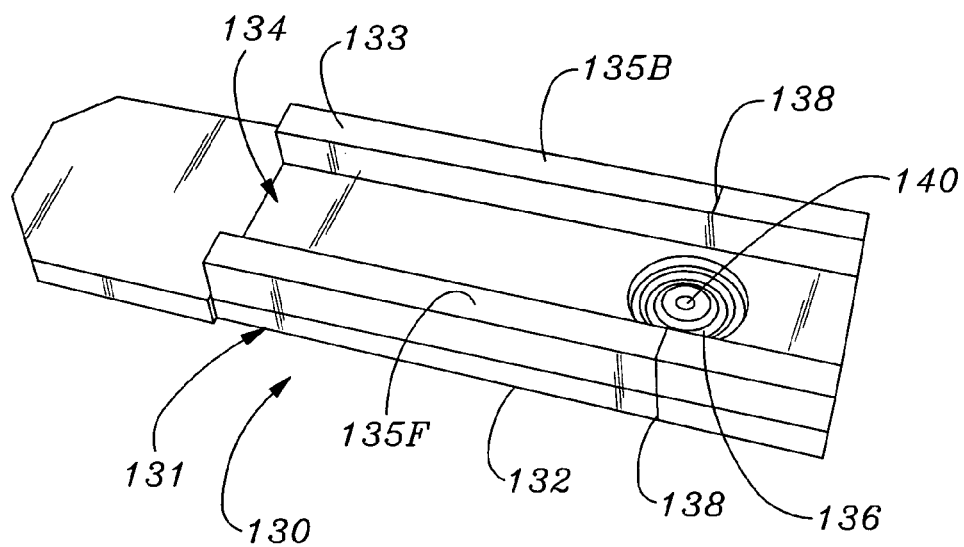
FIG. 22 is a perspective view of a drilling alignment fixture comprising a component for use in an alternative embodiment of a pin tray dental prostheses modeling system according to the present invention.

FIGS. 1-3 and 19-21 illustrate components of a basic embodiment of dental prostheses modeling system with symmetric double well quadrant modeling trays according to the present invention, while FIG. 22 illustrates a drilling alignment fixture for use in an alternate embodiment of the system.

FIGS. 4-8 illustrate steps in a method of making a dental model cast from a single quadrant impression for use in fabricating dental prostheses, according to a basic embodiment of the invention.

Figure 9:
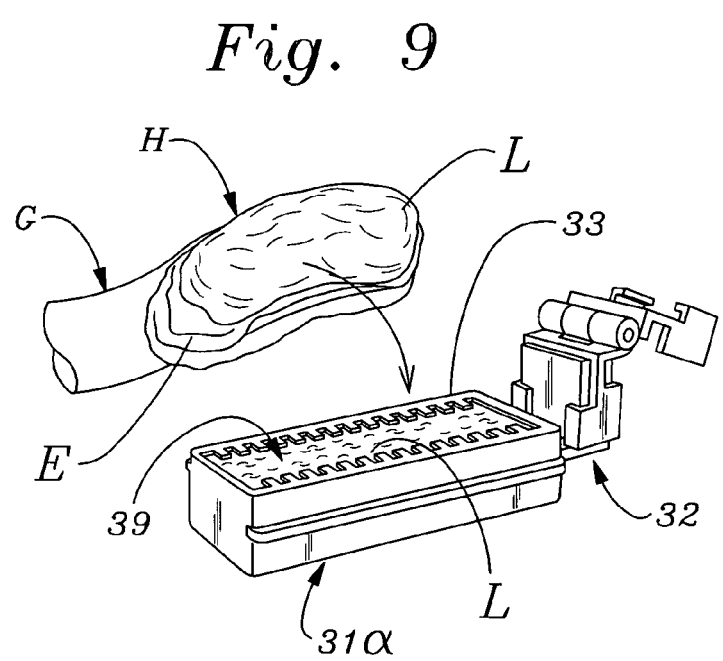
FIG. 9 is a perspective view showing a first step in a method of making a master dental model cast and an opposing cast from master and opposing impression molds made of teeth in opposite jaws of a patient by a double-bite or "triple" impression tray.
Figure 10:
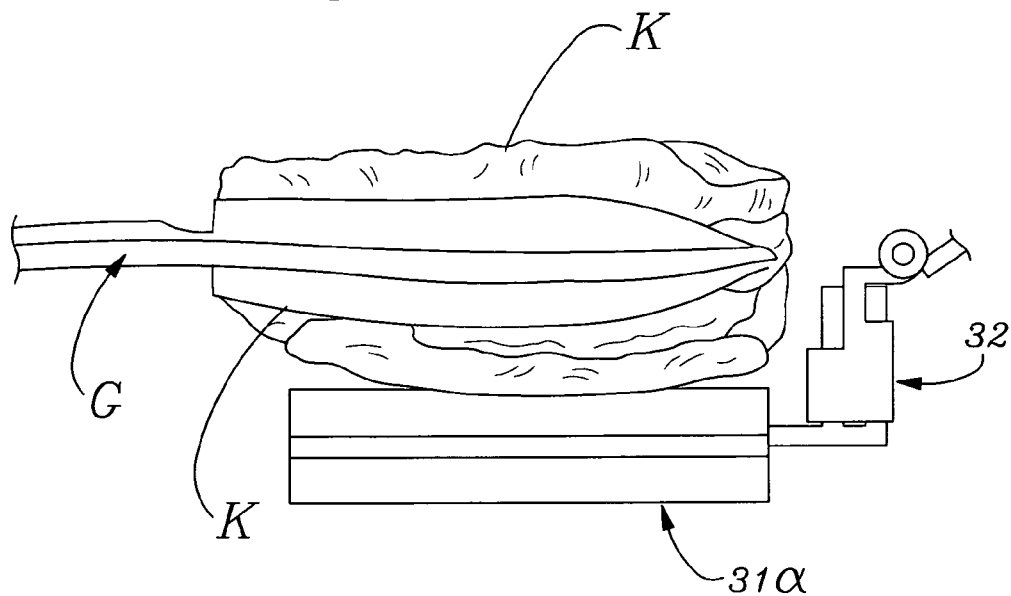
FIG. 10 is a perspective view of a second step in fabricating master and opposing articulated casts according to the present invention.
Figure 11:
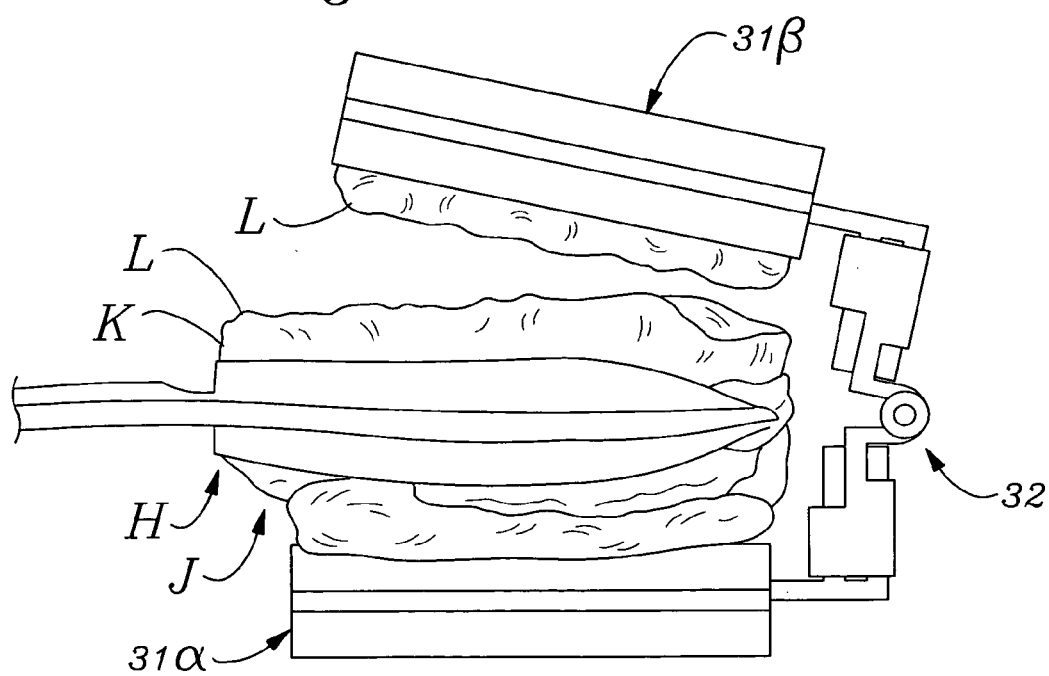
FIG. 11 is a perspective view of a third step in the method of FIG. 10.

FIGS. 9-11 illustrate preliminary steps in making master and opposing dental model casts from master and opposing mold impressions made by teeth in upper and lower jaws of a patient, use a "double-bite" or "triple" impression tray.

FIGS. 12-15 illustrate further steps in the method of fabricating a dental prostheses model according to the present invention, from either a single-bite or double-bite impression.

Figure 17:
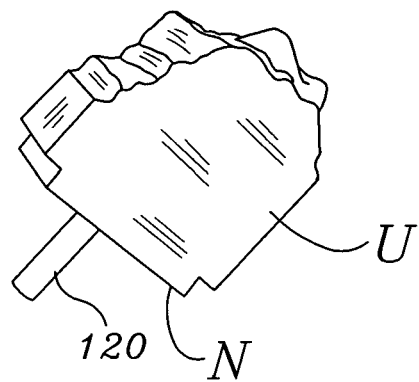
FIG. 17 is a fragmentary view of the dental cast of FIG. 14 on an enlarged scale, showing a die segment thereof.
Figure 16:
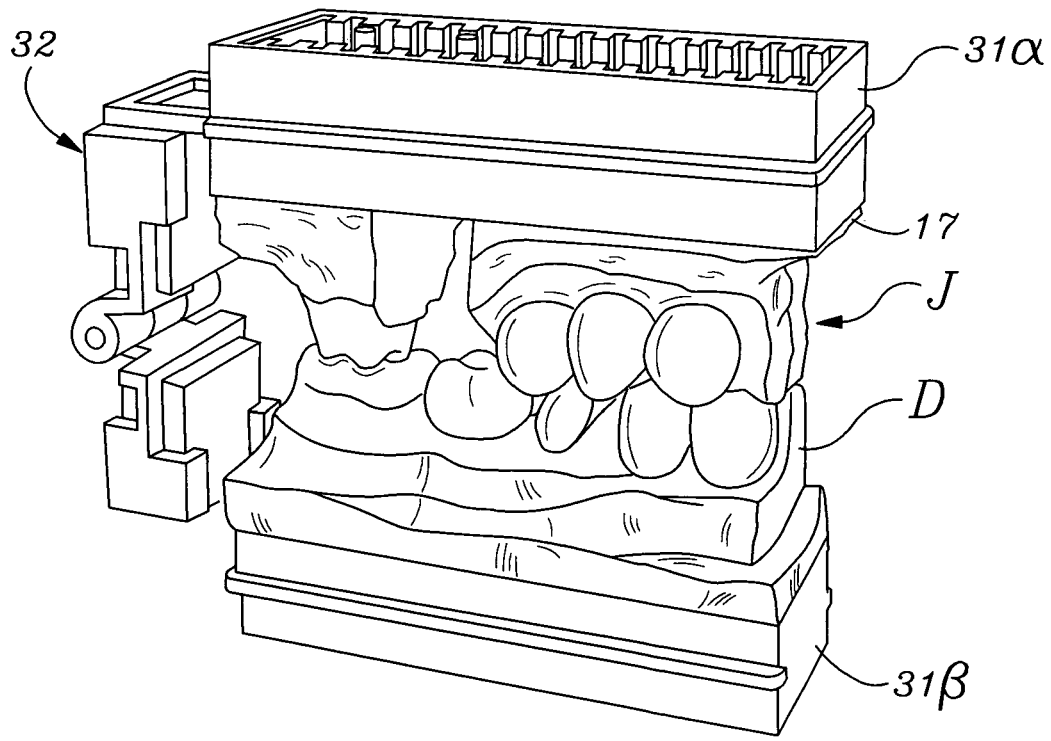
FIG. 16 is a perspective view of a completed articulatable model of a pair of master and opposing dental modeling system casts fabricated using the method and apparatus according to the present invention.
Figure 18:
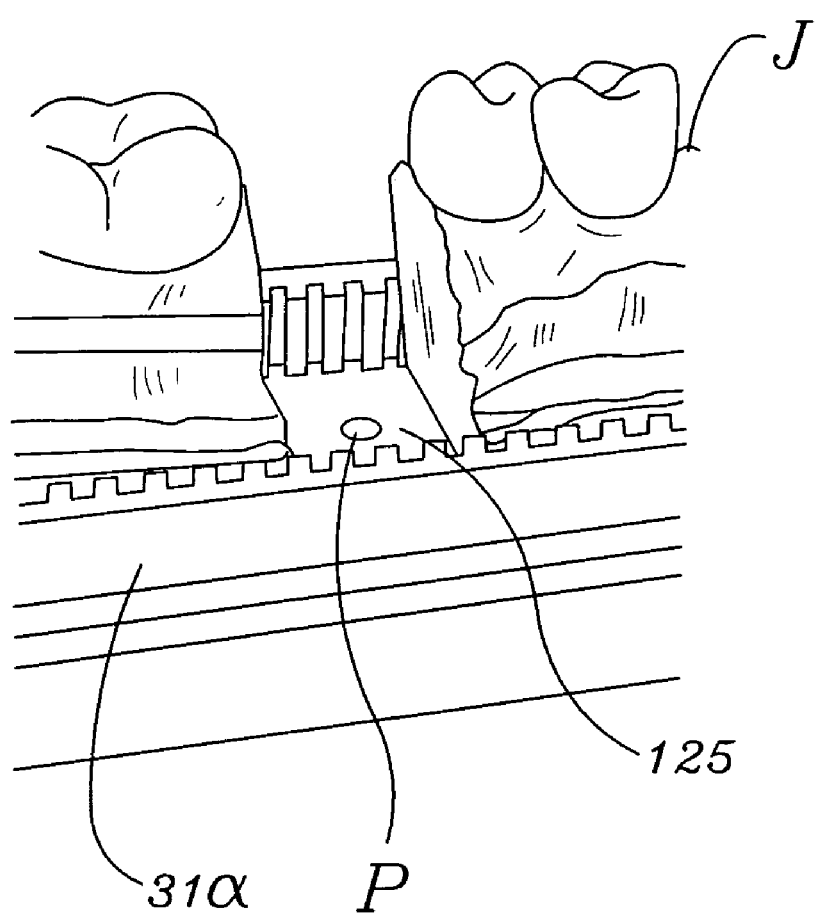
FIG. 18 is another fragmentary view of the article of FIG. 11 on an enlarged scale, showing part of a master cast with the die segment of FIG. 17 removed from the cast.

FIGS. 16-18 illustrate a finished pair of dental prostheses model casts mounted in an articulator according to the present invention.

FIGS. 19-21 illustrate tools for use in practicing the present invention.

FIGS. 22-27 illustrate an alternative apparatus and method for making dental model casts according to the present invention.

FIGS. 28-35 illustrate the construction and use of a re-usable symmetric double-well modeling tray and insert according to the present invention.

FIGS. 36-39 illustrate components of a full-arch symmetric double-well dental modeling prostheses tray according to the present invention.

Figure 40A:
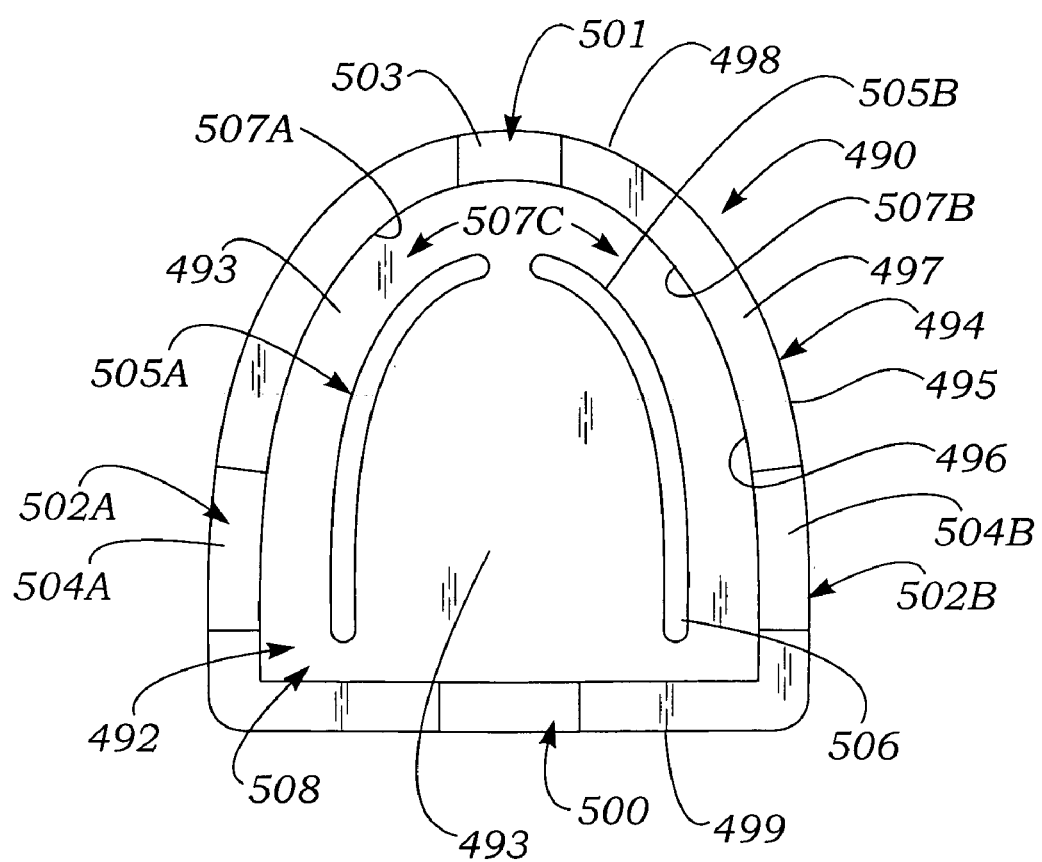
FIG. 40A is an upper plan view of an anvil template for use in removing a full-arch dental model cast from the tray of FIG. 36.
Figure 40B:
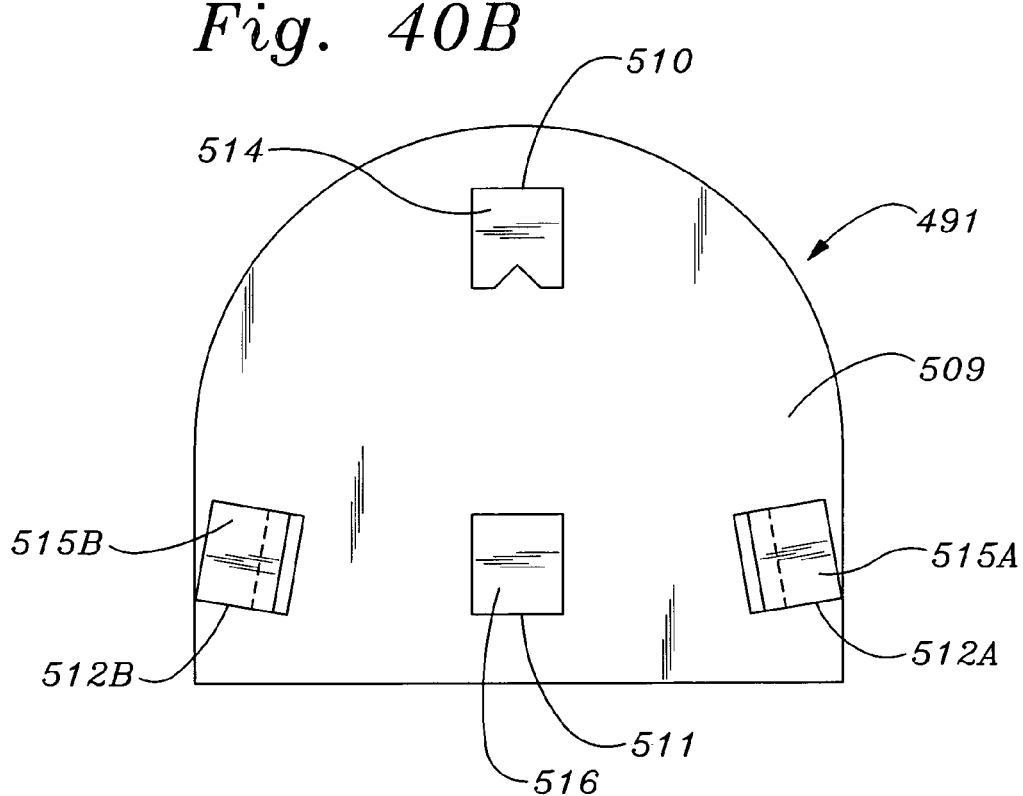
FIG. 40B is a lower plan view of a knock-out tool for use with the anvil template of FIG. 40A in removing a full-arch dental model cast from the tray of FIG. 36.
Figure 41:
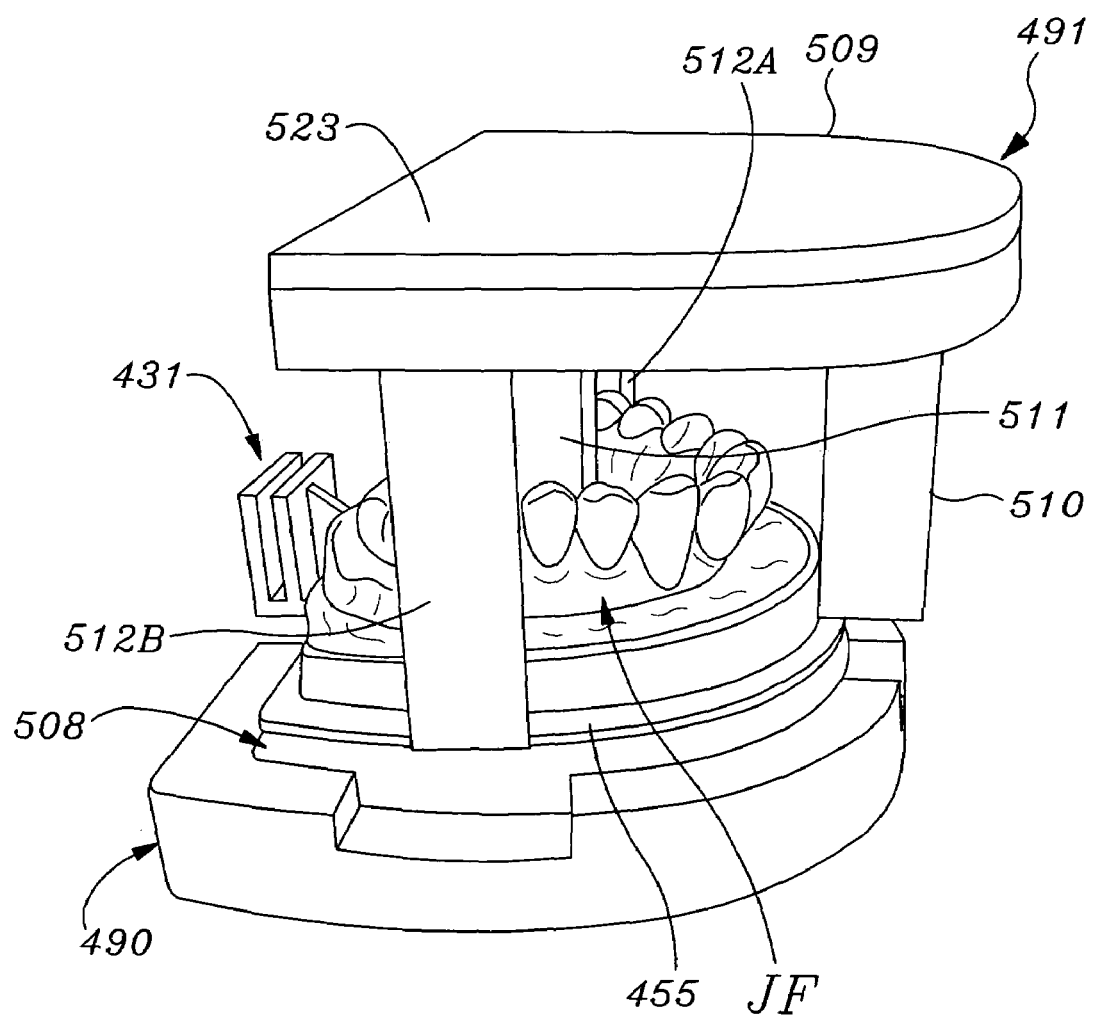
FIG. 41 is a perspective view showing the manner of using the anvil template and knock-out tool of FIGS. 40A and 40B to eject a full-arch cast dental model from the tray of FIG. 36.

FIGS. 40-41 illustrate the structure and use of a full-arch anvil template and knock-out for removing a full-arch dental model cast from the modeling tray shown in FIGS. 36-39.

Figure 42A:
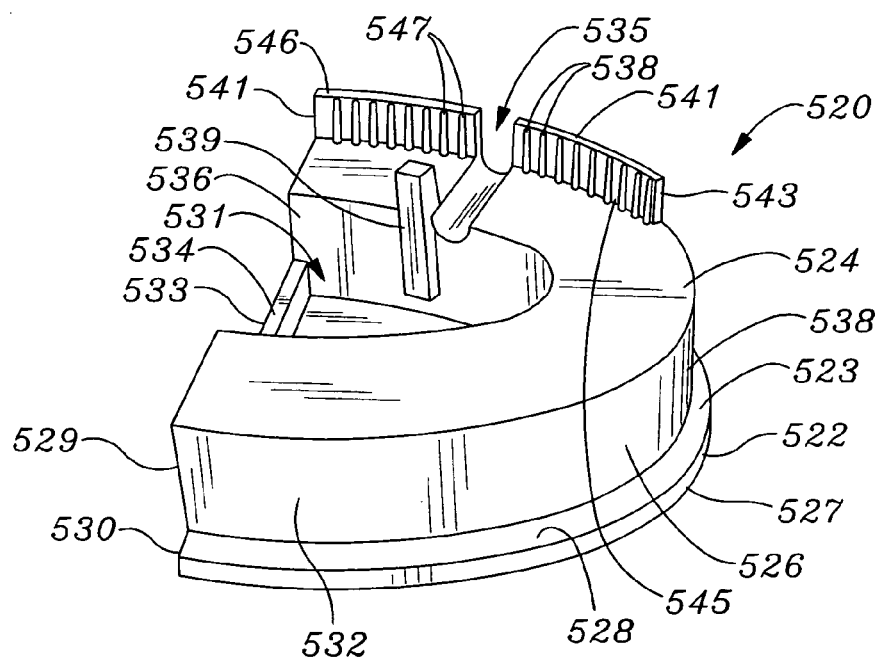
FIG. 42A is a right side perspective view showing a full-arch sawing fixture.
Figure 42B:
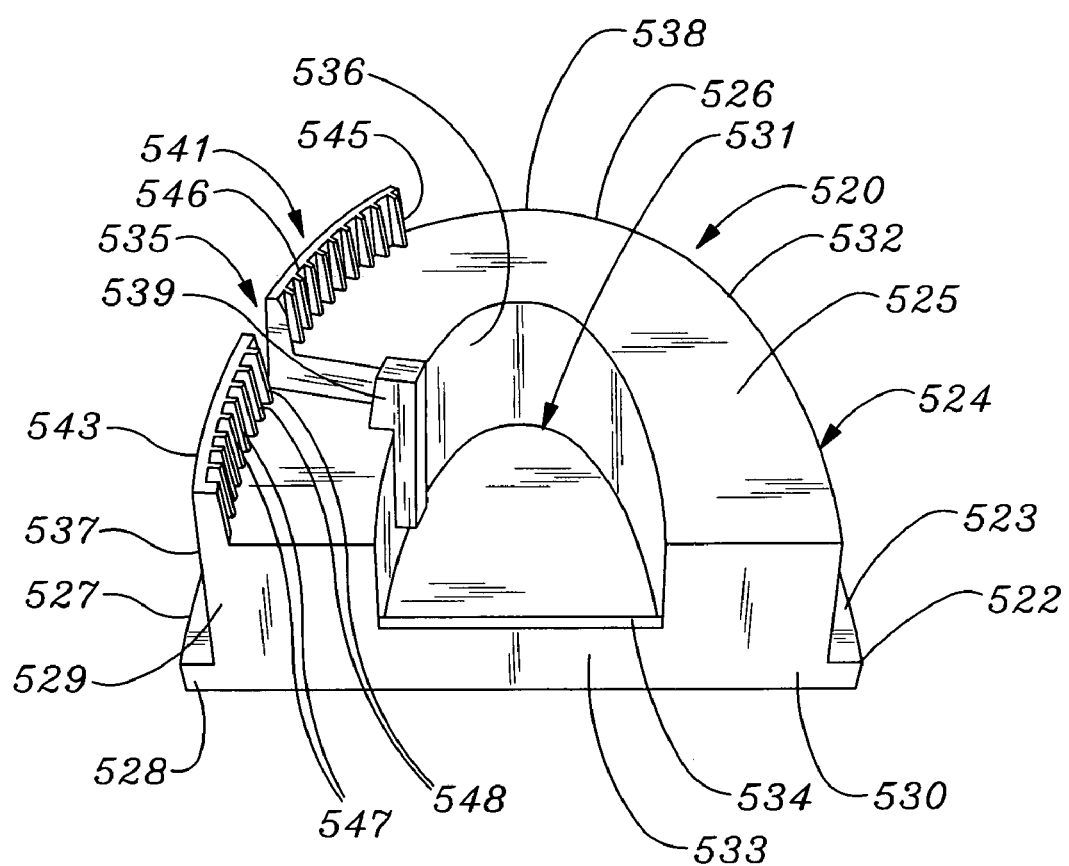
FIG. 42B is a rear perspective view of the full-arch sawing fixture of FIG. 42A.
Figure 43:
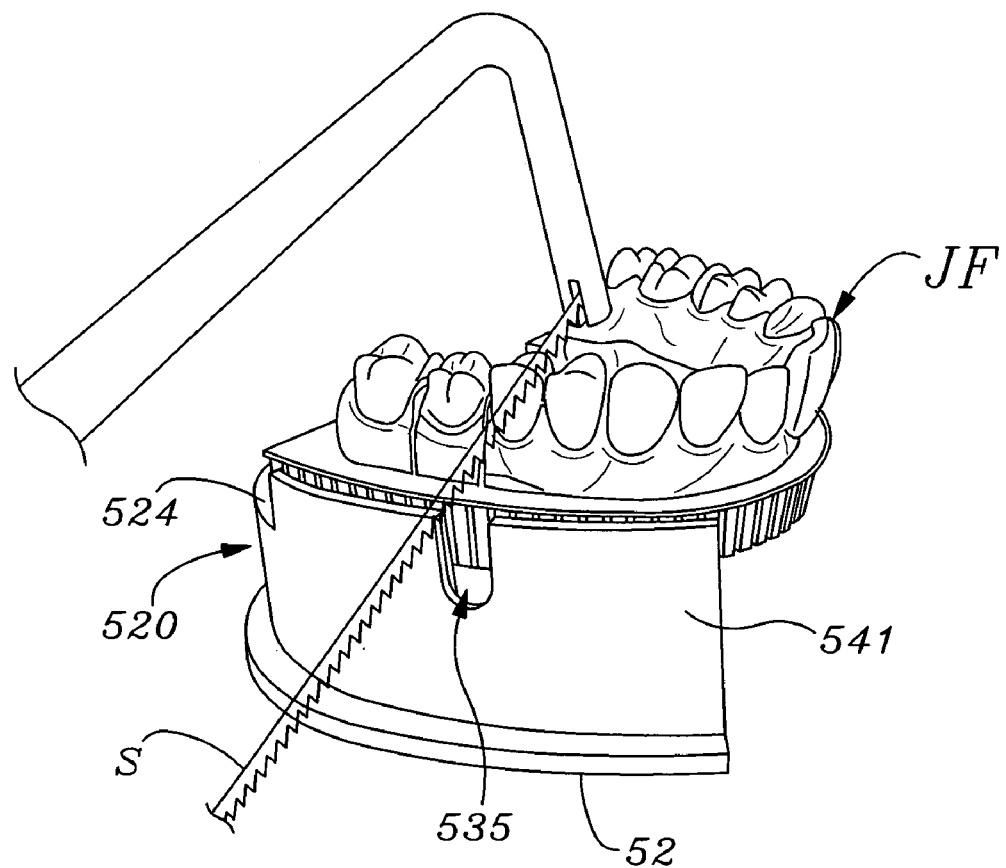
FIG. 43 is a perspective view showing the full-arch sawing fixture of FIGS. 42A and 42B being used to partition individual die segments from a full-arch dental model casting.

FIGS. 42 and 43 illustrate the structure and function of a full-arch sawing fixture according to the present invention.

FIGS. 44-49 illustrate the structure and function of a full-arch drilling fixture according to the present invention.

FIG. 50 illustrates a prior art method of attaching full-arch dental model casts to a laboratory dental articulator.

FIGS. 51-61 illustrate the structure and function of a full-arch articulator slide receptacle according to the present invention.

FIGS. 62-65 illustrate the construction and use of a re-usable full-arch modeling tray and insert apparatus to the present invention.

FIGS. 66-72 illustrate modifications of the tray and insert of FIGS. 1-3, and 30-32, respectively, which are provided with a groove forming rib.

B. Detailed Description

Figure 1:
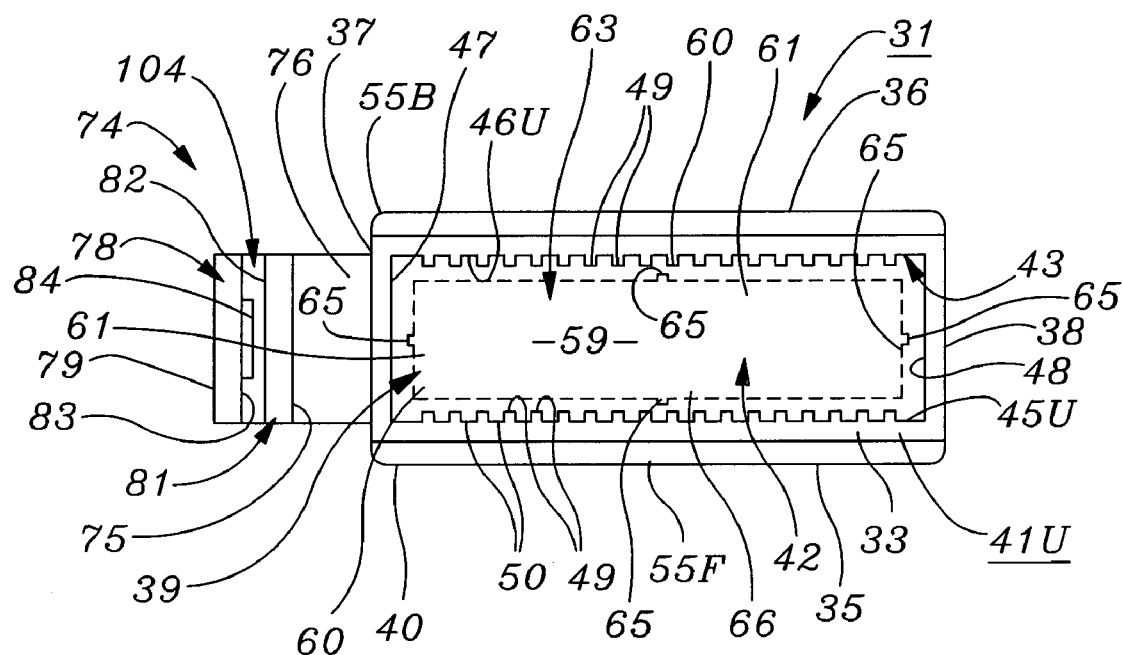
FIG. 1 is an upper plan view of a symmetric double-well quadrant modeling tray for a dental prostheses modeling system according to the present invention.

Referring now to FIGS. 1-3, an apparatus 30 for making dental prostheses quadrant models according to the present invention may be seen to include a pair of quadrant symmetric double-well molding trays 31A, 31B which are releasably connectable by a hinge mechanism 32 and used for fabricating and holding dental models made according to the present invention. As shown in FIG. 16 and as will be described in detail below, hinge mechanism 32 enables trays 31A, 31B to be pivoted between a mutually co-planar horizontally disposition as shown in FIG. 2, to a configuration in which one of the molding trays overlies the other in a generally parallel disposition, as shown in FIGS. 2 and 16.

As will be made clear in the ensuing description, only one of the quadrant molding trays 31A, 31B need by provided with certain novel structural features according to the present invention, if a removable dental model cast is to be made of teeth in a single jaw of a patient. However, according to a preferred method of practicing to the invention, trays 31A and 31B may be identical, and for the sake of brevity in the ensuing description, the letter suffix A or B is deleted unless necessary to distinguish between two trays, e.g., a tray in which a master dental cast is molded versus a tray in which an opposing cast is molded.

As shown in FIGS. 1-3, each quadrant tray 31 has a longitudinally elongated generally rectangular plan view shape. Tray 31 preferably has flat and parallel upper and lower surfaces 33, 34, respectively. Also, tray 31 has longitudinally elongated, rectangularly shaped, generally vertically disposed front and rear side walls 35, 36, a rectangularly shaped inner (hinge side), vertical end wall 37 and an outer vertically disposed end wall 38.

As shown in FIG. 1, quadrant tray 31 includes a thin rectangular plate-shaped base partition or base wall panel 42, which is located within the tray, disposed parallel to and approximately equidistant from upper and lower surfaces 33, 34 of the tray, thus partitioning the interior of the tray into generally symmetrical upper and lower parts. Base or partition wall 42 forms with adjacent vertical inner walls in an upper part of tray 31, a relatively deep rectangularly-shaped upper depression or upper well 39, and in a lower part of the tray a lower well 63 shaped symmetrically to the upper well. Upper and lower wells 39, 63 are concentric with the outer vertically disposed perimeter wall surface 40 of tray 31, and are nearly as large as the outer perimeter of the tray. Thus arranged a thin rectangularly-shaped ring comprised of upper and lower peripheral ring portions 41U, 41L having a thickness of about 1/8 inch is formed between upper and lower wells 39, 63 and outer vertical perimeter wall surface 40 of tray 31. Peripheral rings 41U, 41L have disposed perpendicularly outwards from base wall 42, i.e., upwardly and downwardly, respectively, an inner peripheral wall surface 43 which includes front longitudinally disposed inner surfaces 45U. 45L, rear longitudinally disposed inner surfaces 46U, 46L, and shorter transverse end surfaces, i.e., a left transverse inner surface 47, and a right transverse inner surface 48.

As shown in FIG. 2, upper and lower wells 39 and 63 have approximately equal, depths which are relatively large with respect to their cross-section area dimensions, i.e., about 9/32 inch for a well about 2¼ inch long by about ¾ inch wide. The reasons that both wells are relatively deep will become clear from the ensuing description.

Referring again to FIG. 1, longer front and rear inner wall surfaces 45, 46 of an upper portion 41U of peripheral ring 41 have formed therein a plurality of vertically disposed ribs 49 which protrude inwardly towards a longitudinal center line of upper well 39. Ribs 49 protrude vertically upwardly of base wall 42, and form between each adjacent pair of ribs a vertically disposed notch or groove 50. As will be described in detail below, alternating ribs and grooves 49, 50 form complementary grooves and ribs in outer vertical surfaces of the base of a dental model cast which is formed in upper well 39 by solidified liquid die stone poured into the upper well, thus enabling the base of a cast and individual segments severed from the base, to be removably returned to exact pre-existing locations within tray 31, because of the indexing action of the ribs and grooves being insertably received within complementary-shaped grooves and ribs molded into the sides of the model cast from hardened liquid die stone. As shown in FIG. 3, lower portions of front and rear wall surfaces 45, 46 of a lower portion 41L of ring 41 adjacent to lower well 63 are optionally provided with ribs and grooves 49B, 50B which may be extensions of ribs and grooves 49, 50.

Referring now to FIGS. 1, 2, and 3, it may be seen that tray 31 is provided with front and back or rear abutment flanges 55F, 55B, which protrude outwardly from front and rear walls 35, 36, respectively, of tray 31. As shown in the figures, each abutment flange 55F, 55B has the shape of a horizontally disposed, thin, longitudinally elongated rectangular rib or web which has an outer vertical wall surface 56 that is spaced outwards from an outer front or rear wall of tray 31, and flat and parallel, horizontally disposed, upper and lower surfaces 57, 58, respectively. The function of front and rear abutment flanges 55F, 55B are described below.

Referring now to FIGS. 1 and 3, it may be seen that base wall 42 of upper well 39 in molding tray 31 has a flat upper surface 59, and includes an outer rectangular ring-shaped peripheral portion 60 formed of flanges which protrude perpendicularly inwards from the inner wall surfaces of the front, rear, inner and outer end walls of the tray. Base wall 42 also includes a concentrically located, longitudinally elongated rectangularly-shaped center knock-out or break-away panel 61. Base wall 42 has a thickness of less than the height of tray 31, e.g., about 1/16 inch for a tray height of about 5/8 inch, and upper surface 59 of base wall 42 is located about 9/32 inch below upper peripheral edge wall 33 of the tray. Thus arranged, base wall 42 forms within upper and lower portions of tray 31 relatively deep, e.g., about 9/32 inch, symmetrically shaped upper and lower wells 39 and 63, respectively, which protrude inwardly from upper peripheral face 59 and lower peripheral face 64 of the tray, respectively.

Figure 23:
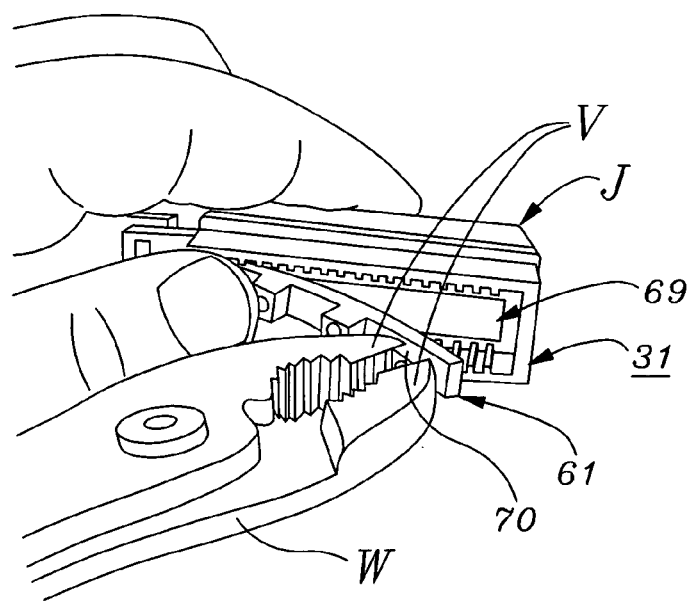
FIG. 23 is a perspective view of an alternative method for removing a break-away base panel from a tray comprising a component of the apparatus according to the present invention, without simultaneous ejection of a dental model cast from the tray, as shown in FIG. 12.

Referring still to FIGS. 1 and 3, it may be seen that center break-away panel 61 of tray base wall 42 is connected to outer rectangular ring-shaped portion 60 of the base wall by a plurality of readily breakable, or frangible members 65. Thus, as shown in FIG. 3, outer vertical wall surface 66 of base wall break-away center panel 61 is joined to an inner vertical wall surface 67 of ring-shaped portion 60 of the base wall by a plurality of thin, breakable pins 65, e.g., a pair of front and rear pins and a pair of left and right pins. In a preferred embodiment, a tray 31 is fabricated as a unitary molded plastic part, with outer surface 66 of break-away center panel 61 angled downwardly and inwardly away from adjacent inner wall surface 67 of ring-shaped outer portion 60 of base wall 42. With this construction, pins 65 may be readily molded to have a thickness substantially less than that of break-away center panel 61, thus enabling the pins to be readily broken and thereby permitting the center panel to be broken away and removed from tray 31. With break-away center panel 61 thus removed from tray 31, base wall 42 of the tray has through its thickness dimension a concentrically located, longitudinally elongated rectangular-shaped aperture 69, as shown in FIG. 23.

As shown in FIG. 3, center break-away panel 61 of tray base wall 42 preferably is provided with one or more bosses 70 which protrude perpendicularly downwards from the lower surface 71 of the base wall. Although the exact shape and size of bosses 70 is not critical, the embodiment of tray 31 shown in FIG. 3 has three square cross-section bosses 70 which each have a flat lower surface 72 and a blind circular bore 73 which extends perpendicularly upwards from the lower surface. The three bosses 70 include a longitudinally centrally located center boss 70C, and left (inner) and right (outer) bosses 70L, 70R spaced equal longitudinal distances away from the center boss. The function and purpose of bosses 70 is described below.

Referring to FIGS. 1, 2 and 3, it may be seen that each tray 31 has protruding horizontally outwards from a short end wall 37 thereof a hinge coupler bracket 74 for releasable attachment to hinge mechanism 32. Each hinge coupler bracket 74 has a shape approximating that of an L-bracket, an upright leg of which is bifurcated into two spaced apart, parallel plates. Thus, as shown in FIGS. 1-3, hinge coupler bracket 74 includes a rectangularly-shaped base plate 75 which protrudes outwardly from end wall 37 of tray 31. Base plate 75 has horizontally disposed upper and lower surfaces 76, 77 which are parallel to upper surface 33 of tray 31. Upper surface 76 of bracket base plate 75 is preferably recessed below upper surface 33 of the perimeter edge wall of tray 31, and has protruding perpendicularly upwards therefrom a first, outer rectangularly-shaped upright leg plate 78. Outer upright leg plate 78 has an outer vertical surface 79 which is co-planar with outer vertical edge wall 80 of a base plate 75.

Bracket 74 includes a second, inner upright leg plate 81 which is shaped similarly to outer leg plate 78, and which protrudes perpendicularly upwards from base plate 75 at a location spaced longitudinally inwardly from the outer upright leg plate. Inner upright leg plate 81 has an outer vertical wall surface 82 which is spaced longitudinally inwards of and parallel to an inner vertical wall surface 83 of outer leg plate 78. Preferably, a rectangularly-shaped aperture 84 is formed through base plate 75 of bracket 74, between outer and inner upright leg plates 78, 81. The purpose of aperture 84 is to facilitate elastic flexure of the outer and inner leg plates away from and towards one another, thereby facilitating elastic gripping engagement of hinge mechanism 32, as will be described below.

Figure 3A:
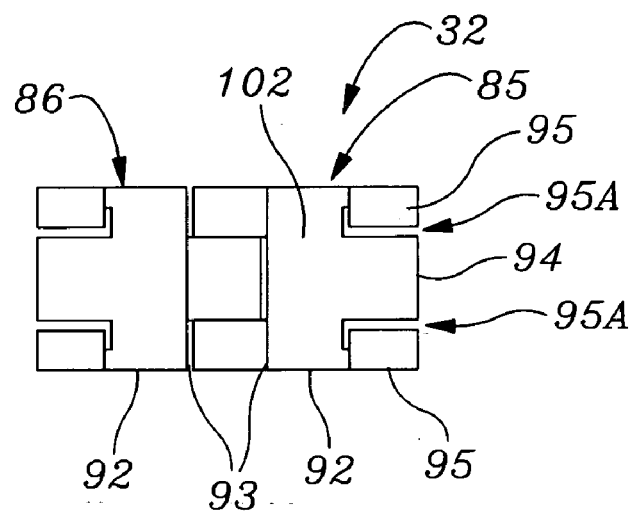
FIG. 3A is an upper plan view of the hinge coupler of FIG. 3.
Figure 3B:
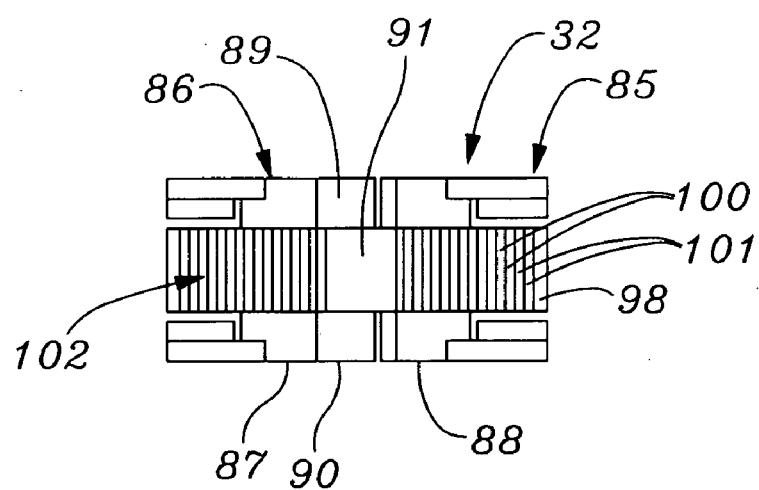
FIG. 3B is a lower plan view of the hinge coupler of FIG. 3.

Referring still to FIGS. 2, 3A, 3B, 6, and 7, it may be seen that hinge mechanism 32 of apparatus 30 includes a pair of rectangular plan-view hinge members 85, 86, each having a thin upper rectangularly-shaped plate 87,88, respectively. Plate 87 has a pair of spaced apart, coaxially tubular extensions 89,90, which protrude upwardly from an inner end of the plate, parallel thereto. Plate 88 has a single, centrally located tubular extension 91 which fits coaxially between tubular extensions 89, 90 of plate 87, and is hingedly joined thereto by an elongated cylindrical hinge pin 91A which is disposed rotatably through bores (not shown) of the tubular extensions. The other parts of hinge members 85, 86 are identical, and include a larger rectangularly-shaped coupler plate 92 which depends perpendicularly downwardly from outer edge 93 of each upper plate. Coupler plate 92 has at opposite sides of a lower horizontal edge wall 94 thereof a pair of vertically disposed, L-shaped guide members 95 which form therebetween a pair of vertically disposed C-shaped channels 95A which are adapted to vertically upwardly insertably receive an inner upright leg plate 81 of a tray 31. Each hinge member 85, 86 also has protruding laterally inwardly from the L-shaped guide member 95 a vertically disposed lug member 96. Each lug member 96 has an inner vertical edge wall 97 which is located parallel to and laterally spaced apart from an inner vertical edge will 98 of coupler plate 92. As shown in FIG. 2, inner facing edge walls 97 of lug members 96 abut to limit inward pivotable motion of the coupler plates to a parallel position. As shown in FIG. 3B, inner vertical edge wall 98 of each coupler plate 91 preferably has formed therein a plurality of parallel, horizontally disposed, triangular cross-section ribs 100 which alternate with grooves 101 to form a washboard-like surface 102. The thickness of hinge coupler plate 92, measured between the vertices of triangular webs 100 and outer surface 102 of the coupler plate, is slightly greater than the spacing between an inner and outer faces 83, of outer and inner leg plate uprights 78, 81 of hinge coupler bracket 74 of tray 31. Thus, when coupler plate 92 is inverted downwardly into the space 104 between the tray upright leg plates, the latter flex elastically slightly apart, and ribs 100 bite into the plates slightly, thus frictionally engaging the coupler plate with the tray legs. A description of certain components of a pin tray dental prostheses modeling system according to the present invention having been given, the manner of using those components according to methods of the present invention is presented below.

Figure 4:
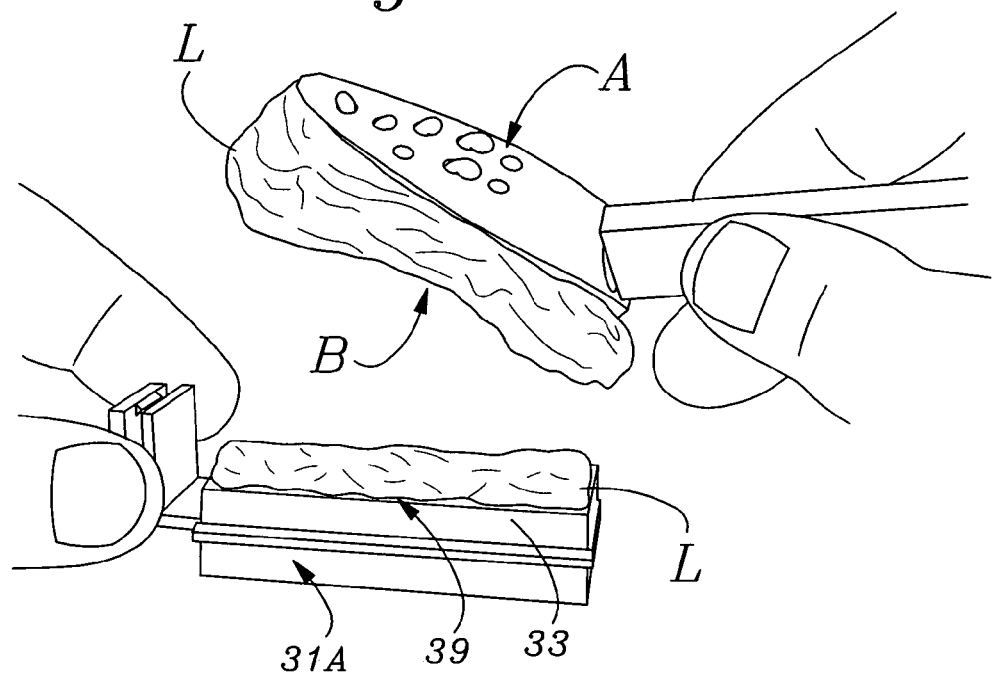
FIG. 4 is a perspective view showing a first step of a method for making a modeling cast or "arch" from a single quadrant impression mold made of a group of a patient's teeth located in either an upper or lower jaw and including one or more teeth to be renovated.
Figure 5:
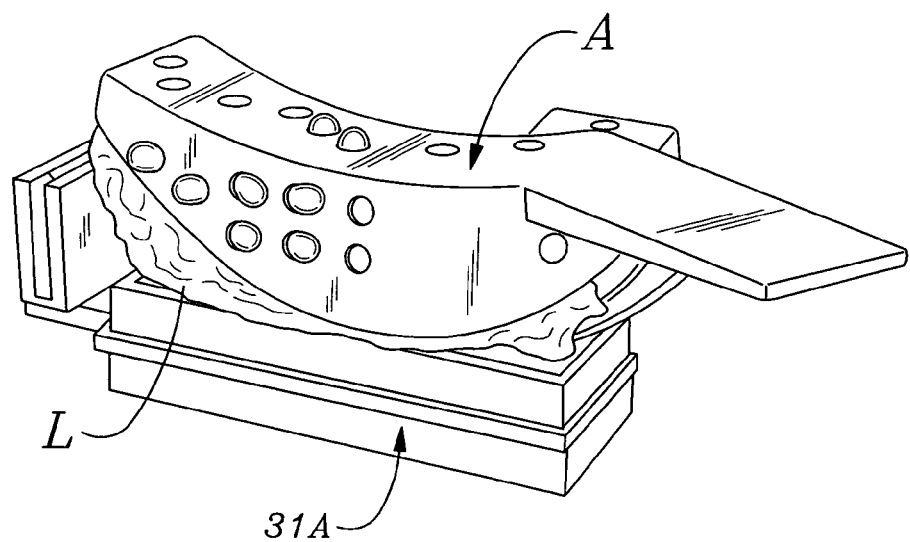
FIG. 5 is a perspective view of the arrangement of FIG. 4 showing a second step in making a dental model cast from a single quadrant impression.

FIG. 4 illustrates a first step in making a dental prostheses model cast or "arch" from a single quadrant impression mold made of a group of a patient's teeth located in a left or right half of an upper or lower jaw of the patient. As shown in FIG. 4, upper well 39 in the upper portion of a first molding tray 31A is filled with a semi-liquid die stone material such as plaster of Paris, to a level slightly above upper peripheral wall 33 of the tray. As is also shown in FIG. 4, a dental impression mold A containing imprints B of a patient's teeth is also filled to overflowing with liquid die stone. In a second step of making a dental model, filled impression A is then inverted, positioned over tray 31A, and pressed down onto the semi-liquid die stone in the tray, as shown in FIG. 5. The semi-liquid die stone in impression A thus co-mingles with that in tray 31A. Time is then allowed for the liquid die stone in tray 31A to harden into a stone-like cast. Next, impression mold A is peeled upwardly and off from the hardened die stone in tray 31, leaving therein a cast C which is an accurate replica of teeth which impressed or imprinted the impression mold, as shown in FIG. 6.

Figure 8:
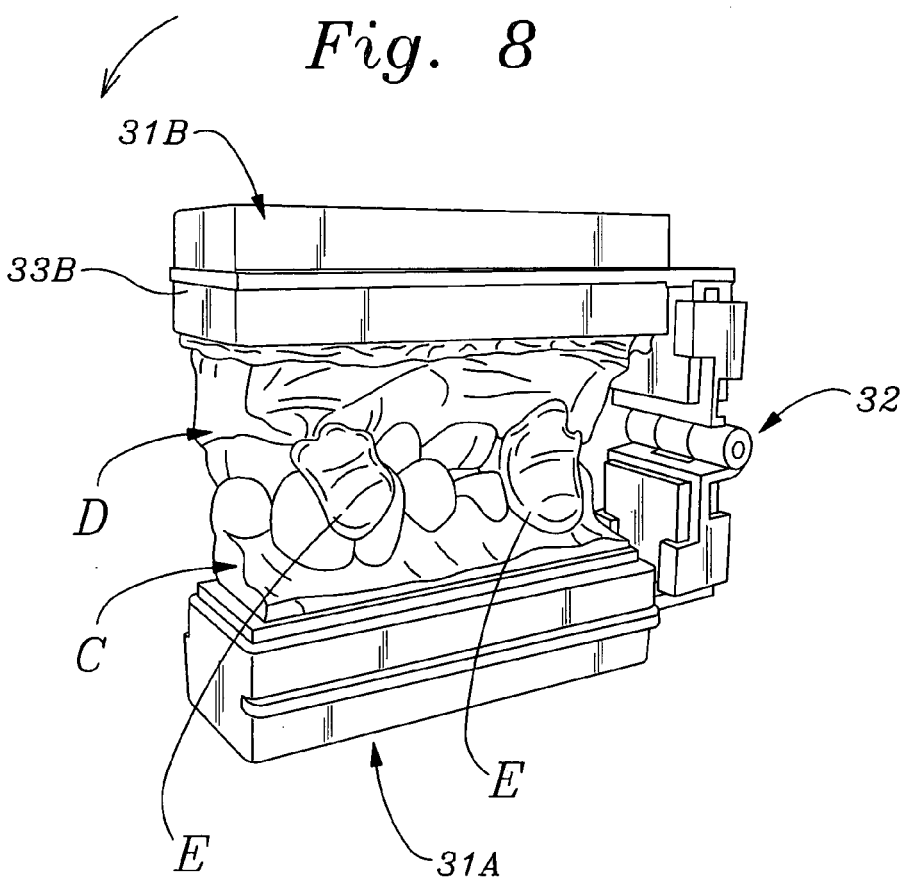
FIG. 8 is a view similar to that of FIG. 7, but showing a fifth step in which the opposing tray pivoted on the axis of the hinge coupler to thereby bring the semi-liquid die stone material in the opposing tray and the upper surface of the opposing casting into contact to thereby co-mingle and cohere upon hardening, thus securing the opposing cast to the opposing tray.

Then, in a third step, as shown in FIG. 6, a cast D made of an impression taken of teeth opposing those which are to be restored and which imprinted impression A is positioned above first, master cast C, which replicates teeth for which prostheses are to be fabricated. Opposing cast D is positioned in proper occlusal contact with master cast C, and temporarily secured in that configuration by blobs of wax E, for example, as shown in FIG. 6. Next, in a fourth step, as shown in FIG. 7, a second, opposed tray 31-B, coupled by hinge mechanism 32 to tray 31-A containing master dental model cast C, is filled to overflowing with liquid die stone L, as is upper surface of opposing cast D. Then, in a fifth step, as shown in FIG. 8, the upper surface 33B of opposing tray 31-B is pivoted towards contact with upper surface F of opposing cast D, causing die stone in the upper impression to co-mingle with that in the opposing tray. Time is once again allowed for the liquid die stone in opposing tray 31-B and opposing cast D to harden. Wax blobs E are then heated slightly to melt the wax, enabling opposing tray 31-B, now secured to opposing cast D by solidified die stone, to be pivoted away from master cast C. Further processing steps used to complete pinned dental model cast C are described below, following a description of preliminary steps for making master and opposing casts from a double-bite, or triple tray impression; the final steps of making finished casts are the same for both single quadrant and triple tray impression casts.

FIGS. 9-11 illustrate a method of making dental model casts from double-bite or triple-tray impressions according to the present invention.

FIG. 9 shows a first step in making a dental prostheses model cast from a double-bite or triple-tray impression mold G made from a patient's teeth located in lower or upper jaw and including teeth which are to be replaced by or fitted with one or more prosthetic restorations or replacements, and occluding teeth in an opposing jaw. As shown in FIG. 9, upper well 39 in the upper portion of a first molding tray 31-α is filled with a semi-liquid, hardenable modeling substance such as plaster of Paris or die stone, to a level slightly above upper peripheral wall surface 33 of the tray. As is also shown in FIG. 9, a concave depression in a first, master side H of two-sided dental impression G imprinted with teeth which are to be restored, is also filled to overflowing with liquid die stone. The filled master side impression H is then inverted, positioned over tray 31-α, and pressed down into the semi-liquid die stone in the tray, as shown in FIG. 10. The semi-liquid die stone in the impression H thus co-mingles with semi-liquid die stone material in tray 31-α. Time is then allowed for the liquid die stone in tray 31-α and master impression H to harden into a stone-like master cast J. Next, liquid die stone L is poured to overflowing into a second, opposing tray 31-β, which is pivotably connected to first tray 31-α by a hinge mechanism 32.

As shown in FIG. 11, a concave depression in a second, opposing side K of two-sided impression mold G imprinted with teeth in a jaw opposed to the jaw containing teeth to be restored, is filled to overflowing with liquid die stone L. As is also shown in FIG. 11, opposing tray 31-β is then pivoted towards contact with the upper surface of semi-liquid die stone in concave impression area K of the opposing impression, causing die stone in the upper, opposing impression to co-mingle with die stone in the upper, opposing tray. Time is once again allowed for the semi-liquid die stone in opposing tray 31-β and opposing impression K to harden into a stone-like opposing cast L. Next, a master dental model cast J formed in master tray 31-α is temporarily and replaceably removed from the tray, in the following manner.

A preferred method for removing master dental model cast J from tray 31-α consists essentially of exerting an upwardly directed force on break-away center panel 61 of base wall 42 of the tray which is of sufficient strength to break pins 65 which join the center panel to peripheral ring panel 60 of the base wall, and then pushing upwardly on that portion of the lower surface M of a cast J that is accessible through aperture 69 through the base wall. According to a preferred method of removing cast J from tray 31-α, a template 190 and tool 191, shown in FIGS. 19, 20A and 20B, are employed.

Figure 12:
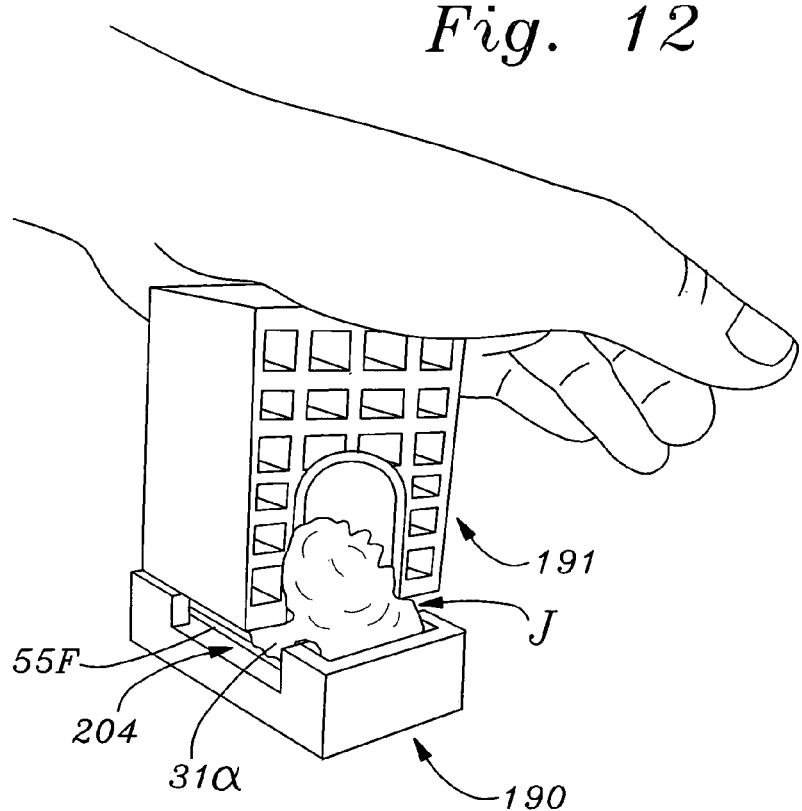
FIG. 12 is a perspective view of a fourth step of the double-tray method of FIG. 10, as well as that the single tray method of FIGS. 4-8.

As shown in FIG. 19, template 190 includes a flat base 192 having a longitudinally elongated, rectangular shape. Base 192 of template 190 has protruding perpendicularly upwards from a flat upper surface 193 thereof a longitudinally elongated, rectangularly shaped lug 194 which has a vertically disposed peripheral wall surface 195 that is located concentrically with respect to the outer peripheral wall surface 196 of the base, and has a flat upper surface 197 disposed parallel to upper surface 193 of base 192. Template 190 also includes at opposite short ends 198, 199 thereof a pair of opposed, vertically disposed guide structures 200, 201 which have formed therein a pair of opposed inner facing C-shaped guide spaces 202, 203 which together form an open rectangular-shaped tray receipt space 204 which is concentric with outer peripheral wall surface 195 of lug 194. As shown in FIGS. 12 and 19, tray receipt space 204 has a rectangular plan view shape which is similar to that of tray 31, but of larger size so that the tray may be loosely inserted downwardly into the space, the bottom surfaces 72 of bosses 70 of base wall 41 abutting upper surface 197 of lug 194.

As shown in FIGS. 20A and 20B, a knock-out tool 191 according to the present invention includes a rectangular block-shaped body 205 which has vertically elongated, rectangularly-shaped parallel left and right side walls 206L, 206R and vertically elongated, rectangularly-shaped parallel front and back side walls 207F, 207B, which are perpendicular to the side walls. Body 205 has disposed perpendicularly through left and right side walls 206L, 206R thereof an arch-shaped tunnel 208. Body 205 of tool 191 has a flat, horizontally disposed upper end wall 209, and a flat lower wall surface 210. Tunnel 208 penetrates lower wall surface 210, thus defining between front and back side walls 207F, 207B a pair of front and rear legs 211F, 211B which have opposed lower, inner vertical wall surfaces 212F, 212B which border the tunnel. Legs 211F, 211B each has at a lower end thereof a laterally disposed rectangularly shaped foot flange 213F. 213B which has a flat lower surface coextensive with lowerwall surface 210 of body 205, and flat, parallel upper surfaces 214F, 214B. Foot flanges 213F, 213B protrude horizontally a short distance inwards into tunnel 208, and have vertically disposed, inner facing parallel end walls 215F, 215B. Foot flange front and back end walls 215F, 215B are spaced apart at a distance slightly greater than the space between the outer surface of front and peripheral upper edge walls of tray 31.

FIG. 12 illustrates the use of template 190 and knock-out tool 191 to remove a dental cast J from tray 31-α. As shown in FIG. 12, tray 31-α containing cast J is placed in opening 204 of template 190, with bottom surfaces 72 of bosses 70 supported on upper surface 197 of lug 194. Knock-out tool 191 is then positioned above front and back abutment flanges 55F, 55B of tray 31 with lower surfaces of front and back knock-out tool flanges 213F, 213B contacting the upper surfaces of the abutment flanges of the tray. A sharp blow is then delivered downwardly to the upper surface of the knock-out tool which causes the knock-out tool flanges to exert a downward force on the tray abutment flanges, thus causing lug 197 to exert an upwardly directed force on break-away center panel 61 of tray base wall 42, thereby breaking pins 65 which join the center panel to rectangular ring-shaped portion 60 of the base wall, and thereby ejecting cast J upwardly and out from the tray.

Figure 13:
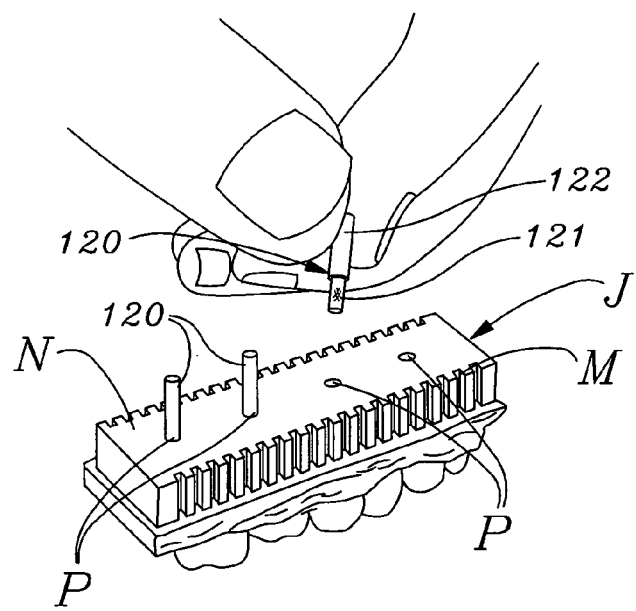
FIG. 13 is a perspective view of an optional step in the double tray method of FIG. 10, as well as the single tray method of FIGS. 4-8, in which manipulating pins are installed in a dental model cast.

Dental prostheses models fabricated utilizing the novel method and modeling tray described above may optionally be fitted with pins to facilitate manipulating the models during the course of manufacturing finished dental restorations. Thus, as shown in FIG. 13, a fifth, optional step in making a dental prostheses model according to the present invention consists of drilling blind pin bores P into the base M of an inverted cast J, at locations aligned with portions of the cast which are to be severed from adjacent portions of the cast, to thereby form die segments which are to be used as models for dental prostheses. Pin bores P are also drilled into locations of the base corresponding to portions of the cast adjacent to die segments.

After pin bores P have been drilled into cast J as described above, cylindrical metal pins 120 are inserted into the base. As shown in FIG. 13, each pin has a short knurled end 121 and a longer smooth shank 122. Pin bores P are drilled to a depth approximating the length of knurled end 121 of pin 120, so that the smooth shank 122 protrudes perpendicularly downwards from lower face N of individual die segments U severed from the cast J as will be described below. Pins 120 are preferably secured in pin bores P by coating knurled ends 121 of each pin with adhesive before inserting a pin into a bore.

Figure 14:
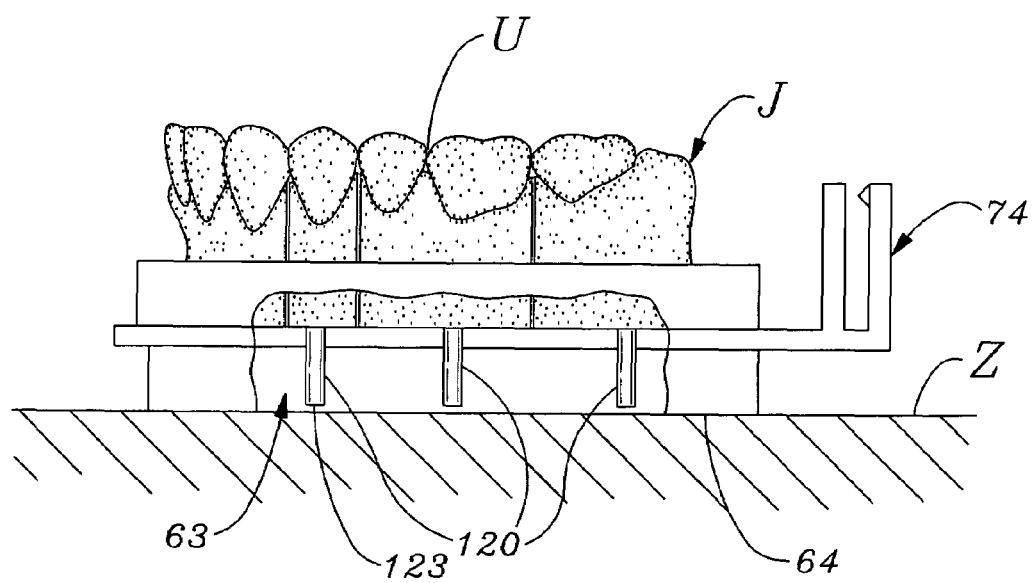
FIG. 14 is a partly broken away elevation view showing a pinned quadrant cast installed in a double-well quadrant modeling tray according to the present invention.

FIG. 14 shows a dental model cast J fitted with pins 120 in the manner described above and installed in a tray 31. As shown in FIG. 14, lower well 63 of tray 31 is sufficiently deep to position lower surfaces 123 of the pins above lower wall surface 64 of the tray, and thus above a supporting surface Z on which the tray may be placed.

Figure 15:
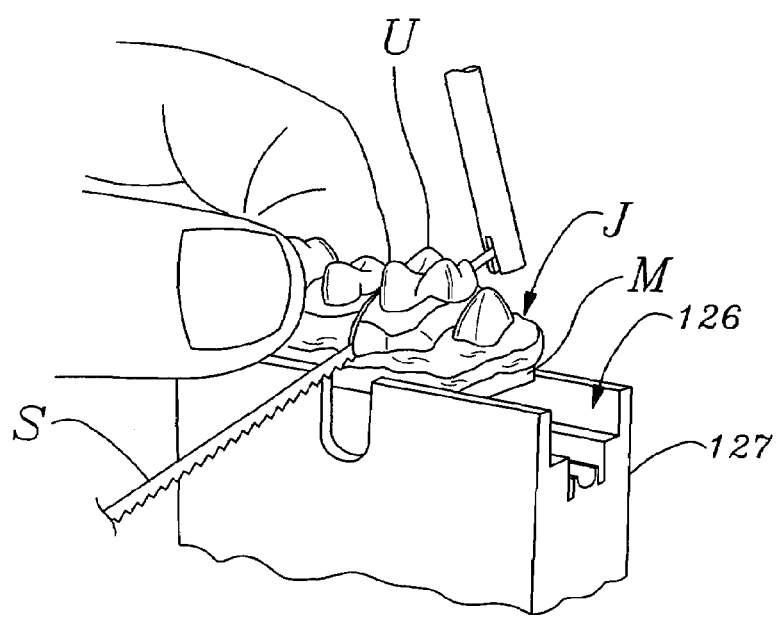
FIG. 15 is a perspective view of a final step in the double tray method of FIG. 10, as well as the single tray method of FIGS. 4-8, in which individual die segments are severed from a dental model cast.

FIG. 15 illustrates a method of severing individual die segments from a cast L. Thus, as shown in FIG. 15, base M of pinned cast L is placed upright in a longitudinally disposed horizontal channel 126 formed in the upper surface of a longitudinally elongated, rectangular block-shaped sawing stand fixture 127 of the type shown in FIG. 21. A saw S is then used to make a pair of vertical cuts T through cast J, on each side of a portion of the cast which is to be used as die segment U for use as a dental prostheses model. As shown in FIG. 21, a pair of transversely spaced apart and aligned front and rear grooves or cutouts 129F, 129B are cut downwardly from upper edges of front and rear walls 128F, 128B of fixture 127, the grooves providing clearance for saws. After one or more die segments U have been severed from dental model cast J, the die segments and adjacent portions of the cast may be repeatedly re-installed in tray 31 at precisely indexed locations, owing to the interlocking action of ribs and grooves of the cast engaging complementary grooves and ribs in the inner side walls of tray 31. FIGS. 16, 17, and 18 show a completed articulateable model of a master cast J with replaceable die segments, and an opposing cast fabricated by the above described apparatus and method according to the present invention.

FIGS. 23-27 illustrate a modification of the apparatus and method of the present invention described above. The modified apparatus and method employ the first three steps described above for both single quadrant and double-bite impression models. However, as shown in FIG. 23, a fourth step in the modified method comprises removing frangible center panel 61 of base wall 42 of tray 31 by grasping a center panel boss 70 between the jaws V of a pliers W, and exerting a pulling force sufficient to break center panel support pins 65. Blind pin bores P are then drilled into the base M of a cast J, in a manner described below, using a drilling alignment fixture 130 of the type shown in FIG. 22.

As shown in FIG. 22, drilling alignment fixture 130 includes an elongated, generally rectangular-shaped body 131 which has a flat lower surface 132, and a flat upper surface 133 in which is formed an elongated, shallow rectangular-shaped channel 134 which is adapted to receive a tray 31 containing therein the base M of a cast J.

Located in front and back sides of channel 134 are coplanar, horizontally disposed flat front and back ledges 135F, 135B which are of a proper spacing to support front and rear abutment flanges 55F and 55B of a tray 31.

Drilling alignment fixture 130 also includes a circular drill guide bushing 136 fitted through a lower wall 137 of the fixture. An index line 138 is inscribed on the outer surfaces of the fixture, in longitudinal alignment with the center line of a coaxial bushing 136.

Figure 24:
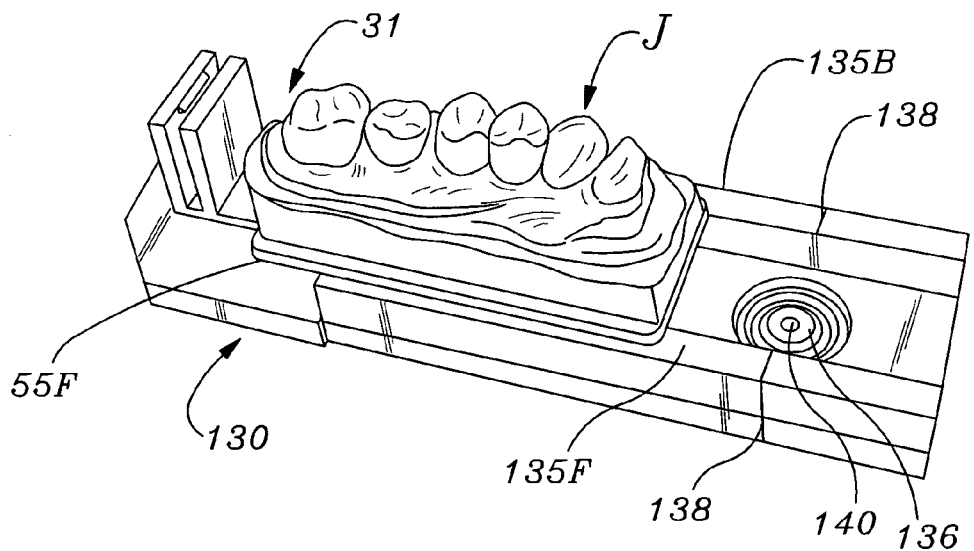
FIG. 24 is a perspective view showing the tray of FIG. 23, with the break-away base panel removed and slidably supported on the drilling alignment fixture of FIG. 21.
Figure 25:
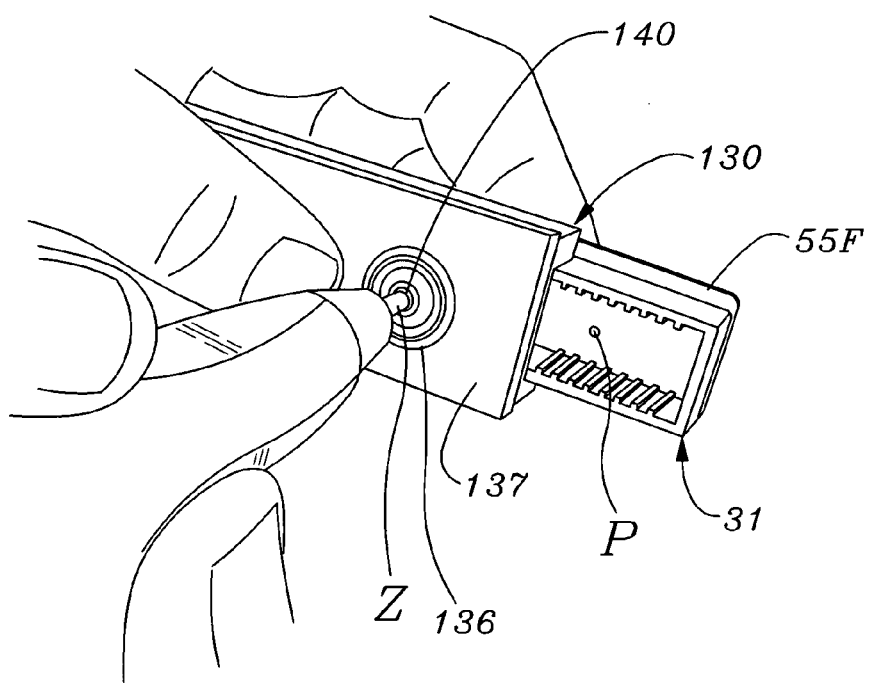
FIG. 25 is a perspective view showing how the drilling jig of FIGS. 22 and 23 is used to guide drilling of pin bores into the base of the dental model cast shown in FIGS. 23 and 24.
Figure 26:
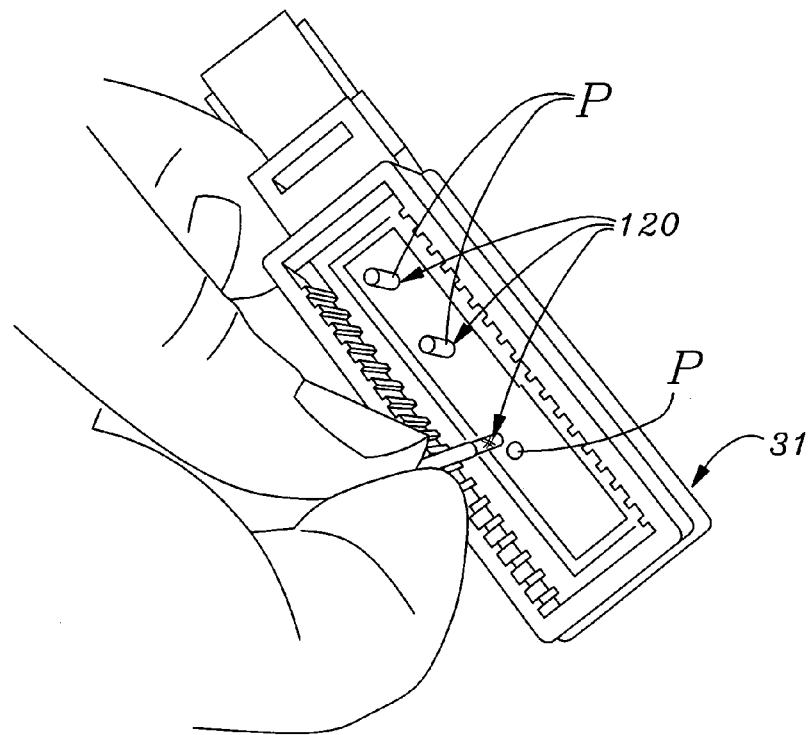
FIG. 26 illustrates one method for installing die segment pins in pin bores formed in the dental model cast as shown in FIG. 25.

As shown in FIGS. 24 and 25, drilling alignment fixture 130 is used by longitudinally sliding a cast J supported on ledges 135F, 135B of the fixture to thereby position a location of the cast where it is desired to insert a pin in longitudinal alignment with bushing bore index line 138. Drilling alignment fixture 130 and cast J are then rotated together as a unit to expose the lower surface 139 of the fixture, whereupon a drill bit is inserted through bore 140 of bushing 136, and rotated to drill a pin bore P at a desired location into the base M of cast J. Next, as shown in FIG. 26, pins 120 are inserted into and secured in pin bores P made as described above.

Figure 27:
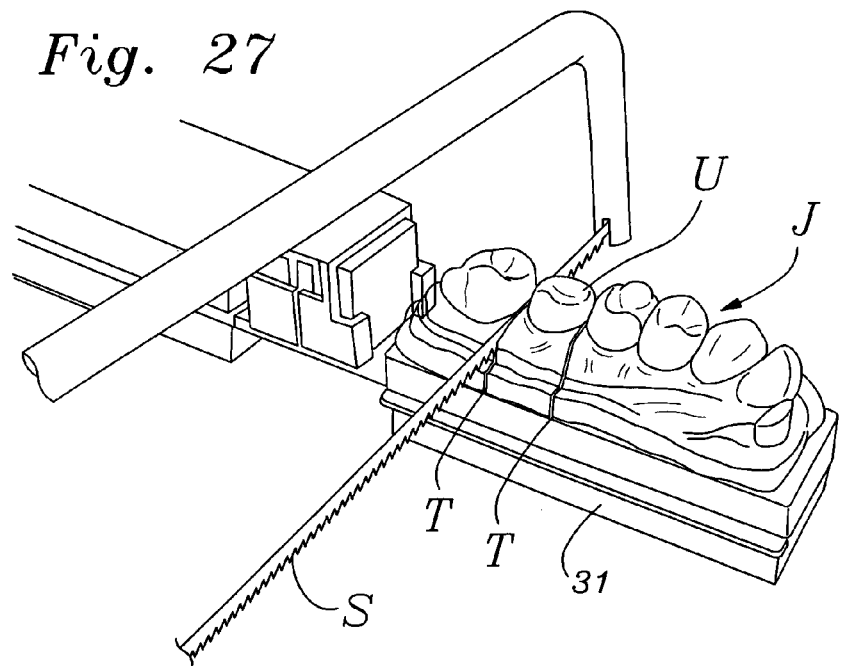
FIG. 27 illustrates one method for segmenting the dental model cast of FIGS. 25-26 into individual die segments.

As shown in FIG. 27, tray 31 containing cast J, is re-oriented to an upright position, and vertical saw cuts T are made into the cast to sever die segments from adjacent portions of the cast. Saw cuts T are made downwards just to the upper surface levels of front and back abutment flanges 55F, 55B. Cutting to the common level of the upper surface of the abutment flanges ensures that the saw cuts are made completely through the thickness of base M of cast J, thus enabling a pinned die segment U to be removed from tray 31, as shown in FIG. 18, and re-inserted into a precisely predetermined position relative to adjacent segments of the cast, which need not be removed, and repeatedly removed and re-inserted.

According to a first variation of the modified apparatus and method described above and illustrated in FIGS. 23-27, after pin bores P have been drilled into the base M of a cast J as shown in FIG. 25, the cast may be ejected from a tray 31, as for example, using a template 90 and knock-out tool as shown in FIG. 4. Then, pins 120 may be installed in the pin bores P of cast J in the manner indicated in FIG. 13, and the remaining steps of the basic embodiment of the method shown in FIGS. 13 through 15 and described above performed to produce a completed dental prostheses model. According to a second, slightly different variation of the modified apparatus and method depicted in FIGS. 23-27, pins 120 may be installed in bores P of cast J prior to ejecting the cast J from a tray 31, whereupon the steps of the basic embodiment depicted in FIGS. 16-18 and described above performed to produce a complete dental prostheses model.

Figure 28:
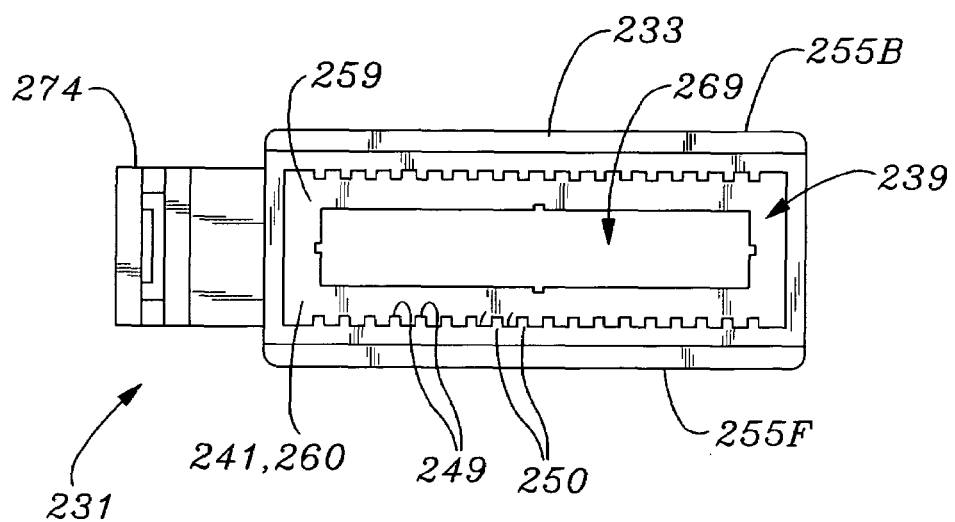
FIG. 28 is an upper plan view of a re-usable quadrant modeling tray for a pin tray dental prostheses modeling system according to the present invention.
Figure 29:
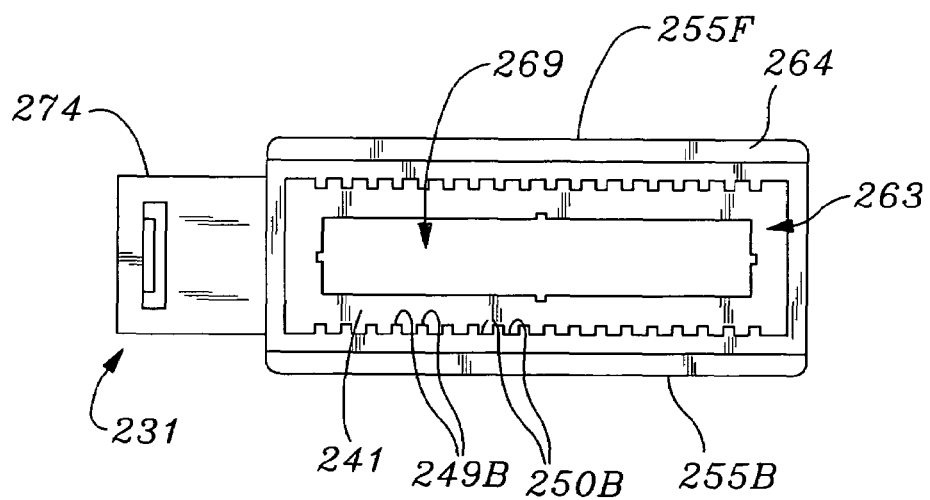
FIG. 29 is a lower plan view of the modeling tray of FIG. 27.

FIGS. 28 and 29 illustrate a re-usable modeling tray 231 for a pin-tray dental prostheses modeling system according to the present invention. Re-usable modeling tray 231 is substantially identical in structure and function to tray 31 described above, but does not have a break-away center panel 61 or frangible support members 65 therefor. Instead, as shown in FIGS. 28 and 29, molding tray 231 has a base plate or wall 242 which consists of a rectangular ring-shaped peripheral portion 260 that circumscribes a concentrically located rectangular-shaped aperture 269. Thus constructed, tray 231 can be fabricated as an injection molded plastic part, or by modifying a new or used tray 31 by removing a break-away center panel 61 from base wall 42 of the tray 31 by the method described above.

Figure 30:
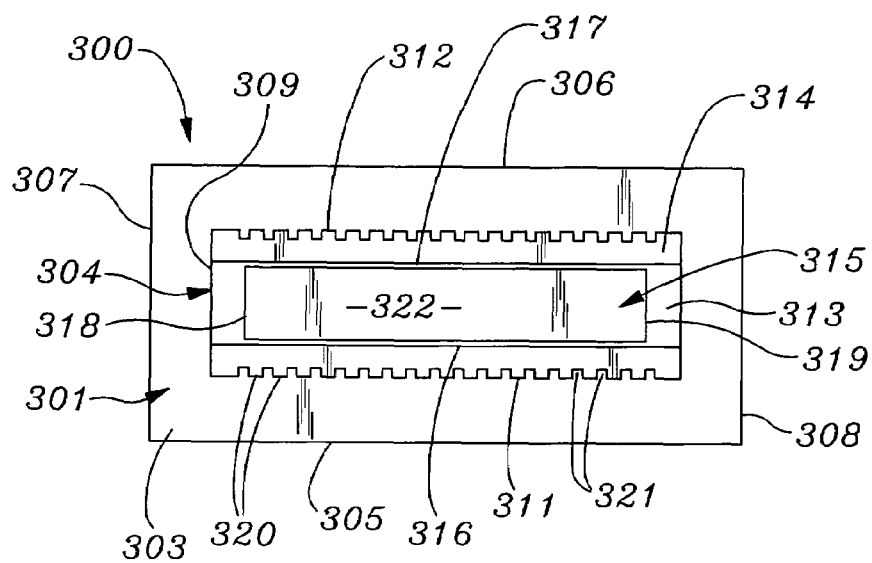
FIG. 30 is an upper plan view of a tray insert for use with the tray of FIGS. 28 and 29.
Figure 31:
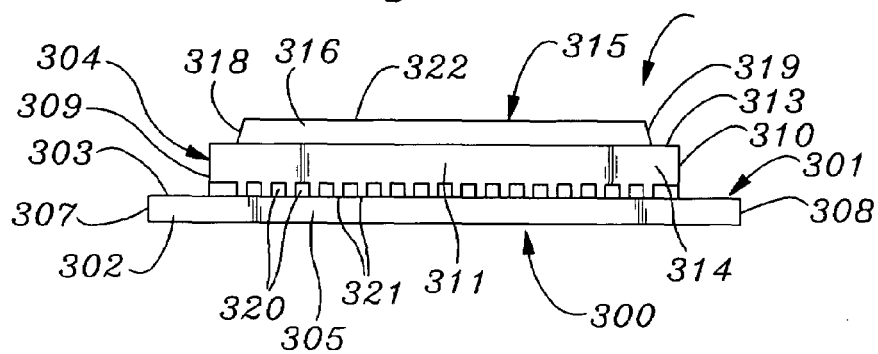
FIG. 31 is a front elevation view of the insert of FIG. 30, the rear elevation view being identical to the front elevation view.
Figure 32:
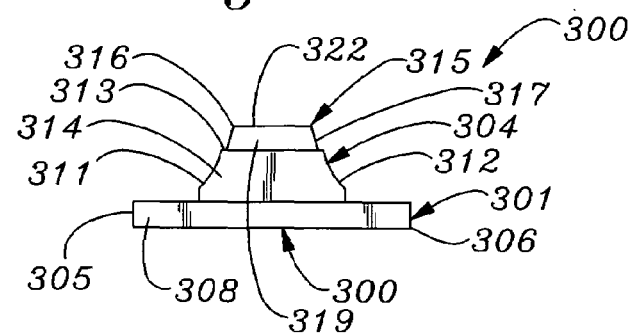
FIG. 32 is a right side elevation view of the insert of FIG. 31, the left side elevation view being identical to the right side elevation view.

FIGS. 30-32 illustrate an insert 300 for use with modeling tray 231 according to the present invention. As shown in FIGS. 30-32, insert 300 has a flat, longitudinally elongated, rectangular plan-view base plate 301. As shown in FIGS. 31 and 32, base plate 301 of insert 300 has a generally uniform thickness, and has flat and parallel lower and upper surfaces 302, 303, respectively. Referring to FIGS. 30-32, insert 300 may be seen to include a longitudinally elongated, rectangular plan view boss 304 which protrudes upwards from upper surface 303 of insert base plate, the boss being concentrically located with respect to front, rear, left and right perimeter wall surfaces 305, 306, 307 and 308, respectively, of the base plate 301. As shown in FIGS. 30 and 31, boss 304 of insert 300 has generally vertically disposed left and right side walls 309, 310, and front and rear side walls 311, 312, which are inclined towards a vertical, longitudinally disposed mid plane of the boss. As shown in FIGS. 31 and 32, boss 304 has protruding upwardly from an upper surface 313 of a trapezoidally transverse cross section base 314 thereof a longitudinally elongated rectangularly-shaped lug 315.

Lug 315 has front and rear longitudinally elongated, generally vertically disposed edge walls 316, 317 which protrude upwardly from front and rear angled boss walls 311, 312, respectively, of boss 304. Also, lug 315 has generally vertically disposed left and right side walls 318, 319, which protrude upwardly from upper surface 313 of boss base 314, and has a flat upper surface 322 parallel to base plate 301 of the insert. As shown in FIGS. 30 and 31, left and right side walls 318, 319 of lug 315 are recessed short equal distances from left and right sides 309, 310, respectively of base 314 of boss 304.

Referring to FIGS. 30 and 31, it may be seen that front and rear side walls 311, 312 of boss 304 of insert 300 optionally have formed in short, more generally vertically disposed lower portions thereof a plurality of alternating ribs 320 and grooves 321 which are adapted to mesh conformally with optional complementarily-shaped grooves 250B and ribs 249B, respectively, in lower well 263 of tray 231.

Figure 33:
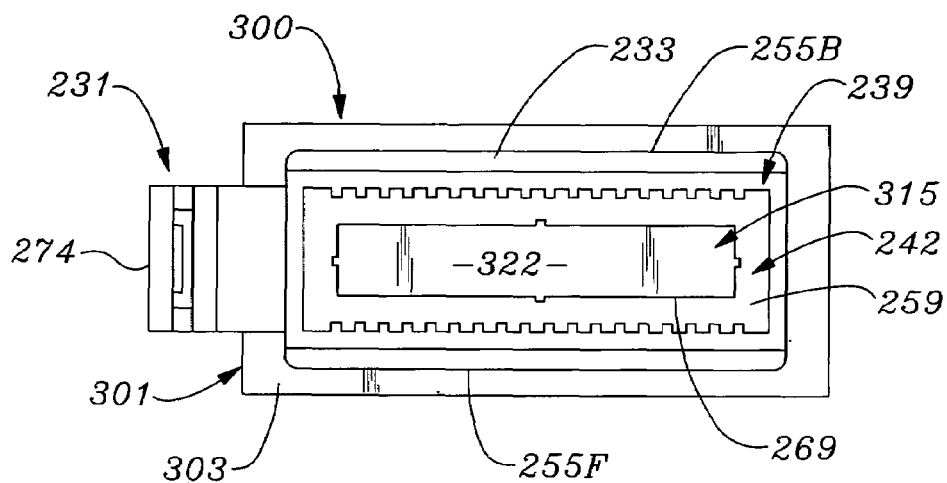
FIG. 33 is an upper plan view of the tray of FIG. 28, showing the insert of FIGS. 30-32 installed in the tray of FIGS. 28-29.
Figure 34:
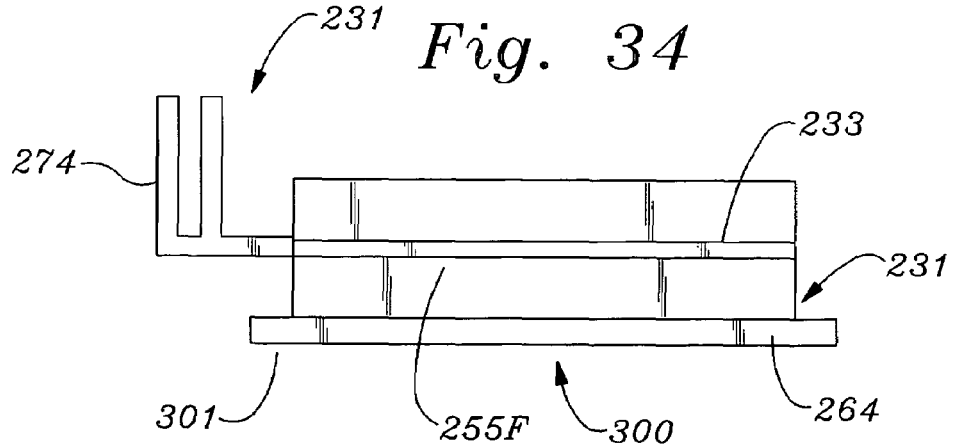
FIG. 34 is a front elevation view of the tray and installed insert of FIG. 32.

Referring now to FIGS. 33 and 34, it may be seen that insert 300, constructed as described above, is adapted to be fitted into lower well 263 of tray 231, with lug 315 fitting conformally within aperture 269 through base wall 242 of the tray. Thus positioned, upper surface 322 of insert lug 315 is substantially flush with upper surface 259 of base wall 242 of tray 231.

Figure 35:
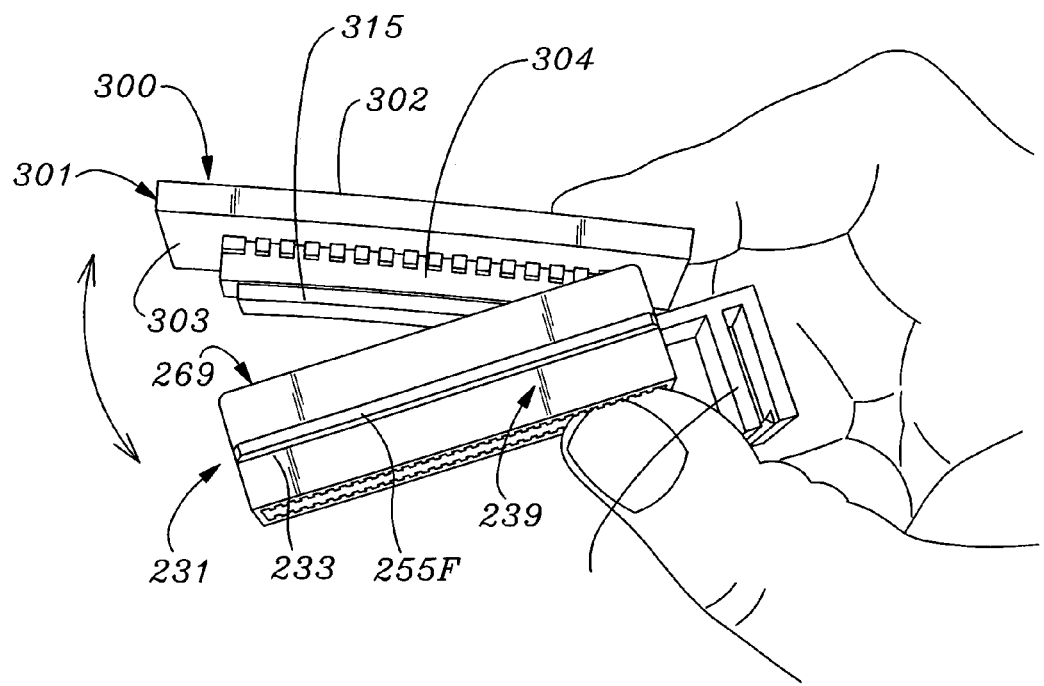
FIG. 35 is a front perspective view showing a method of removing the insert from the tray of FIG. 34.

In a preferred embodiment, tray insert 300 is made of a resilient material, e.g., an elastomeric polymer such as polyurethane. This choice of materials enables lug 315 to fit resiliently within aperture 269 through base wall 242 of tray 231 in a liquid tight seal therewith. Liquid die stone may then be poured into upper well 239 of tray 231 to form the base of a dental model cast, in the manner shown in FIGS. 4 and 11 and described above. After liquid die stone has hardened to form a cast, insert 300 is readily withdrawn from lower well 263 of tray 231, by grasping an edge of base plate 301 and exerting a downwardly directed parting force relative to the tray, as for example, by grasping an edge of the tray and an edge of the insert base plate between a thumb and forefinger and exerting a pinching force thereon, as shown in FIG. 35. Following removal of insert 300 from tray 231, a dental prostheses may be fabricated according to the steps shown in FIGS. 24-27 and described above, or according to the first or second variations described, which are also described above.

Figure 36:
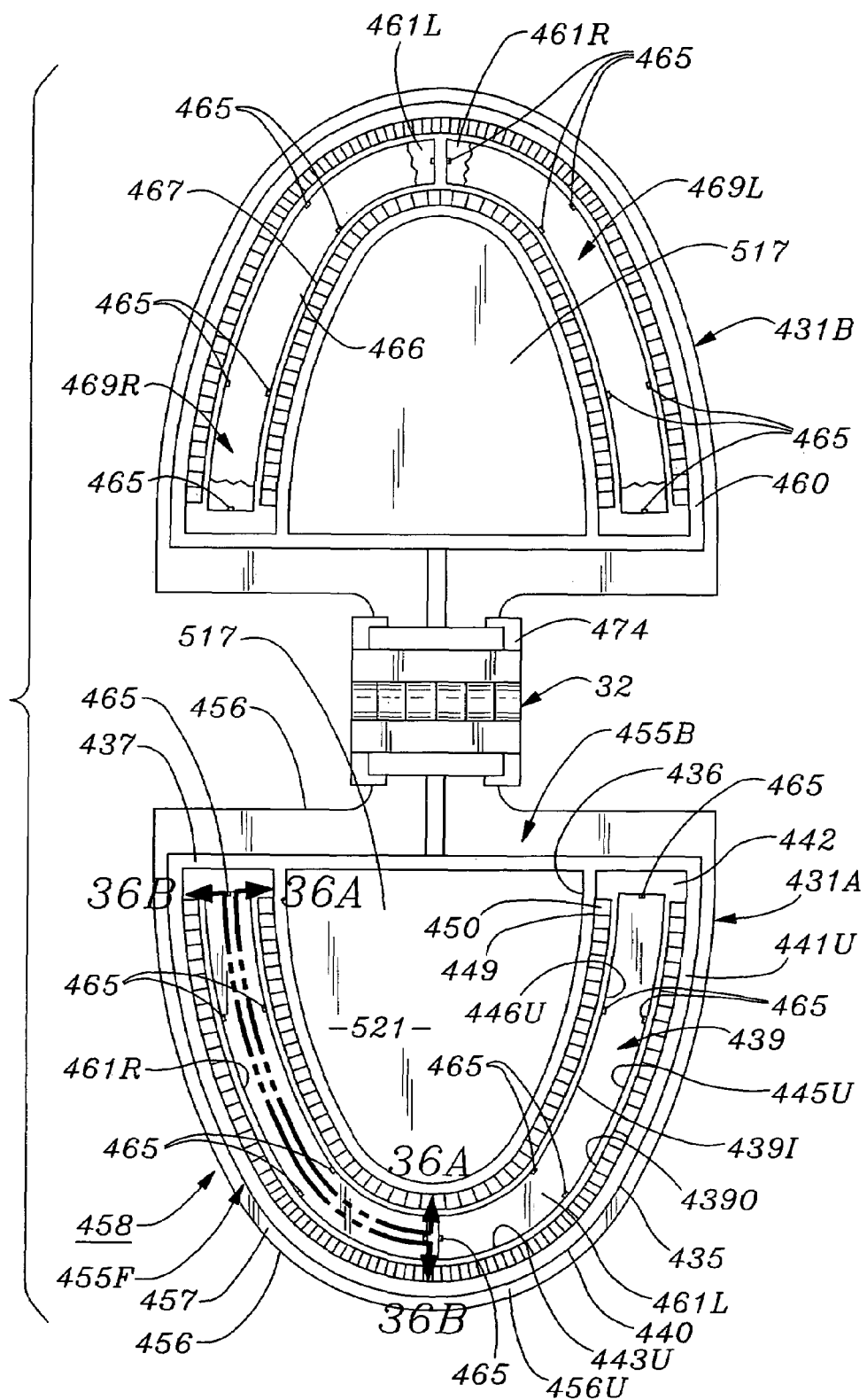
FIG. 36 is an upper plan view of a full-arch tray for a dental prostheses modeling system according to the present invention.
Figure 37:
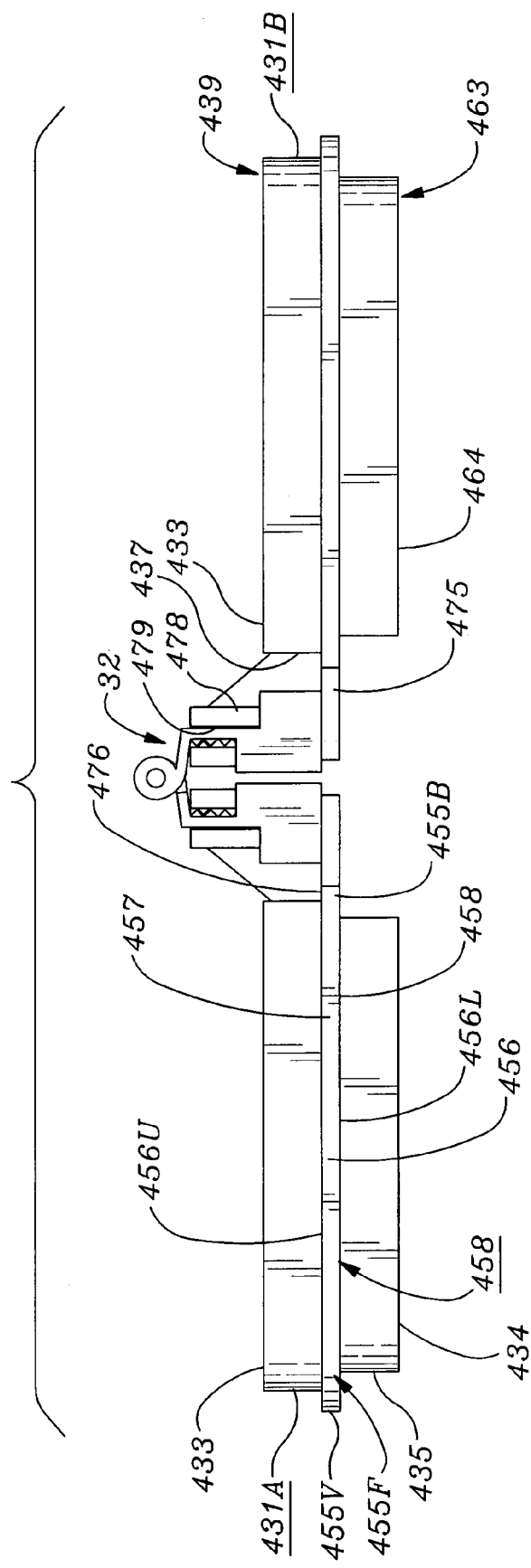
FIG. 37 is a side elevation view of a pair of trays of the type shown in FIG. 36, the trays being joined by a hinge coupler.
Figure 38:
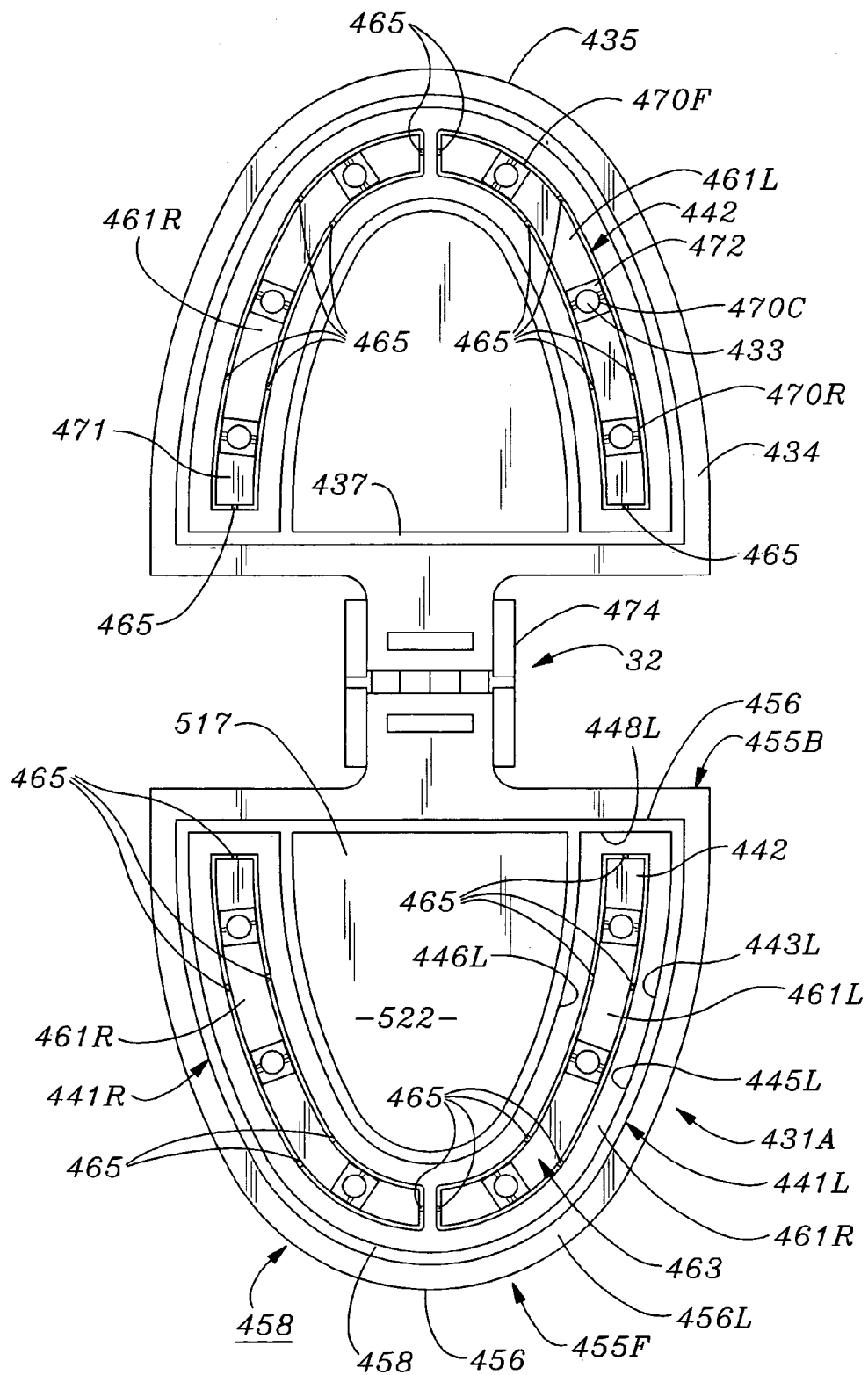
FIG. 38 is a lower plan view of the trays and coupler of FIG. 37.

FIGS. 36-38 illustrate full arch double-well modeling trays 431 according to the present invention. Modeling trays 431 are intended for use in making full-mouth, or full-arch upper and lower dental models of a patient's upper and lower jaws. The structure and function of modeling trays 431 are substantially analogous to those of quadrant double-well modeling tray 31 described above. The main difference between the quadrant and full-arch trays is that the quadrant tray has upper and lower wells which have in plan view the shape of an elongated rectangular box of constant width, while the full-arch tray has symmetric upper and lower wells which have in plan view the shape of an elongated, semi-elliptical arch-shaped strip of constant width. In the quadrant tray, the rectangular upper and lower wells are disposed between front and rear longitudinal walls, and shorter left and right transversely disposed walls. On the other hand, the elliptically arc-shaped upper and lower wells of the full-arch tray 431 are disposed between radially spaced apart, outer and inner parallel elliptically curved vertical walls, which both terminate at a transversely disposed diametrical wall that lies on the minor axis of an ellipse.

As shown in FIGS. 36-38, each tray 431 has in plan view the shape of a semi-ellipse, similar to that of a shoe heel. Tray 431 preferably has flat and parallel upper and lower surfaces 433, 434, respectively. Also, tray 431 has arcuately curved, elliptically arc-shaped, parallel, generally vertically disposed outer and inner walls 435, 436. Walls 435, 436 are spaced radially apart from one another at a constant radial distance, and perpendicularly intersect a straight, transversely disposed posterior end wall 437. Posterior end wall 437 is disposed transversely along a line corresponding to a minor axis of semi-elliptically-shaped tray 431, and has in a posterior elevation view a transversely elongated rectangular shape.

As shown in FIG. 36, full-arch tray 431 includes a thin, arcuately curved base plate or base wall panel 442 which is disposed parallel to and approximately equidistant from upper and lower surfaces 433, 434 of the tray. Base panel 442 has the shape of a semi-elliptically curved strip of constant width, and forms with the inner surfaces of adjacent vertical perimeter walls of the tray, in the upper part thereof, a relatively deep upper depression or well 439 which has in upper plan view the shape of semi-elliptical band or strip of constant radial width. As shown in FIG. 38, base plate 443 of tray 431 also forms in lower portion a lower well 463 which has a shape symmetric to that of upper well 439.

Upper and lower wells 439, 463 have inner and outer wall surfaces 439I, 439O, 463I, 463O, respectively, which are parallel to the outer vertically disposed perimeter wall surface 440 of the tray, and form therewith a thin arcuately-shaped upper and lower peripheral rings 441U, 441L, respectively, between the upper and lower wells 439, 463 and the outer vertical wall surface of tray 431. Peripheral rings 441U, 441L have disposed perpendicularly outwards from base wall 442 inner, generally vertically disposed, peripheral wall surfaces 443U, 443L which include anterior front, arcuately curved portions 445U, 445L, posterior rear, arcuately curved upper and lower vertical portions 446U, 446L, and posterior, straight vertical wall surfaces 448U, 448L.

As may be understood by referring to FIG. 37, upper and lower wells 439, 463 have approximately equal, relatively great depths, related to their cross-sectional area dimensions, i.e., about 9/32 inch deep for a well having an arc length of about 5 inches and a radial width of about 5/8 inch.

Figure 36A:
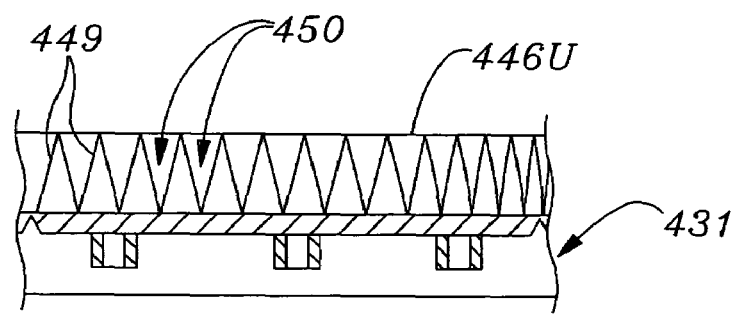
FIG. 36A is a radially inwardly directed vertical sectional view of a full-arch tray of FIG. 36, taken in the direction of curved line 36A-36A.
Figure 36B:
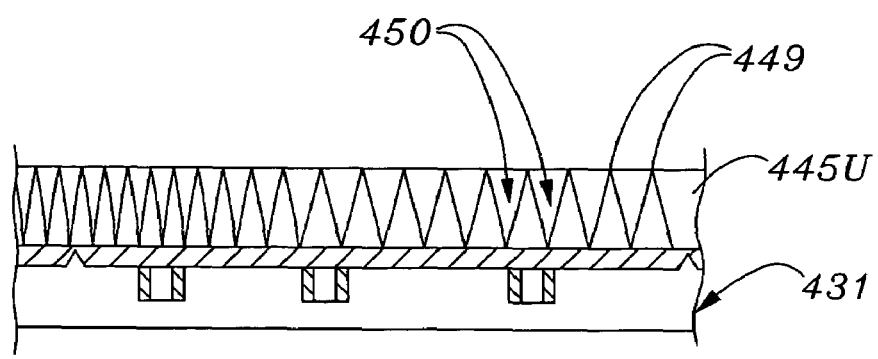
FIG. 36B is a curved, radially outwardly directed vertical sectional view of the full-arch tray of FIG. 36, taken in the direction of curved line 36B-36B.

Referring again to FIG. 36, front and rear inner wall surfaces 445U, 446U of upper peripheral ring 441U have formed therein a plurality of vertically disposed ribs 449 which protrude radially inwardly towards a longitudinal center line of upper well 439. Ribs 449 protrude vertically upwardly of base wall 442, and form between each adjacent pair of ribs a vertically disposed notch or groove 450. As may be seen best by referring to FIGS. 36A, 36B, ribs and grooves 449, 450, respectively, have in elevation view the shape of narrow, vertically disposed upright and inverted triangular, or wedge-shaped plates, respectively. As will be described in detail below, alternating ribs and grooves 449, 450 form complementary grooves and ribs in outer vertical surfaces of the base of a dental model cast which is formed in upper well 439 by solidified liquid die stone poured into the upper well, thus enabling the base and individual segments cut from the base, to be removably returned to exact pre-existing locations within tray 431, because of the indexing action of the ribs and grooves being insertably received within complementary-shaped grooves and ribs molded into the sides of the model cast by hardened liquid die stone. Moreover, since downwardly pointing wedge-shaped ribs are molded into the base of a dental model cast formed in tray 431, which have the shape of grooves 450 in the inner wall surfaces of the tray, when the dental model cast or die segments severed therefrom are re-inserted vertically downwardly into the tray, the wedge-shaped ribs protruding from the base or die segments wedge frictionally into the wedge-shaped grooves 450 between ribs 449 of the tray walls. That wedging action helps to secure individual die segments within tray 431 and prevent die segments from falling out when the tray is inverted.

Referring to FIGS. 36-38, it may be seen that tray 431 is provided with a semi-elliptically curved anterior abutment flange 455F, and a transversely disposed, straight posterior abutment flange 455B, which protrude outwardly from anterior and posterior walls 435, 436, respectively, of tray 431. As shown in the figures, each abutment flange 455F, 455B has the shape of a horizontally disposed, thin, longitudinally elongated rectangular cross-section rib or web which has an outer vertical wall surface 456 that is spaced outwards from an outer anterior or posterior wall of tray 431, and flat and parallel, horizontally disposed, upper and lower surfaces 456U, 456L, respectively. Anterior and posterior abutment flanges 455F, 455B, together form a unitary abutment flange 458 which encircles and is parallel to the outer vertical wall surfaces of tray 431. The function of anterior and posterior abutment flanges 455F, 455B are described below.

Referring to FIGS. 36 and 38, it may be seen that base wall 442 of upper well 439 in molding tray 431 has a flat upper surface 459, and includes an outer rectangular ring-shaped peripheral portion 60 formed of flanges which protrude perpendicularly inwards from the inner wall surfaces 445U, 446 of peripheral ring 441U of the of the tray. Base wall 442 also includes a pair of concentrically located, arcuately-shaped, arcuately spaced apart center knock-out or break-away panels 461L, 461R. Base wall 442 has a thickness of less than the height of tray 431, e.g., about 1/16 inch for a tray height of about 5/8 inch, and upper surface 459 of base wall 442 is located about 9/32 inch below upper peripheral edge wall 433 of the tray. Thus arranged, base wall 442 forms within upper and lower portions of tray 431 relatively deep, e.g., about 9/32 inch, symmetrically shaped upper and lower wells 439 and 463, respectively, which protrude inwardly from upper peripheral face 433 and lower peripheral face 464 of the tray, respectively, towards base wall 442.

As shown in FIGS. 36 and 38, it may be seen that center break-away panels 461 of tray base wall 442 are connected to outer rectangular ring-shaped portion 460 of the base wall by a plurality of readily breakable, or frangible members 465. Thus, as shown in FIG. 38, outer vertical wall surfaces 466 of base wall break-away center panels 461 are joined to inner vertical wall surfaces 467 of ring-shaped portions 460 of the base wall by a plurality of thin, breakable pins 465, e.g., a pair of anterior and posterior pins for each panel 461R, 461L. In a preferred embodiment, tray 431 is fabricated as a unitary molded plastic part, with outer surface 466 of break-away center panels 461 angled downwardly and inwardly away from adjacent inner wall surfaces 467 of ring-shaped outer portions 460 of base wall 442. With this construction, pins 465 may be readily molded to have a thickness substantially less than that of break-away center panels 461, thus enabling the pins to be readily broken and thereby permitting the center panels to be readily broken away and removed from tray 431. With break-away center panels 461 thus removed from tray 431, base wall 442 of the tray has through its thickness dimension a pair of arcuately elongated, constant width aperture 469R, 469L. The apertures have shapes approximating that of a pair of quadrant sectors of an ellipse which are disposed arcuately forward from posterior transverse end wall 437, and have longitudinally disposed front end walls which are spaced circumferentially apart on opposite sides of a thin web 469C.

As shown in FIG. 38, center break-away panels 461 of tray base wall 442 preferably are provided with one or more bosses 470 which protrude perpendicularly downwards from the lower surface 471 of each panel. Although the exact shape and size of bosses 470 is not critical, each panel 461 of the embodiment of tray 431 shown in FIG. 38 has protruding downwardly therefrom three square cross-section bosses 470 which each have a flat lower surface 472 and a blind circular bore 473 which extends perpendicularly upwards from the lower surface. The three bosses 470 include a longitudinally centrally located center boss 470C, and front and rear bosses 470F, 470R spaced equal longitudinal distances away from the center boss. The function and purpose of bosses 470 is described below.

Referring to FIGS. 36-38, it may be seen that each tray 431 has protruding horizontally outwards from posterior transverse end wall 437 thereof a hinge coupler bracket 474 for releasable attachment to hinge mechanism 342. Each hinge coupler bracket 474 has a shape approximating that of an L-bracket, an upright leg of which is bifurcated into two spaced apart, parallel plates. Thus, as shown in FIGS. 36-38, hinge coupler bracket 474 includes a rectangularly-shaped base plate 475 which protrudes outwardly from end wall 437 of tray 431. Base plate 475 has horizontally disposed upper and lower surfaces 476, 477 which are parallel to upper surface 433 of tray 431. Upper surface 476 of bracket base plate 475 is preferably recessed below upper surface 433 of the perimeter edge wall of tray 431, and has protruding perpendicularly upwards therefrom a first, outer rectangularly-shaped upright leg plate 478. Outer upright leg plate 478 has an outer vertical surface 479 which is co-planar with outer vertical edge wall 480 of a base plate 475.

Bracket 474 includes a second, inner upright leg plate 481 which is shaped similarly to outer leg plate 478, and which protrudes perpendicularly upwards from base plate 475 at a location spaced longitudinally inwardly from the outer upright leg plate. Inner upright leg plate 481 has an outer vertical wall surface 482 which is spaced longitudinally inwards of and parallel to an inner vertical wall surface 483 of outer leg plate 478. Preferably, a rectangularly-shaped aperture 484 is formed through base plate 475 of bracket 474, between outer and inner upright leg plates 478, 481. The purpose of aperture 484 is to facilitate elastic flexure of the outer and inner leg plates away from and towards one another, thereby facilitating elastic gripping engagement of hinge mechanism 432, has been described above for use of hinge mechanism 32 with quadrant trays 31.

Figure 39:
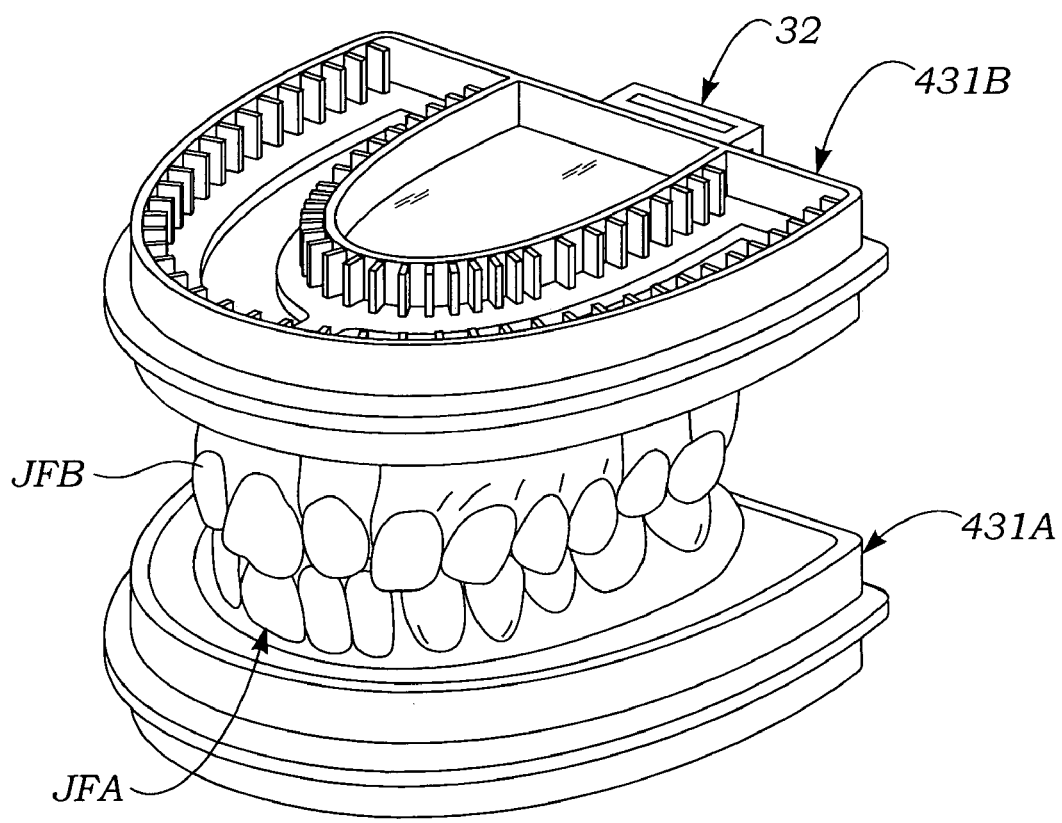
FIG. 39 is a perspective view showing completed master and opposing dental casts formed in the trays of FIGS. 37 and 38, and showing the trays and casts pivoted on the hinge coupler to comprise an articulated, full-mouth dental model.

A pair of full arch dental modeling trays 431A, 431B is used to make master and opposing full-arch dental models of teeth in a patient's upper and lower jaws, in a method exactly analogous to that employed to make master and opposing quadrant models using a pair of trays 31A and 31B. That method is depicted in FIGS. 4-8 and described in detail above, and therefore is not repeated here. FIG. 39 shows completed full-arch master and opposing dental model casts made using a pair of trays 431A, 431B as shown in FIGS. 36-38, by the method described above, and shows the casts fastened to pivotable hinge coupler 32 to comprise an articulated full-mouth dental model.

A preferred method for removing a master full-arch dental model cast JF from a tray 431A consists essentially of exerting upwardly directed forces on break-away center panels 461 of base wall 442 of the tray which are of sufficient strength to break pins 65 which join the center panels to peripheral ring 460 of the base wall, and then pushing upwardly on that portion of the lower surface MF of a cast JF that is accessible through apertures 469 through the base wall. According to a preferred method of removing cast JF from tray 431A, an anvil template 490 and knock-out tool 491, as shown in FIGS. 40A, 40B 41, are employed.

As shown in FIGS. 40A and 41, template 490 includes a flat base 492 which has an outline shape similar to the plan view shape of a tray 431, but of a larger size. Thus, base 492 of template 490 has in plan view the shape of a semi-ellipse, similar to that of a shoe heel and that of tray 431, but having a semi-major and semi-minor axes each about 3/4 inch larger than those of the semi-elliptically-shaped perimeter of abutment flange walls 455F, 455B of the tray. Base 492 of template 490 has protruding upwardly from a flat upper surface 493 thereof a semi-elliptically curved peripheral flange wall 494 which has a vertically disposed outer wall surface 495 coextensive with the outer perimeter wall surface of the template, and an inner wall surface 496 which is parallel to the outer wall surface and spaced radially inwardly thereof by about ⅜ inch. Peripheral flange wall 494 has a flat upper surface 497 and includes an arcuately curved anterior portion 498 and a straight, transversely disposed posterior end portion 499 which coincides with a minor axis of the semi-elliptically shaped base. Posterior end portion 499 of peripheral flange wall 494 has formed therein a centrally located, rectangularly-shaped notch 500 which protrudes downwardly from upper surface 497 of the flange wall, the notch terminating at upper surface 493 of the template base. As shown in FIG. 41, notch 500 provides clearance for a hinge coupler arm bracket 474 which protrudes rearwardly from a full-arch tray 431.

As shown in FIG. 40A, flange wall 494 of full-arch knock-out template 490 also is provided with one or more notches which are spaced circumferentially apart from hinge coupler notch 500, to provide convenient access for receiving a person's thumb or finger to facilitate grasping and removing a tray 431 seated on template 490 as shown in FIG. 41. Thus, as shown in FIG. 40, upper surface 497 of flange wall 494 has protruding downwardly therefrom three rectangular cross-section notches, including an anterior notch 501 centered on a major axis of the elliptical template base, and a pair of notches 502A, 502B spaced equidistant from either side of the anterior notch. Preferably, notches 501, 502A and 502B terminate at lower ends thereof in flat surfaces 503, 504A and 504B which are co-planar, parallel to, and spaced above upper surface 493 of template base 492.

As shown in FIG. 40A, base 492 of full-arch knock-out template is provided with a pair of arcuately curved, rectangular cross-section ribs 505A, 505B which are spaced transversely apart equidistant from a longitudinal center line of the base coincident with its major axis, and which protrude perpendicularly upwards from upper surface 493 of the base. The outer vertical surfaces 506A, 506B of ribs 505A, 505B are parallel to inner wall surfaces 507A, 507B of flange wall 494, and form therebetween a semi-elliptically curved, sector-shaped channel 507C of a generally constant radial width which is slightly larger than radial span distance between outer surfaces of outer and inner semi-elliptically curved walls 435, 436 of tray 431.

As shown in FIGS. 40A and 41, template base 492 has a semi-elliptically shaped recess 508 of the proper size and shape to vertically insertably receive in a conformal loose fit the lower peripheral flange wall 441L which protrudes downwardly from centrally located abutment flange 455 of a full-arch tray 431. Moreover, ribs 505A, 505B protruding upwardly from upper surface 403 of template base 492 are of an appropriate height and location to abut the lower surfaces of break-away center panels 461, or bosses which protrude downwardly from panels which are so constructed, when a tray 431 is placed conformally within the recess 508 in the upper portion of template base 492.

Referring to FIGS. 40B and 41, it may be seen that full-arch knock-out tool 491 has a tabular upper portion 509 which has a heel-like planar shape similar to that of knock-out template 490, and four downwardly depending generally square cross-section legs, including a centrally located anterior leg 510, a centrally located posterior leg 511, and a pair of posterior corner legs 512A, 512B transversely aligned with the central posterior leg.

FIG. 41 illustrates the manner of using full-arch anvil template 490 and full-arch knock-out tool 491 to remove a full-arch dental model cast JF from tray 431. As shown in FIG. 41, tray 431 (See FIG. 38) containing cast JF is placed in recess 508 in the upper surface of template base 492, with bottom surfaces 471 of the break-away base panels 461L, 461R of the tray, or the bottom surfaces 472 of optional bosses 470 protruding downwardly from break-away base panels 461L, 461R of the tray, supported on upper surfaces 513A, 513B of ribs 505A, 505B. Knock-out tool 491 is then positioned above tray 431, with the lower surface 514 of anterior tool leg 510 resting on the upper surface of the vertex of anterior flange 455, the lower surfaces 515A, 515B of posterior corner legs 512A, 512B contacting upper surfaces of opposite sides of anterior flange 455, and the lower surface 516 of central posterior tool leg 511 contacting the upper surface of a semi-elliptically shaped web section 517 of the tray 431 which is located between inner facing wall surfaces of the tray and which has upper and lower surfaces 521, 522, which are co-planar with upper and lower surfaces of the abutment flanges, respectively. A sharp blow is then delivered to the flat upper surface 523 of knock-out tool 491, causing the knock-out tool legs to exert downwardly directed forces on tray abutment flange 455 and rear web 517. This force in turn causes the upper surfaces of ribs 505A, 505B to exert upwardly directed forces on break-away center panels 461A, 461B of tray base wall 442, thereby breaking pins 465 which join the center panels to rectangular ring-shaped portion 460 of the base wall, and thence ejecting cast JF upwardly and out from the tray.

FIGS. 42A 42B and 43 illustrate the structure and function of a full-arch sawing fixture 520 according to the present invention. As shown in FIGS. 42A and 42B, full-arch sawing fixture 520 includes a flat base 522 which has in plan view an outline shape and size similar to those of a tray 431. Thus, base 522 of sawing fixture 520 has in plan view the shape of a semi-elliptically shaped plate similar to that of a shoe heel and that of tray 431.

Base 522 of sawing fixture 520 has protruding upwardly from a flat upper surface 523 thereof a relatively thick, semi-elliptical ring-shaped table 524 which has a flat upper surface 525 parallel to upper surface 523 of the base, and a vertically disposed semi-elliptically shaped anterior wall surface 526 which is parallel to and recessed radially inwardly of semi-elliptically curved anterior wall surface 527 of the base, thus forming at a junction therewithin a similarly curved, thin base flange wall 528 which protrudes radially outwardly from the table.

Table 524 of sawing fixture 520 has a flat, vertical posterior transverse end face 529 which coincides with the rear wall surface 530 of base 522 and a minor axis of the elliptical plan view thereof. Also, table 524 has protruding vertically downwardly from upper surface 525 of the table to upper surface 523 of base 522 a deeply relieved cut-out 531 which has the shape of a semi-elliptical cylinder, the vertically disposed surface of which is parallel to and spaced radially inwardly of outer surface 532 of the table. A lower portion of cut-out 531 is bordered by a thin, short rectangular-shaped end wall 533 which has an upper edge wall 534 located between and parallel to upper wall surface 525 of table 524, and upper surface 523 of base 522.

Referring still to FIG. 42, it may be seen that upper surface 525 of table 524 has formed therein a generally radially disposed horizontal saw groove 535 which penetrates inner vertical wall surface 536 and outer vertical wall surface 532 of the table. Saw groove 535 is located approximately midway between rear transverse wall 529 and anterior vertex 538 of table 524, and preferably has a curved, U-shaped transverse section. Sawing fixture 520 also includes a dental model retainer post 539 which protrudes perpendicularly upwards from upper surface 525 of table 524, on a posterior side of groove 535. Retainer post 539 is preferably located near inner vertical wall surface 536 of table 524 rearward of saw groove 535, and may have a square or other suitable cross-sectional shape.

Sawing fixture 520 also includes a thin, vertically disposed arcuately curved dental model retainer flange plate 541 which protrudes perpendicularly upwards from upper surface 525 of table 524. Flange plate 541 protrudes arcuately forward from posterior transverse end face 529 of fixture 520, to a location rearward of anterior vertex 538 of table 524. Also, flange plate 541 has an outer arcuately curved wall surface 543 which is coextensive with outer wall surface 532 of table 524, and an inner curved side surface 545 which is parallel to outer wall surface 543, and a horizontally disposed, arcuately curved upper wall surface 546. Groove 535 penetrates flange plate 541, and inner wall surface 545 of the flange plate preferably has formed therein alternating vertically disposed ribs and grooves 547, 548, respectively, which are shaped complementary to ribs and grooves formed in a dental model cast by ribs and grooves 449 and 450 of tray 431.

FIG. 43 illustrates the manner of using full-arch sawing fixture 520. As shown in FIG. 43, a full-arch, upper or lower dental model cast JF is placed downwardly on upper surface 525 of fixture table 524, with the lingual and labial sides of the model adjacent to retainer post 539 and retainer flange plate 541, respectively, with a selected portion of the cast corresponding to a first side of an intended die segment positioned above saw groove 535, whereupon a first of a pair of severing saw cuts is made vertically through the dental model cast by a saw blade S. The two parts of the dental model cast which have been severed from one another are then withdrawn vertically upwards from table 524, moved circumferentially with respect to saw groove 535 to position a second side of the intended die segment above the saw groove, and moved downwardly onto upper surface 525 of the table, between retainer post 539 and retainer flange plate 541, whereupon a second of a pair of saw cuts required to severe a die segment from adjacent portions of the dental model cast is made. In this way, any number of die segments are conveniently severable from dental model cast JF, help to using sawing fixture 520.

It should be noted that interlocking action of ribs 547 and grooves 548 in inner surface 545 of retainer flange plate 541 with complementary shaped grooves and ribs on the base of dental model cast JF help to secure the cast in place on table 524 of sawing fixture 520 as severing saw cuts are made through the cast. Also, it should be noted that the novel asymmetric geometry of full-arch sawing fixture 520 enables any part of a full-arch dental model cast JF to be positioned for segmenting above sawing groove 535, by positioning the dental model in a forward direction with the anterior portion of the cast facing in the same direction as vertex 538 of table 524 as shown in solid lines in FIG. 43, or in a reverse facing direction as indicated by phantom lines in FIG. 43.

Figure 44A:
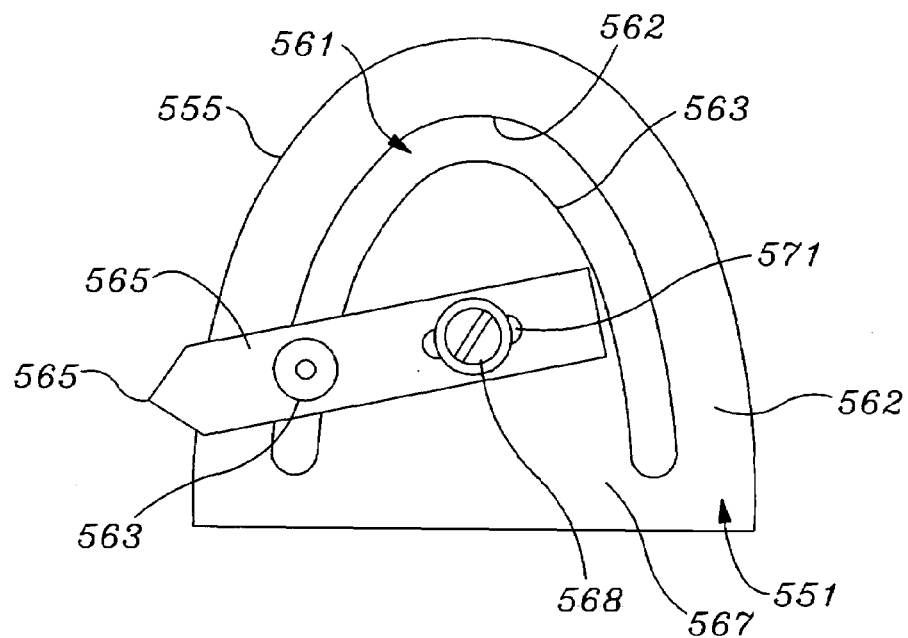
FIGS. 44A, 44B, 44C are lower plan views of a drilling alignment fixture for full-arch dental model casts according to the present invention, showing an index arm of the fixture at three different orbital locations.
Figure 44B:
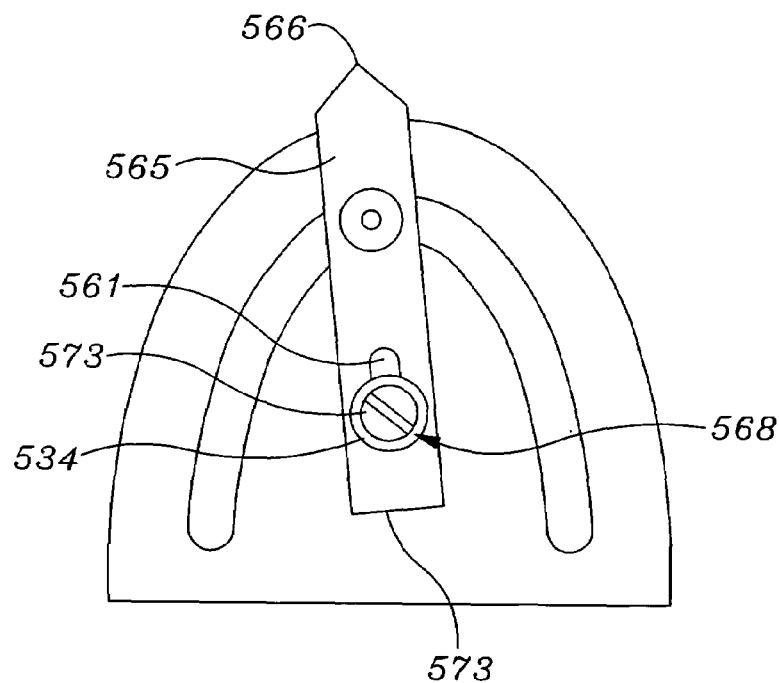
Figure 44C:
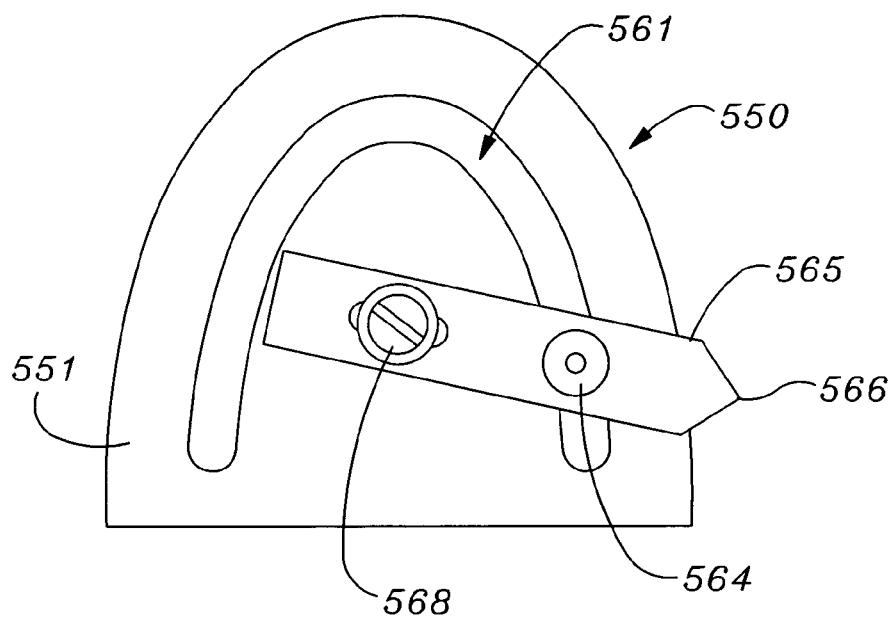

FIGS. 44A-44C illustrate a drilling alignment fixture 550 for full-arch dental model casts according to the present invention. As shown in FIGS. 44-49, full-arch drilling alignment fixture 550 has a semi-elliptical plan-view shape and includes a semi-elliptically shaped base plate 551 that has a flat bottom surface 552 and a flat upper surface 553 which is parallel to the lower surface. Base plate 551 of drilling alignment fixture 550 has protruding upwardly from flat upper surface 553 thereof a semi-elliptically shaped curved peripheral flange wall 554 which has a vertically disposed outer wall surface 555 coextensive with the outer perimeter wall surface of the fixture, and an inner wall surface 556 which is parallel to the outer wall surface and spaced radially inwardly thereof. Peripheral flange wall 554 has a flat upper surface 557 and includes an arcuately curved anterior portion 558 and a straight, transversely disposed posterior end portion 559 which coincides with a minor axis of the semi-elliptically shaped base. Posterior end portion 559 of peripheral flange wall 554 has formed therein a centrally located, rectangularly-shaped notch 560 which protrudes downwardly from upper surface 557 of the flange wall, the notch terminating at upper surface 553 of base plate 551 of fixture 550. Notch 560 provides a clearance for a hinge coupler arm bracket 474 which protrudes rearwardly from a full-arch tray 431.

Figure 45:
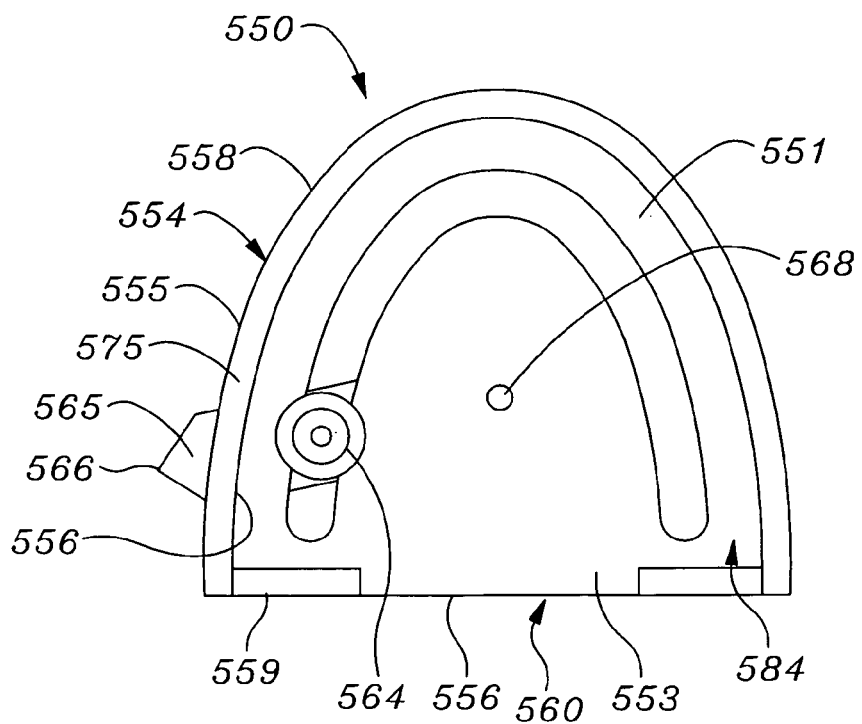
FIG. 45 is an upper plan-view of the drilling alignment fixture of FIG. 44.
Figure 48:
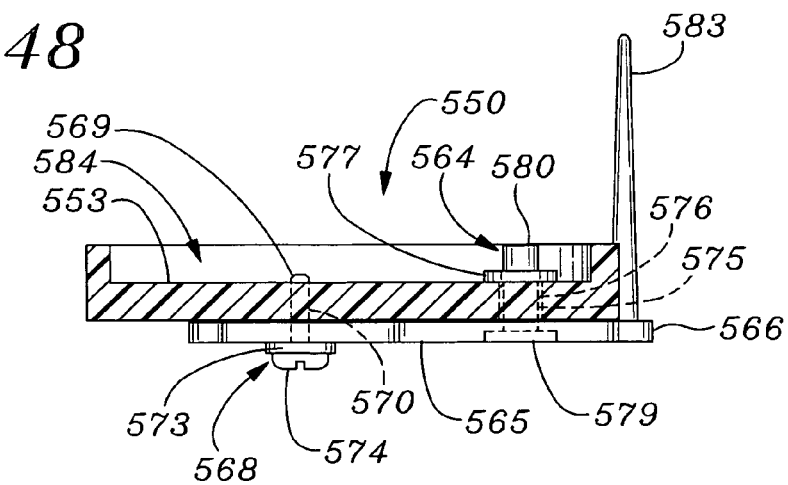
FIG. 48 is a vertical sectional view of the drilling alignment fixture of FIG. 46, taken in the direction of line 48-48.

As shown in FIGS. 44, 45 and 48, base plate 551 of full-arch drilling alignment fixture 550 has through its thickness dimension an elongated aperture 561 which has in plan view the shape of a thin, semi-elliptically shaped sector or band which has an outer vertical wall surface 562 which is parallel to and spaced radially inwardly of outer semi-elliptically curved wall surface 555 of the fixture, and an inner vertical wall surface 563 which is parallel to and spaced radially inwardly of the outer wall surface of the aperture. Semi-elliptical sector-shaped aperture 561 through base plate 551 of drilling alignment fixture 550 serves as a guide track for an elliptically orbitally adjustable drill guide bushing 564, as will now be described.

Referring to FIGS. 44-48, it may be seen that full-arch drilling alignment fixture includes a thin, flat index arm 565 which has a generally longitudinally elongated rectangular plan view shape, and a symmetrically pointed end 566 which protrudes radially outwardly of curved outer perimeter wall surface 555 of the fixture. Index arm 565 is pivotably mounted parallel to lower wall surface 552 of drilling alignment fixture base plate 551 by means of a screw 568 which has a shank 569 threaded into a bore 570 through the base, at a location near a focus of the semi-elliptically shaped base plate. Shank 569 is disposed vertically through a longitudinally elongated, rectangularly shaped aperture slot 571 provided through the thickness dimension of index arm 565. Slot 571 is located on a longitudinal center line of index arm 565, spaced inwardly of a rear transverse edge wall 572 of the index arm. Index arm 565 is retained parallel to and pivotally movable with respect to lower surface 552 of drilling fixture base plate 551 by a washer 573 positioned on shank 569 of screw 568, below the slotted head 574 of the screw.

Figure 46:
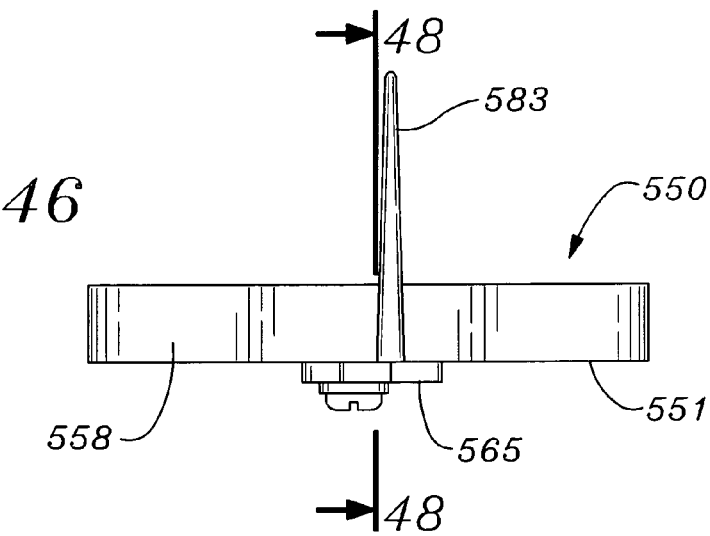
FIG. 46 is a front elevation view of the drilling alignment fixture of FIG. 44.
Figure 47:
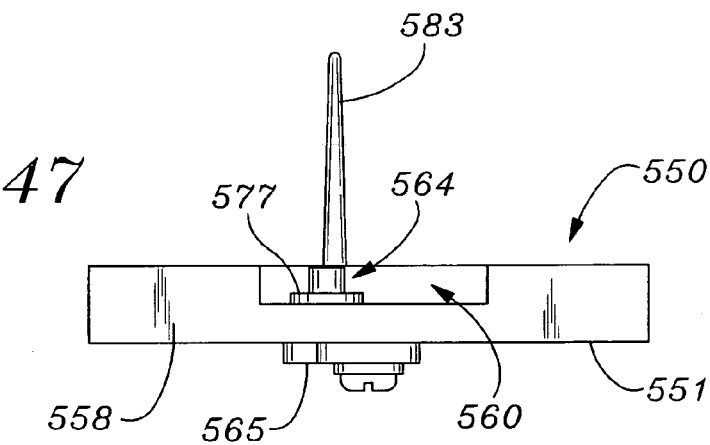
FIG. 47 is a rear elevation view of the drilling alignment fixture of FIG. 44.

Referring to FIGS. 44, 45, and 48, it may be seen that drill guide bushing 564 has a generally cylindrical shape including a lower cylindrical portion 575 which is fastened within a bore 576 provided through index arm 565, radially inwardly from pointed end 566 of the index arm. Drill bit guide bushing 564 also has an annular ring-shaped flange 577 which protrudes radially outwardly from cylindrical body 578 of the bushing, at a longitudinal location between lower end wall 579 and upper end wall 580 of the bushing. Flange 577 has a lower face which is slidable on upper surface 553 of drilling alignment fixture 550. Thus constructed, index arm 565 is pivotable about the axis of screw 568 to pointed end 566 of the index arm in vertical alignment with any selected circumferential location around the periphery of fixture base plate 551. Referring to FIG. 46, it may be seen that index arm 565 is optionally and preferably fitted with a pointer index pin or gnomon 583 which protrudes perpendicularly upwards from index arm 565, near tip 566 thereof.

As shown in FIG. 45, upstanding peripheral flange wall 554 of full-arch drilling alignment fixture 550 forms with base plate 551 a semi-elliptically shaped cylindrical cavity 584 which is of the proper size and shape to vertically insertably receive in a conformal fit the lower ring-shaped peripheral wall 441L which protrudes downwardly from centrally located abutment flange 455 of a full-arch tray 431.

Figure 49:
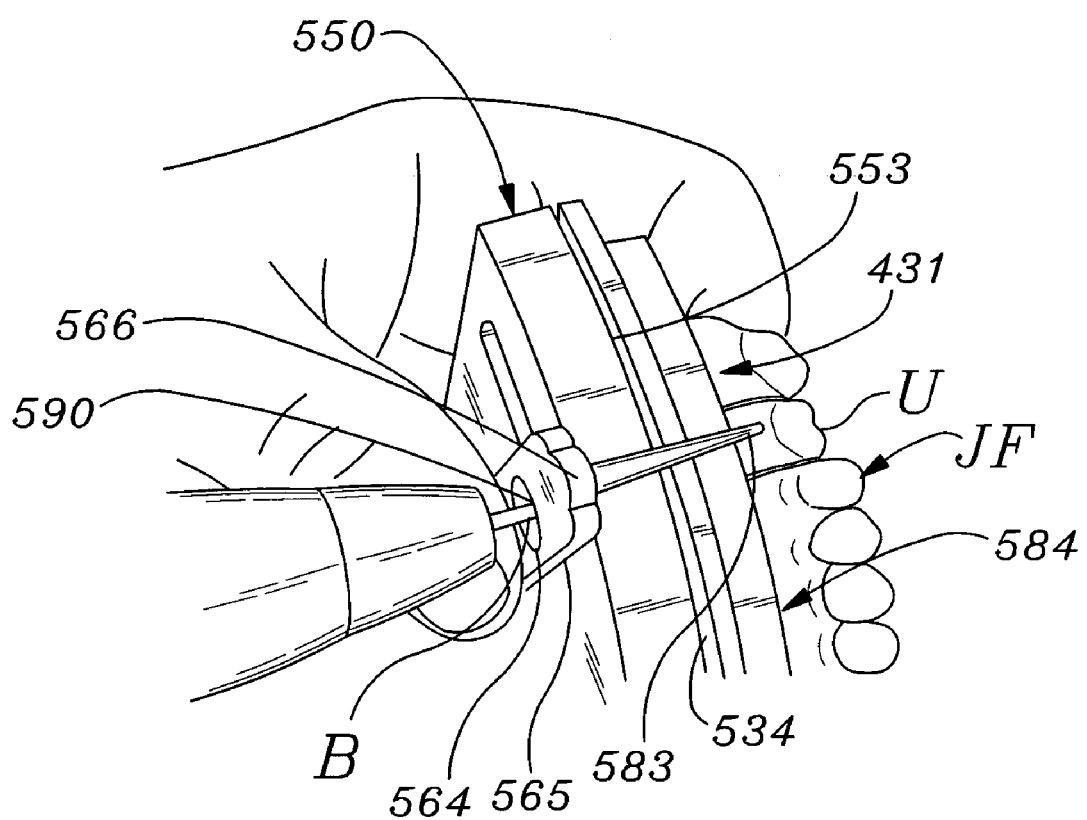
FIG. 49 is a right side perspective view showing the drilling alignment fixture of FIG. 46 in use to facilitate drilling a pin bore into the base of a die segment of a full-arch dental model cast.

FIG. 49 illustrates the manner of using full-arch drilling alignment fixture 550. As shown in FIG. 49, a full-arch tray 431 containing a full-arch cast JF from which one or more die segments U have been severed from remaining portions of the cast inserted downwardly into cavity 584 of drilling alignment fixture 550, the bottom surface 434 of the tray resting on upper surface 553 of the drilling alignment fixture base plate. Then, index arm 565 is grasped and pivoted orbitally about the axis of pivot screw shank 569 to position tip 566 and gnomon 583 of the index arm in circumferential alignment with a die segment U which is to have a pin bore drilled into the base thereof for receiving a manipulating pin. Fixture 550 and tray 530 are then inverted, and a drill bit or dental burr B is inserted upwardly into bore 590 of drill bit guide bushing 564, into contact with lower surface N of a die segment U. Drill bit B is then rotated by an electric drill to form a blind pin bore P which protrudes inwardly into die segment U from its lower surface. In an alternate method of aligning index arm 565 for drilling a pin bore into a die segment, the die segment is removed from tray 531, and index arm 565 is orbited to a position in which drill bit guide bushing 564 is visually centered below a segment of tray aperture 469 exposed by removal of the die segment. The die segment is then re-inserted into the tray cavity, fixture 550 containing tray 531 is inverted, and a pin bore drilled in the base of the die segment in the manner described above.

FIGS. 50A-50L illustrate a heavy-duty, 3-D articulator mechanism 600 of a type used in dental laboratories and clinics, and a prior art method of attaching a pair of full-arch dental model casts JF to the articulator mechanism. The 3-D articulator is used for checking proper occlusions of the biting contact areas of dental prostheses fabricated in the laboratory and which are to be used for reconstruction or replacement of one or more defective or missing teeth modeled by the casts.

Figure 50A:
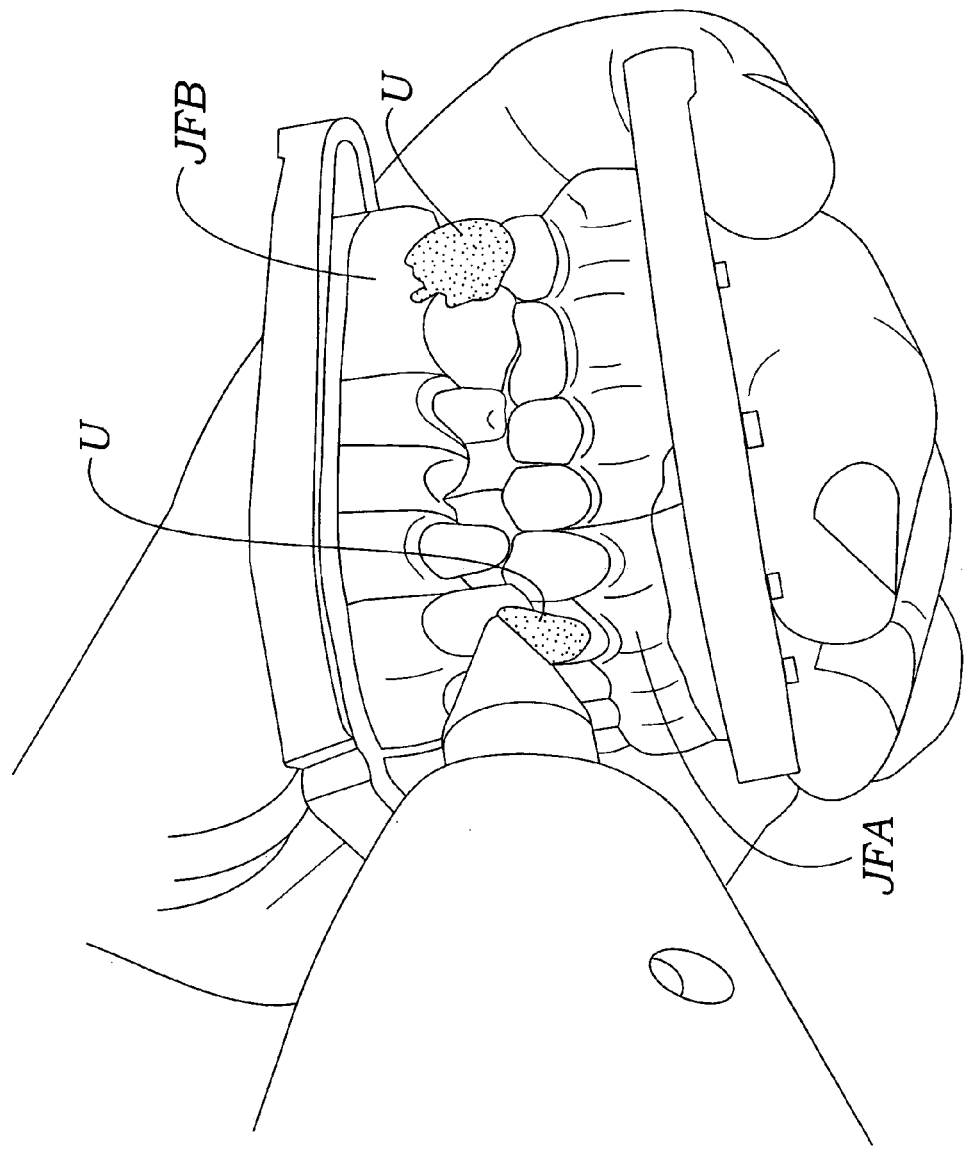

As shown in FIGS. 50A-50L, a typical prior art method of attaching a pair of full-arch lower and upper dental model casts JFA, JFB to lower arm 601 and upper arm 602 of articulator 600 includes, as shown in FIG. 50A, a first step which includes positioning the arches in proper occlusal relationship to one another and temporarily fastening the arches together in that relationship by applying blobs of hot wax U to several contacting regions of the arches, and allowing the wax to cool and harden.

Figure 50B:
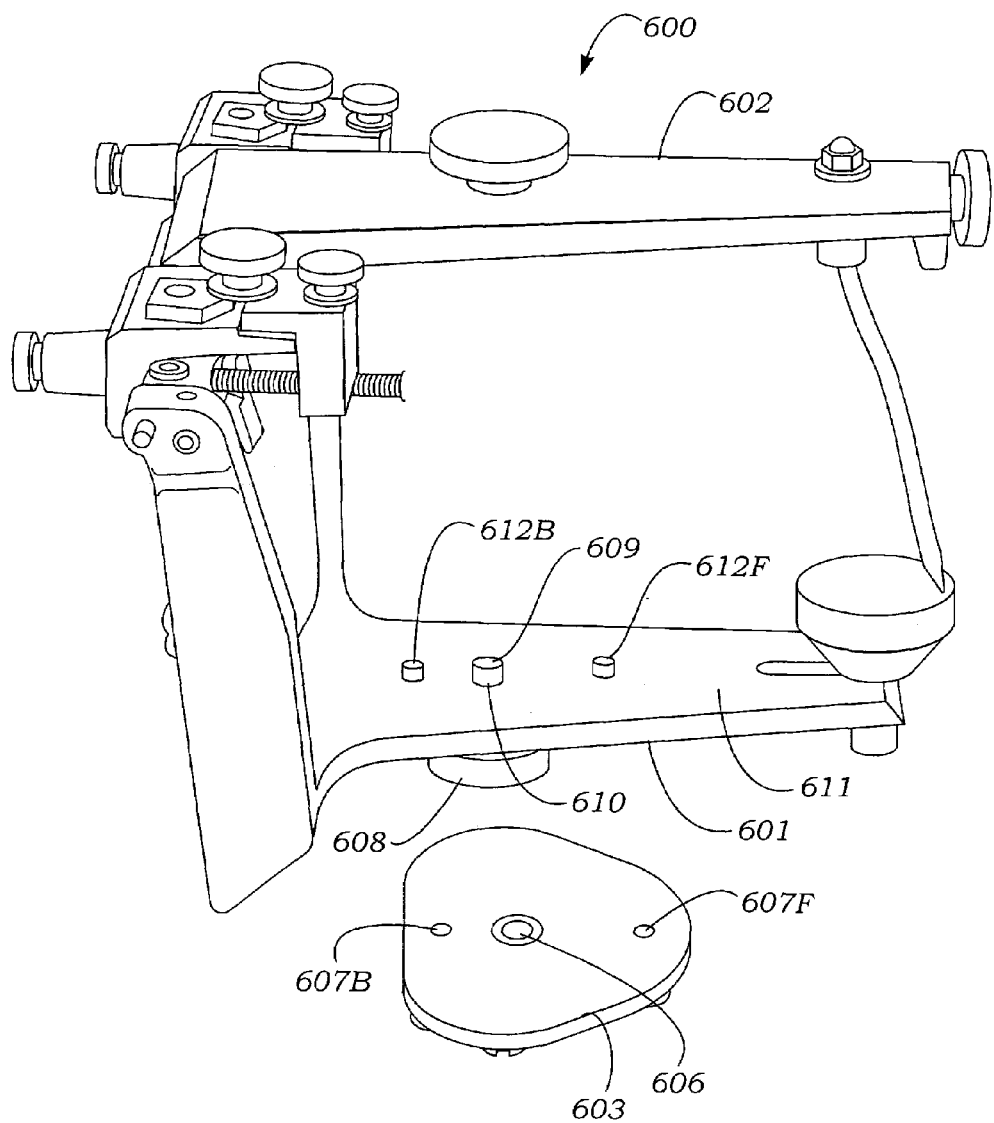
Figure 50D:
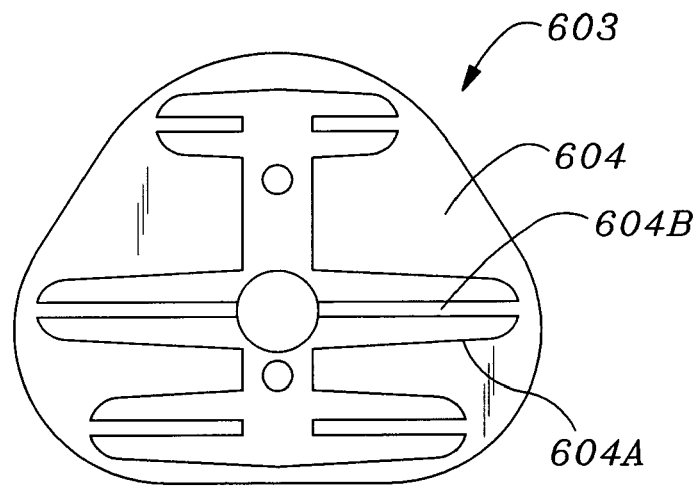
Figure 50C:
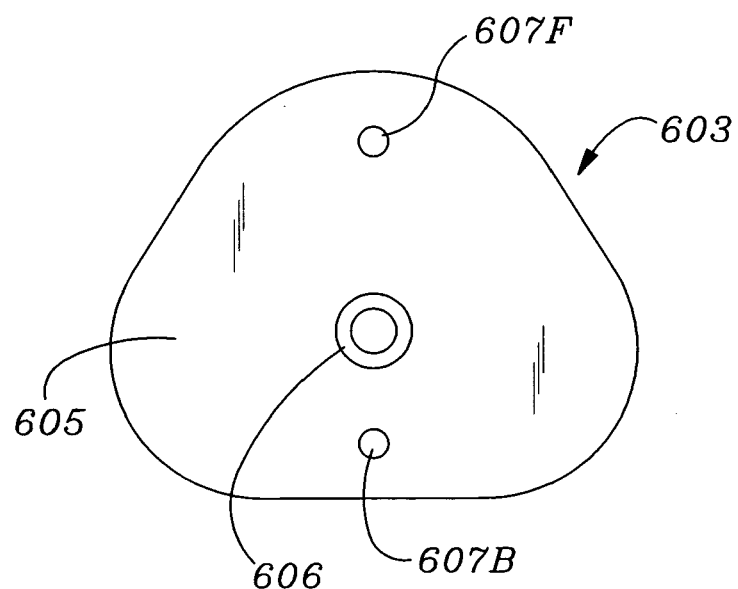
Figure 50E:
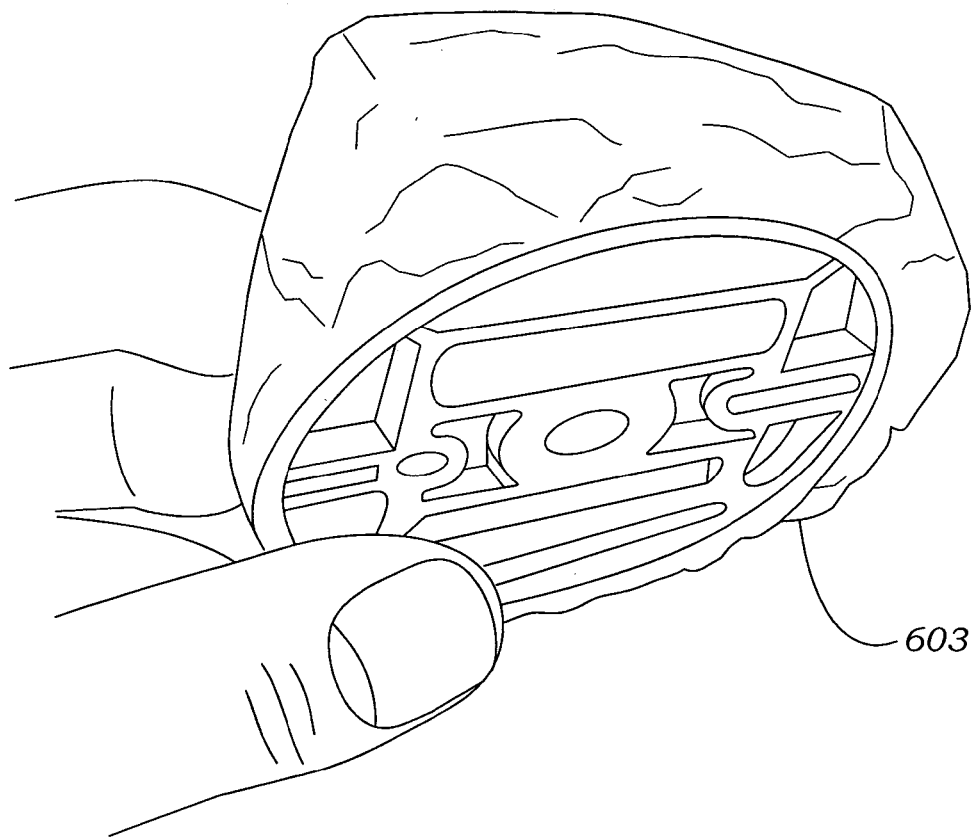

A second step in a prior art method of attaching arches JFA, JFB to articulator 600 consists of attaching a plastic mounting plate 603 to lower arm 601. As shown in FIGS. 50C, 50D, mounting plate 603 has a flat upper surface 604 which has protruding upwardly therefrom a plurality of intersecting ribs and grooves 604A, 604B arranged in a rectangular grid, and a parallel lower surface 605 into which perpendicularly protrudes a flush-mounted internally threaded bushing 606 and a pair of longitudinally aligned front and rear blind locating bores 607F, 607B located on opposite sides of the bushing. Mounting plate 603 is removably attachable to lower arm 601 of articulator 600 by means of a thumbscrew 608' which has a threaded shank 609 that protrudes upwardly through a hole 610 through the lower articulator arm, and which is threadably tightenable into bushing 606 of plate 603. As shown in FIG. 50B, thumbscrew hole 610 is generally centrally located in lower articulator arm 601, and arm 601 has protruding upwards from upper surface 611 thereof a pair of longitudinally aligned front and rear locating pins 612F, 612B which are adapted to be insertably received in blind locating bores 607F, 607B, respectively, of plastic mounting plate 603, thus securing the mounting plate in a pre-determined, irrotatable position on upper surface 611 of the articulator arm, when thumbscrew 608 is tightened into threaded bushing 606.

Figure 50F:
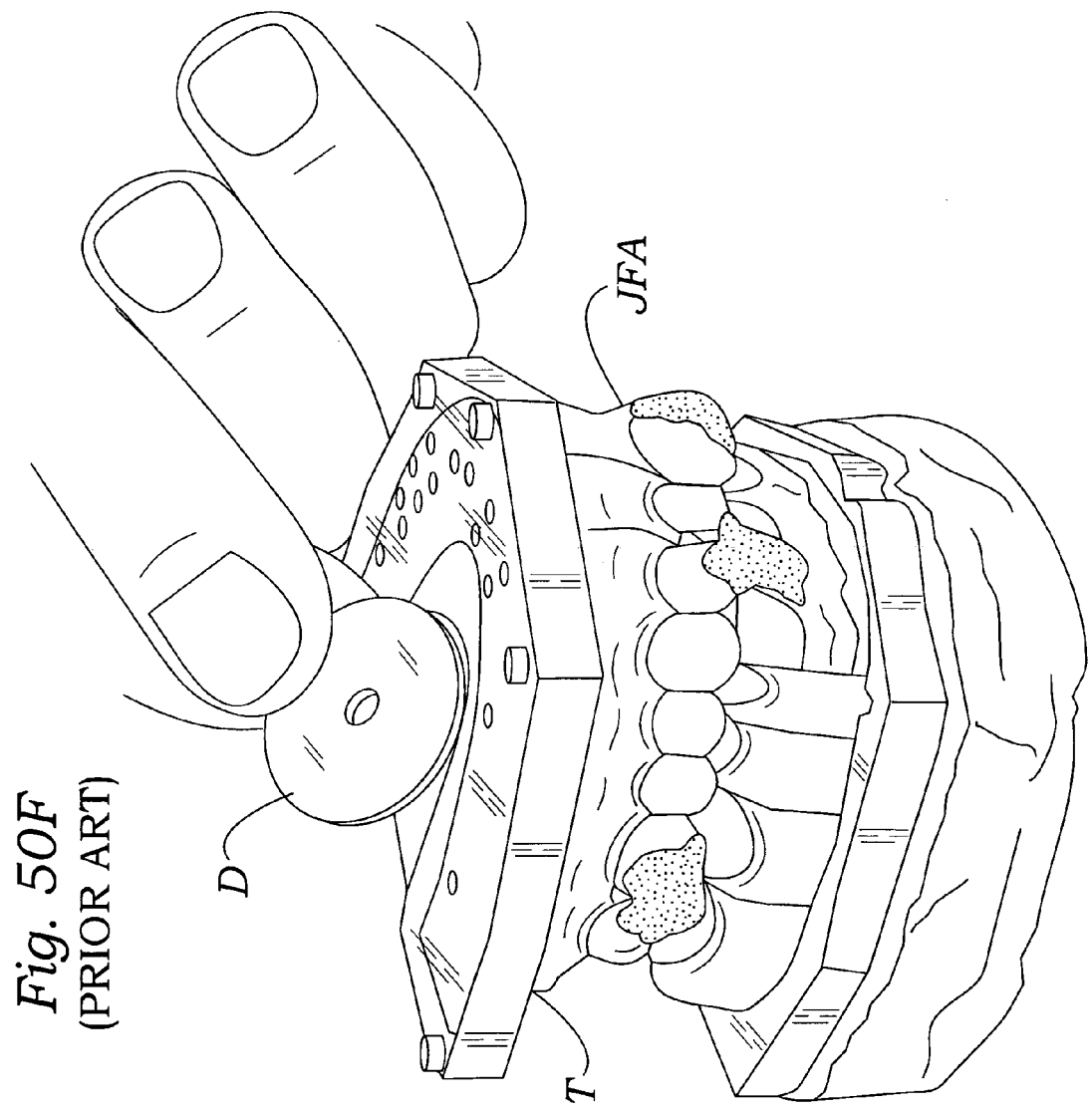

As shown in FIG. 50F, a third step in attaching a lower full-arch dental model cast to lower articulator arm 601 consists of applying a relatively thick layer of semi-liquid, viscous liquid die stone to the upper surface of mounting plate 603.

Figure 50G:
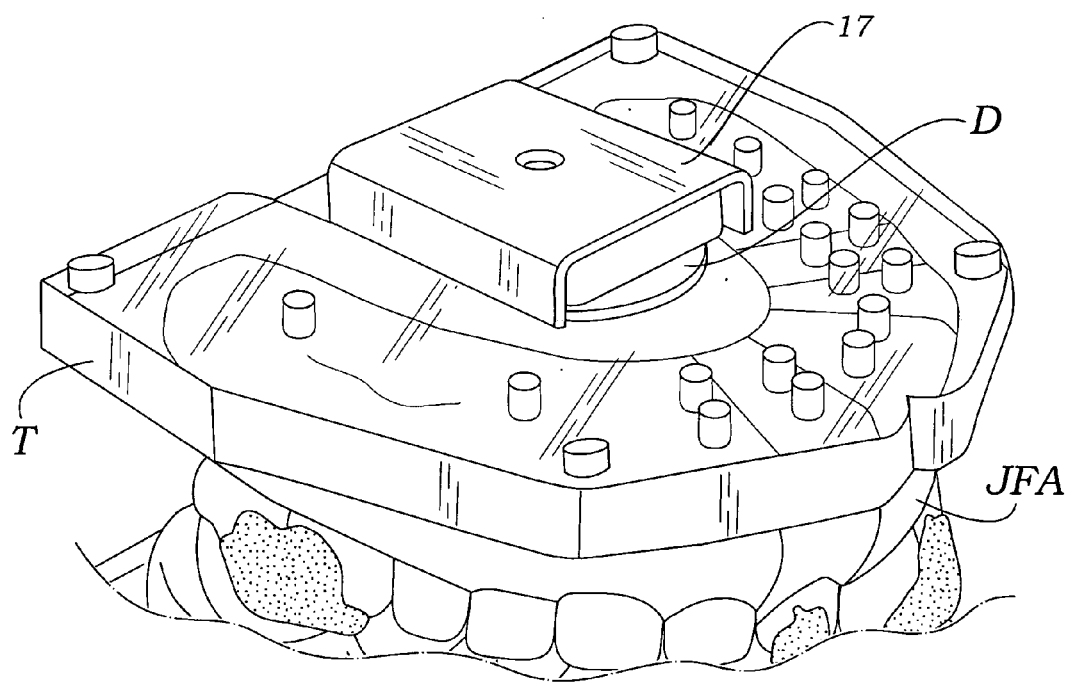
Figure 50H:
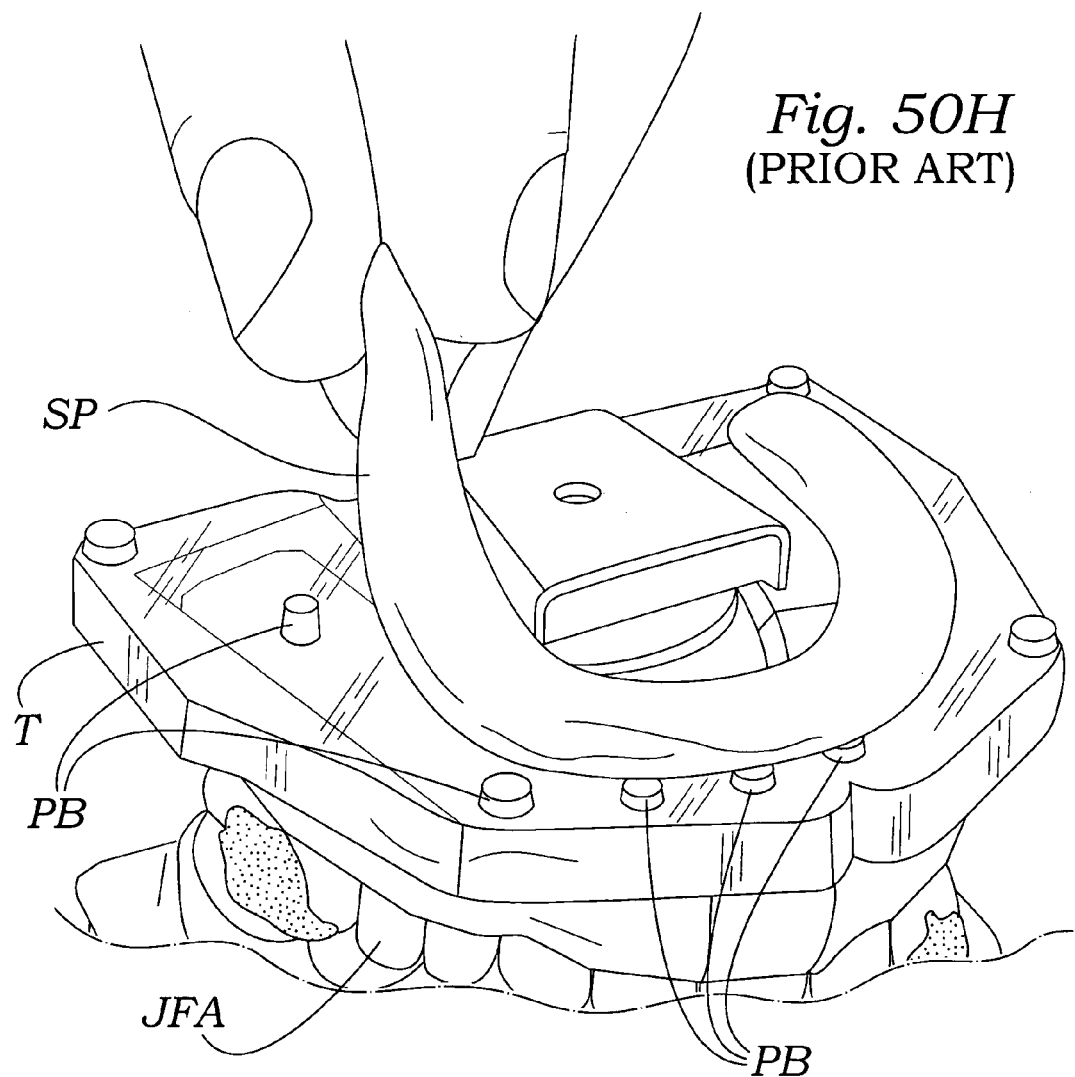
Figure 50J:
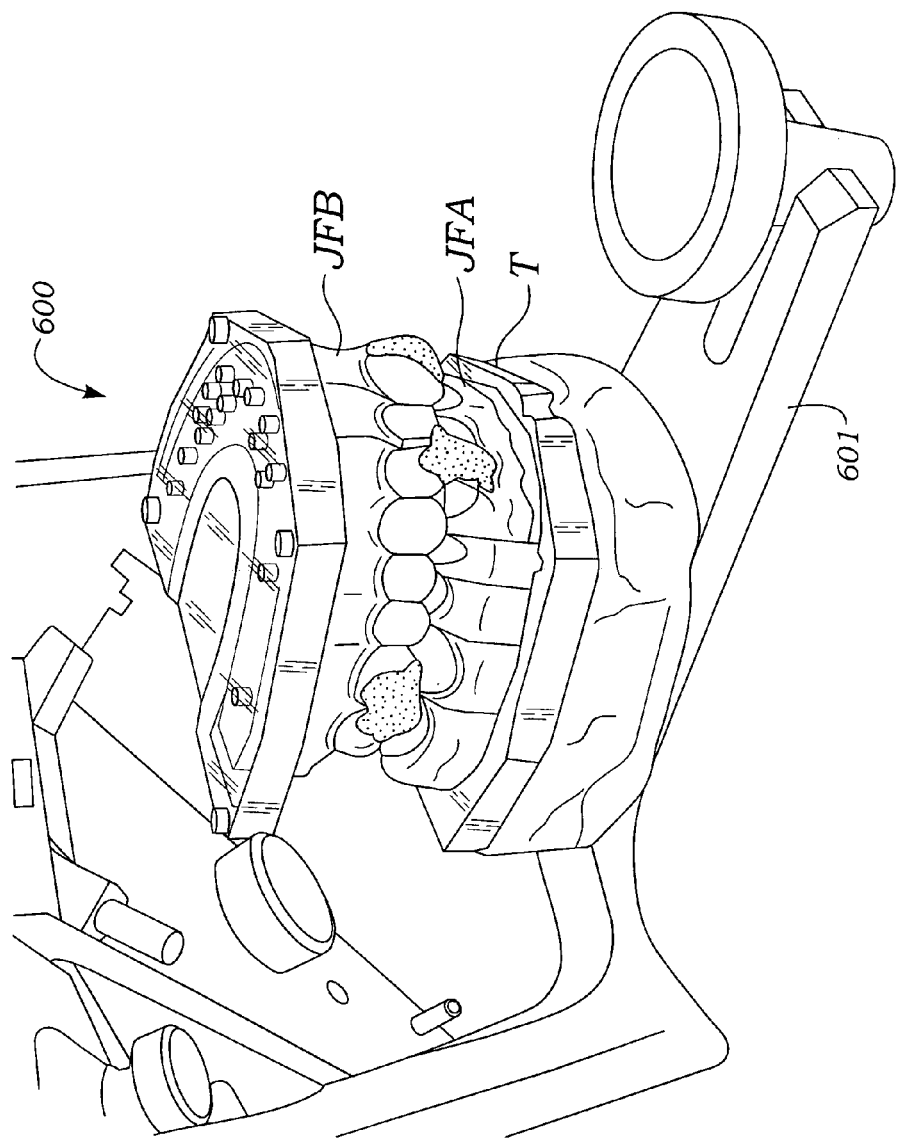

A fourth step in fastening a lower full-arch dental model cast JFA to lower articulator arm 601 consists of applying a layer of viscous semi-liquid die stone to a lower surface of a tray T holding the cast. If it is desired to provide a capability for repeatedly removing and replacing the arch from the articulator, a flat disk D made of a magnetized or unmagnetized ferromagnetic material is attached to the lower surface of tray T, as shown in FIG. 50F. A pot magnet M is then magnetically attached to an outer surface of magnetic disk D, as shown in FIG. 50G. Next, as shown in FIG. 50H, a strip of non-adhesive material such as silicone putty SP is secured to the lower surface of tray T, forming an arcuately curved shield or dam which covers pin bores PB provided through the tray for receiving die-manipulating pins, thereby preventing liquid die stone from entering the pin bores. As shown in FIG. 50J, plastic mounting plate 603 is attached to lower articulator arm 601. Liquid die stone is then applied in a thick layer over the entire lower surface of tray T, the tray is inverted, pressing liquid die stone thereof into semi-liquid die stone applied to the upper surface of base plate 603, whereupon the two die stone layers cohere and, time is allowed for the cohered die stone layers to harden into a unitary mass, as shown in FIG. 50J.

Figure 50K:
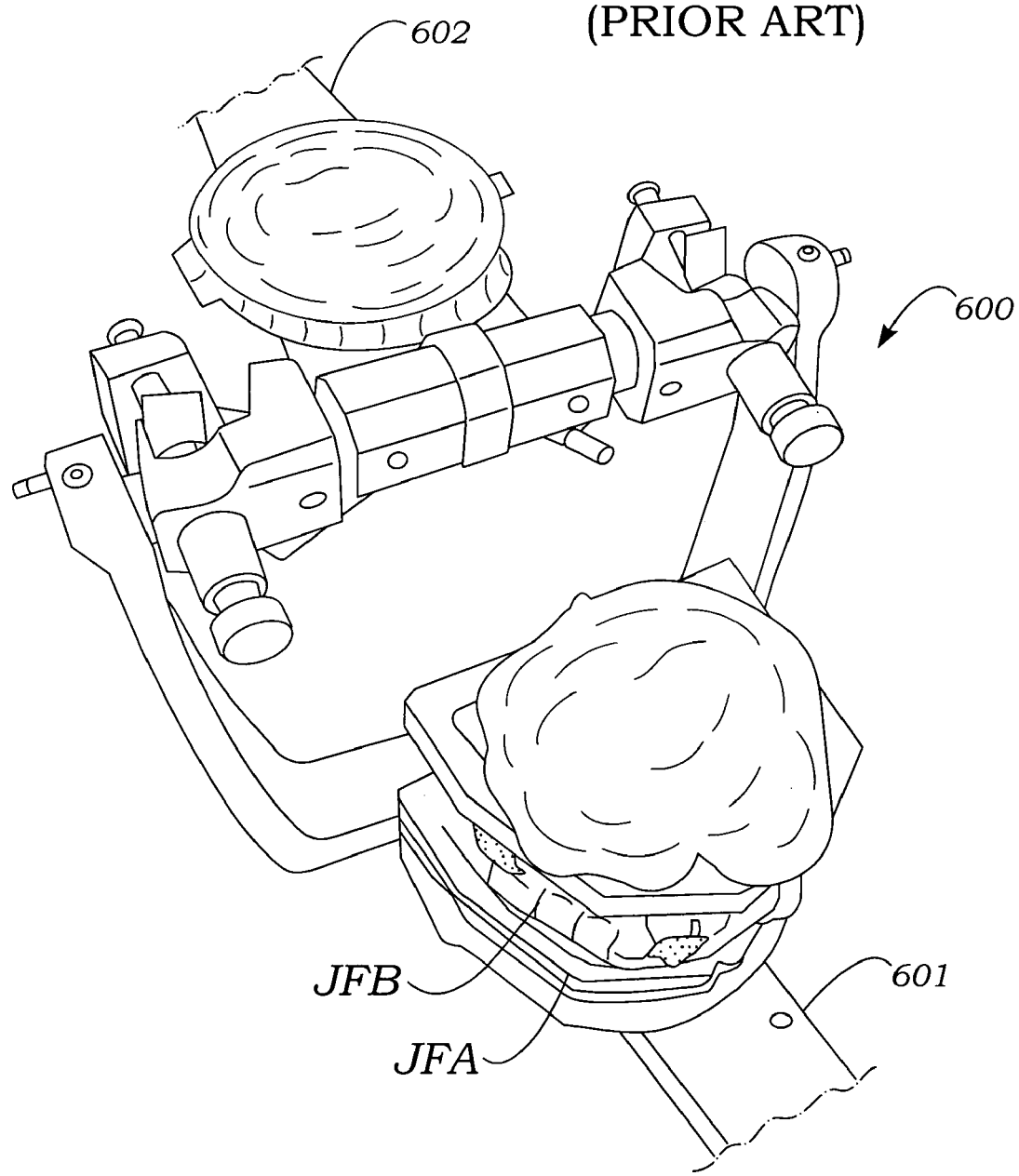
Figure 50L:
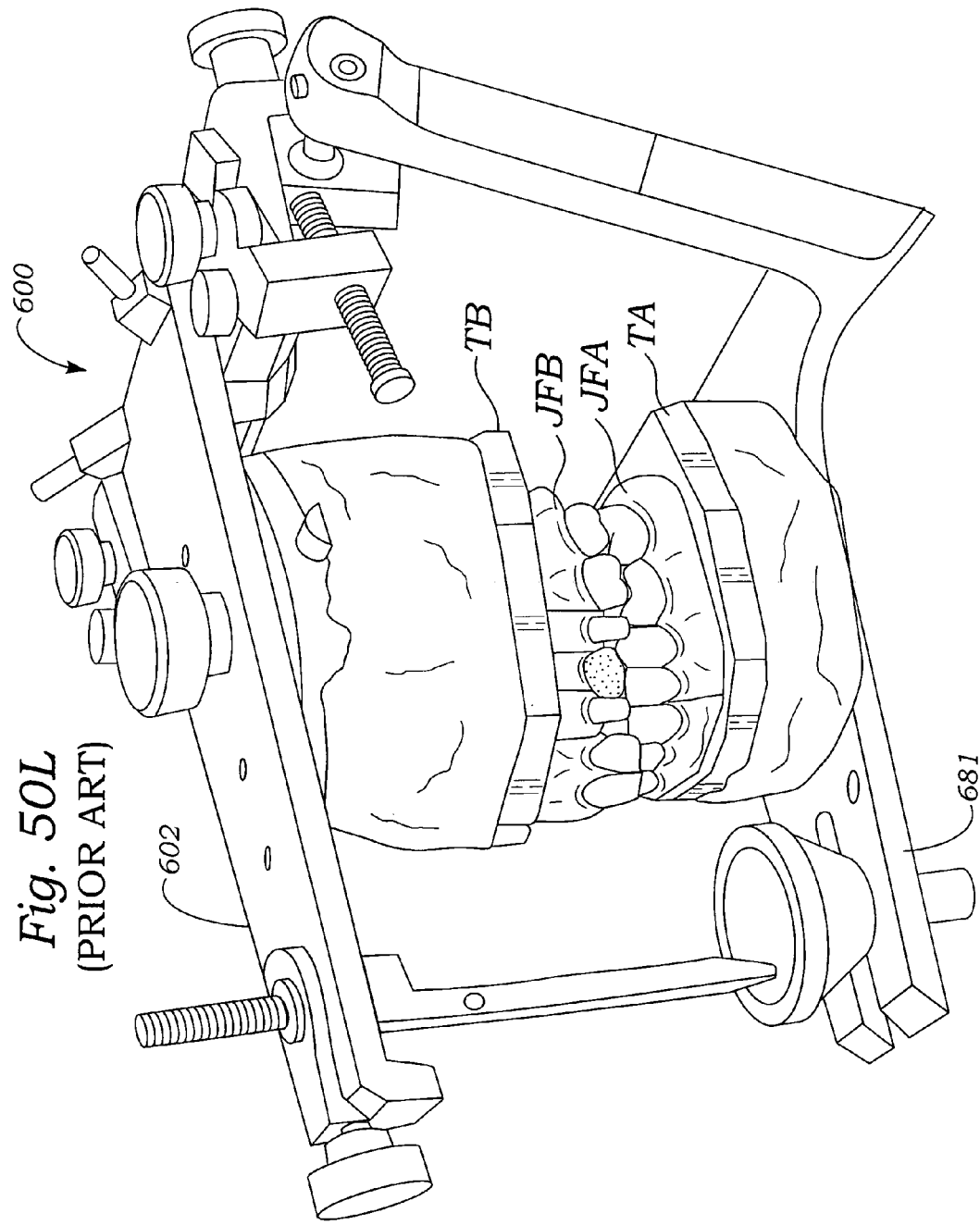

The steps described above for attaching a lower full-arch dental model cast JFA to lower articulator arm 601, including a last step depicted in FIG. 50K, are repeated to attach upper full-arch dental model cast JFB to upper articulator arm 602, thus making a complete articulated dental model as shown in FIG. 50L. By employing magnetic means for attaching trays T to mounting plates 603, as described above, upper and lower arches JFA, JFB may be separately removed from 3-D articulator 600 for performing laboratory processing operations on the dental models, and replaced on the articulator in a repeatable occlusal relationship. The dental models are finally removed from the articulator for transporting to the dentist upon completion of laboratory processing of the dental models and prostheses made therefrom. The prior art method and apparatus described above affords no means, absent an expensive duplicate 3-D articulator apparatus in the dentist's office, for positioning a pair of full-arch dental models into a proper occluding relationship for inspection by the dentist and/or patient.

FIGS. 51-54 illustrate the structure and function of a novel full-arch dental model slide receptacle 620 according to the present invention. As will be described in detail following a description of the construction of slide receptacle 620, the slide receptacles enable full-arch dental model casts contained in trays 431 to be replaceably removed from a laboratory articulator, whereupon the models may be returned to the dentist and attached to a lighter duty, less expensive, disposable articulator hinge mechanism 32 to comprise an articulated pair of upper and lower full-arch dental models for viewing by a dentist and his or her patient.

Figure 51:
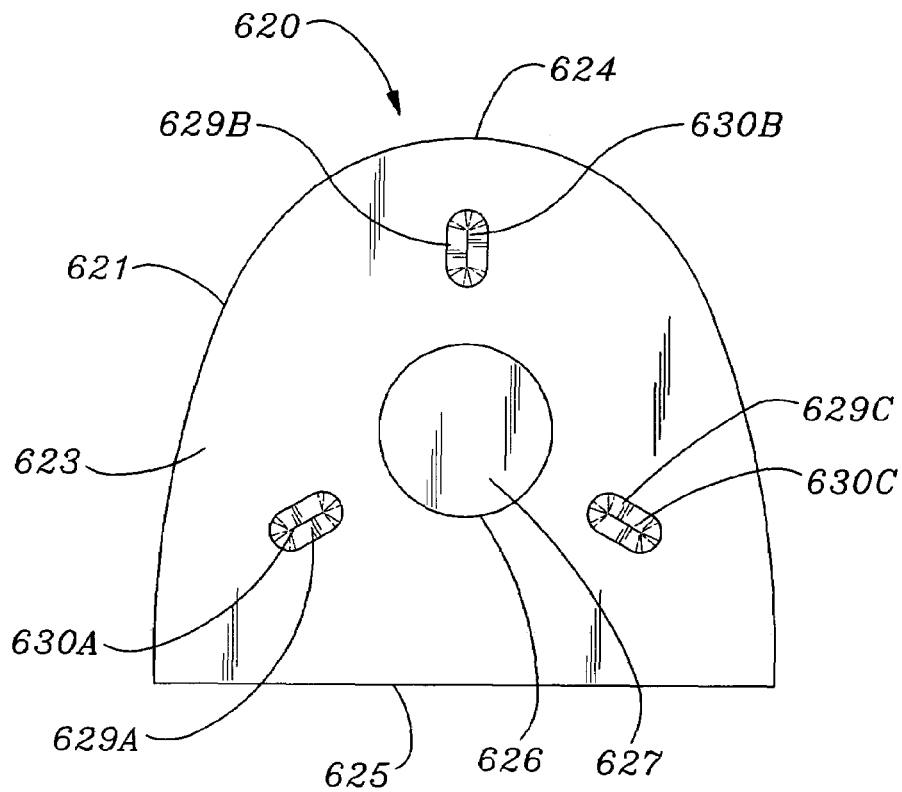
FIG. 51 is a reverse or lower plan view of an articulator slide receptacle according to the present invention.
Figure 53B:
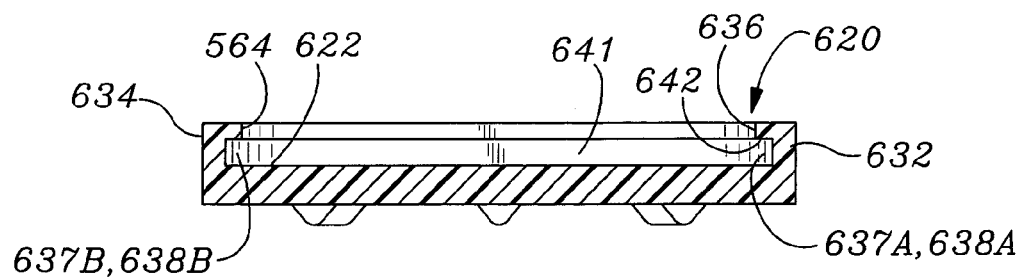
FIG. 53B is a vertical sectional view of the receptacle of FIG. 53, taken in the direction of line 53B-53B.
Figure 53:
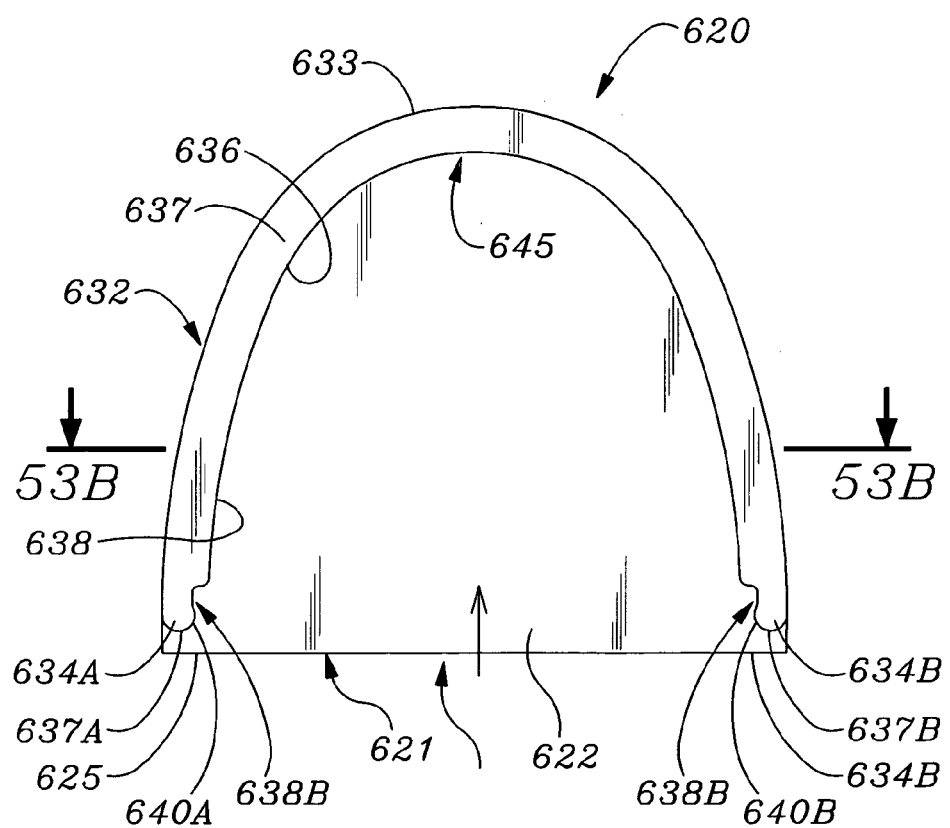
FIG. 53 is an obverse or upper plan view of the receptacle of FIG. 52.

As shown in FIGS. 51 and 53, slide receptacle 620 for use with full-arch dental modeling trays 431 includes a semi-elliptically shaped base plate 621 which has a flat upper surface 622, a flat lower surface 623 parallel to the upper surface, an arcuately curved, vertical anterior wall surface 624, and a straight, transversely disposed posterior vertical wall surface 625 which coincides with a minor axis of the semi-elliptically shaped base. As shown in FIG. 51, base plate 621 has formed in flat lower surface 623 thereof a generally centrally located circular blind bore 626 in which is held a flat circular disk 627. Disk 627 is made of a ferromagnetic material such as iron or nickel, and has a flat lower surface 628 which is co-planar, i.e., flush with lower surface 623 of base plate 621.

Figure 52:
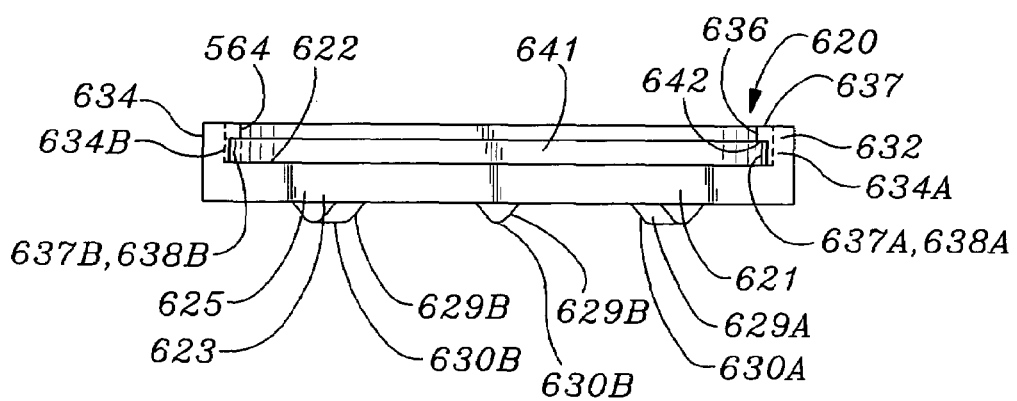
FIG. 52 is a rear end elevation view of the receptacle of FIG. 51.

Referring still to FIG. 51, it may be seen that base plate 621 has protruding downwardly from lower surface 623 thereof a plurality of locating or indexing members 629, which are spaced radially outwardly from disk 627, and spaced circumferentially apart from each other. Although the precise number, spacing and shape of indexing members 629 is not critical, the embodiment of slide receptacle 620 shown in FIG. 51 includes three radially elongated, generally rectangular plan view ribs 629A, 629B, 629C which have generally triangular cross-sectional shapes modified by curved vertices 630A, 630B, 630C. Ribs 629A, 629B, 629C are spaced apart at approximate 120-degree angles and equidistant from the center of disk 627, which is approximately centered on a focus of semi-elliptically shaped base plate 621. Ribs 629 radiate from the center of disk 627, and as shown in FIG. 52, protrude perpendicularly downwards from lower surface 623 of base plate 621 and have lower surfaces 631 disposed parallel to lower plate surface 623. The function of ribs 629 is described below.

Referring now to FIGS. 52 and 53, it may be seen that full-arch slide receptacle 620 includes a flange wall 632 which has in plan-view the shape of a semi-elliptical sector that protrudes perpendicularly upwards from upper surface 622 of semi-elliptically shaped base plate 621 of the receptacle. Flange wall 632 has an arcuately curved, outer vertical anterior wall surface 633 which is perpendicularly aligned with arcuately curved anterior wall surface 624 of base plate 621, and has at posterior ends thereof a pair of opposed transversely aligned vertical end walls 634A, 634B, which are parallel to and offset a short distance forward from transversely disposed posterior vertical wall surface 625 of the base plate. Arcuately curved anterior flange wall 632 has protruding perpendicularly inwardly from a curved inner wall surface 635 on the flange wall which is parallel to its outer anterior wall surface 633 a radially inwardly turned lip 636 which has a flat upper surface 637. As shown in the figures, lip 636 has the shape of a semi-elliptical sector which has an outer arcuately curved perimeter coextensive with that of curved outer surface 633 of flange wall 632, and an inner perimeter wall 638 spaced radially inwardly from inner wall surface 635 of the flange wall. Also, as shown in FIG. 53, lip 636 has formed in rear transversely aligned and opposed ends 637A, 637B thereof proximate rear end walls 634A, 634B of flange wall 632 a pair of opposed forward protruding cut-outs or notches 638A, 638B. As is also shown in FIG. 53, rear end portions 639A, 639B of upstanding flange wall 632 have formed in upper halves thereof transversely inwardly disposed, opposed, arcuately curved club-shaped retainer enlargements 640A, 640B.

Figure 54A:
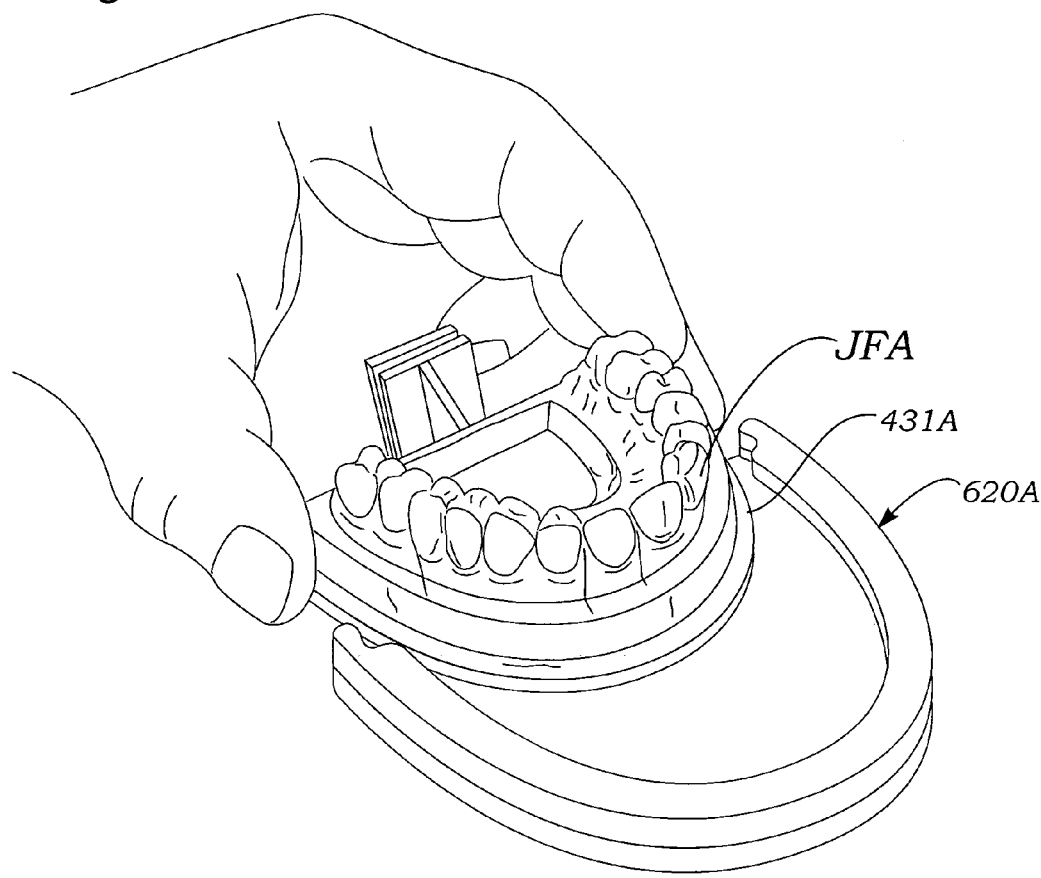
FIG. 54A is a perspective view showing a lower full-arch trays of a pair of upper and lower dental model castings and the manner of installing the trays on a receptacles of FIGS. 51-53.
Figure 54B:
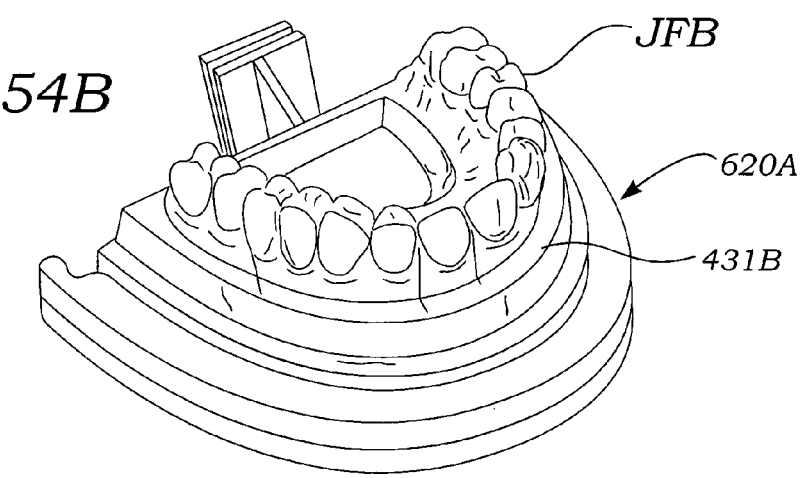
FIG. 54B shows a full-arch tray installed in a tray receptacle of FIGS. 54-53.
Figure 54C:
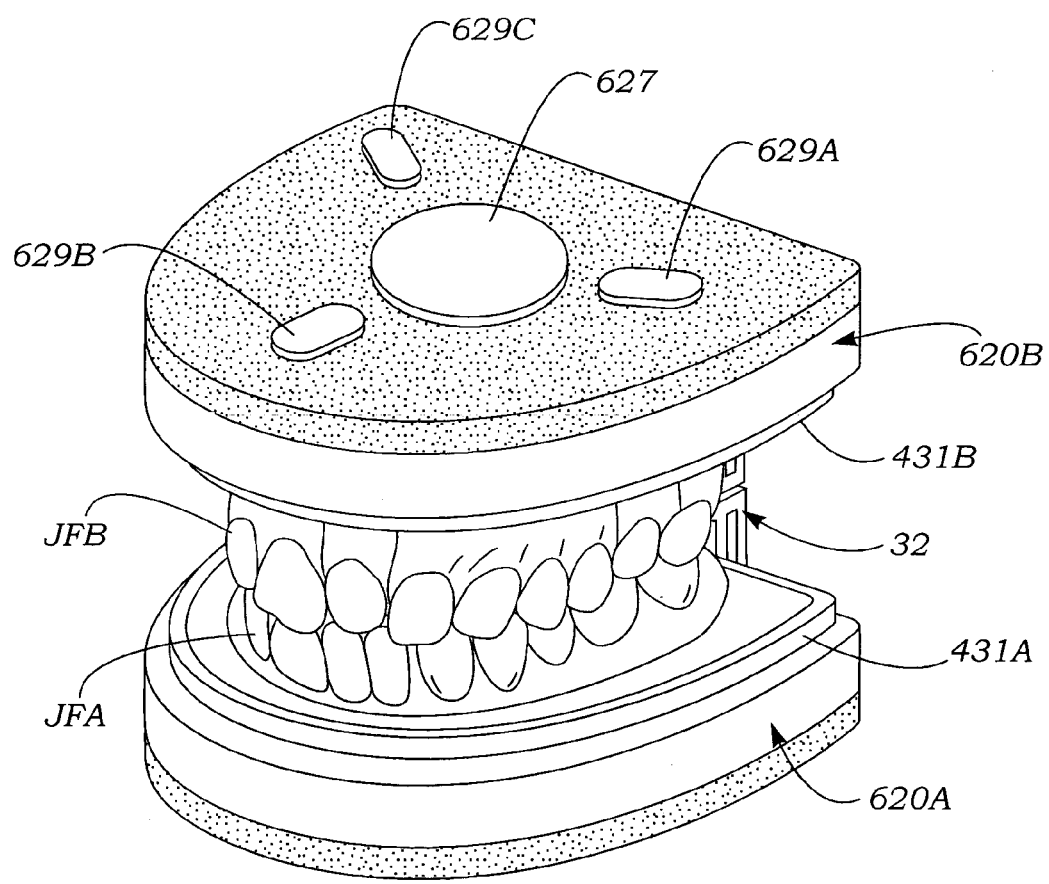
FIG. 54C shows the pair of receptacle-mounted trays of FIG. 54A and 54B joined in an occlusal relationship by the hinge coupler of FIG. 3A.
Figure 55A:
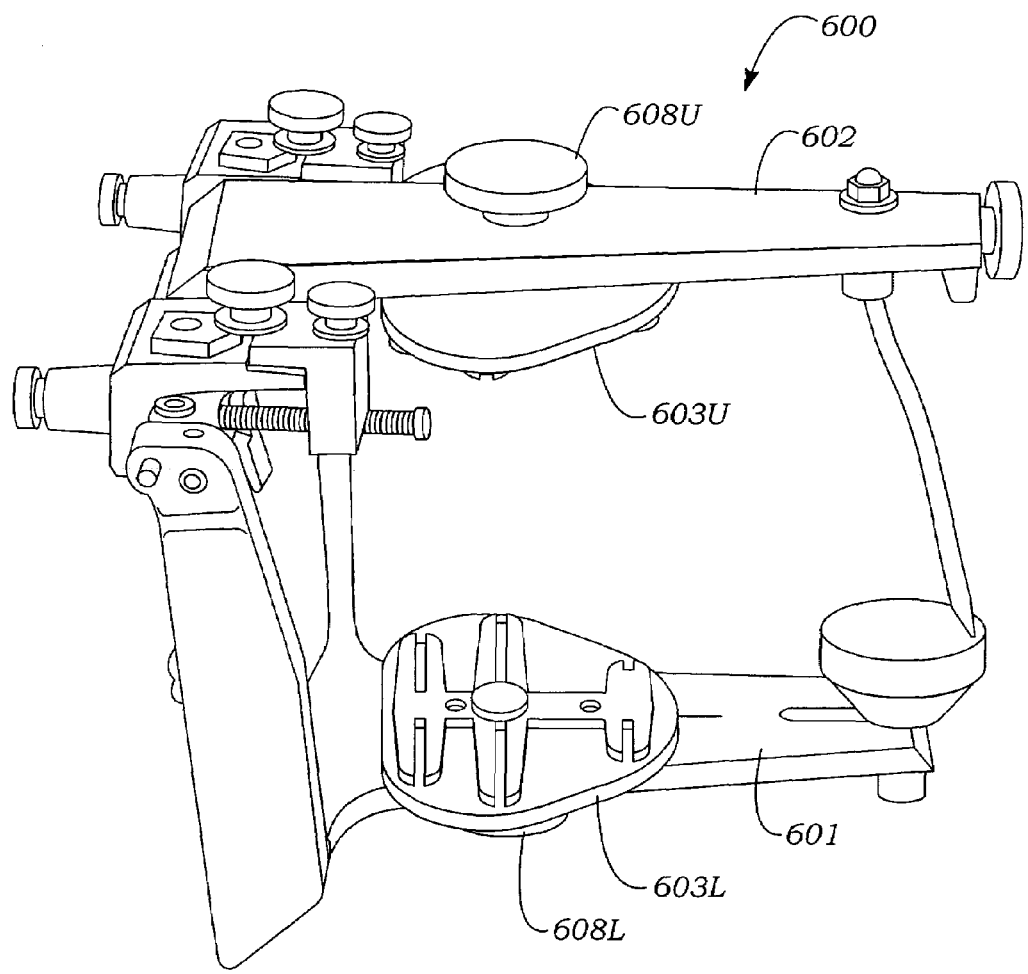
FIG. 55A is a perpective view of a 3-D articulator for use with a method of the present invention.
Figure 55B:
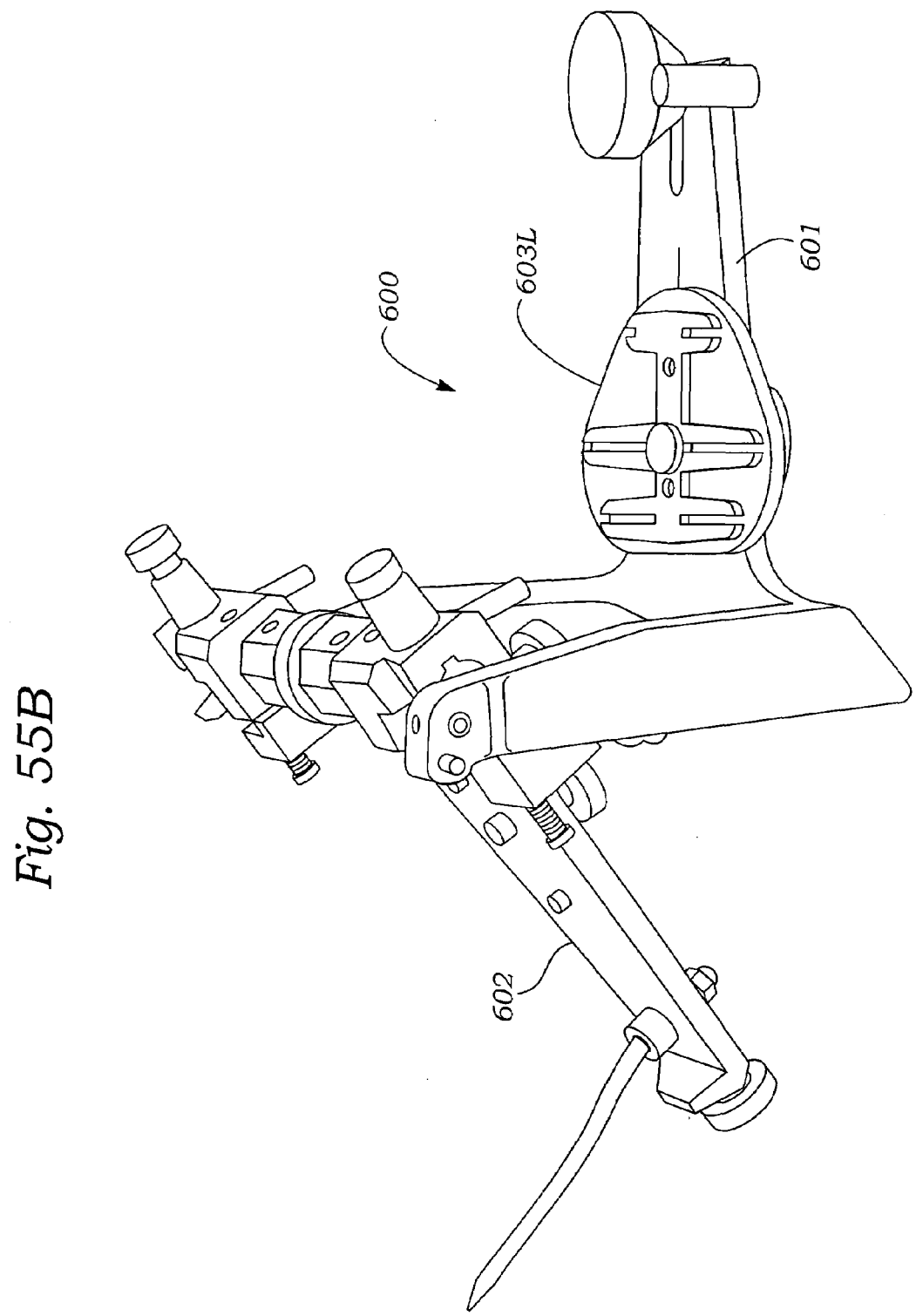
FIG. 55B is a perspective view of a first step in a method according to the present invention of attaching an articulator slide receptacle holding a lower full-arch tray and dental model cast of FIGS. 54-54C, to the lower arm of a 3-D articulator.
Figure 56:
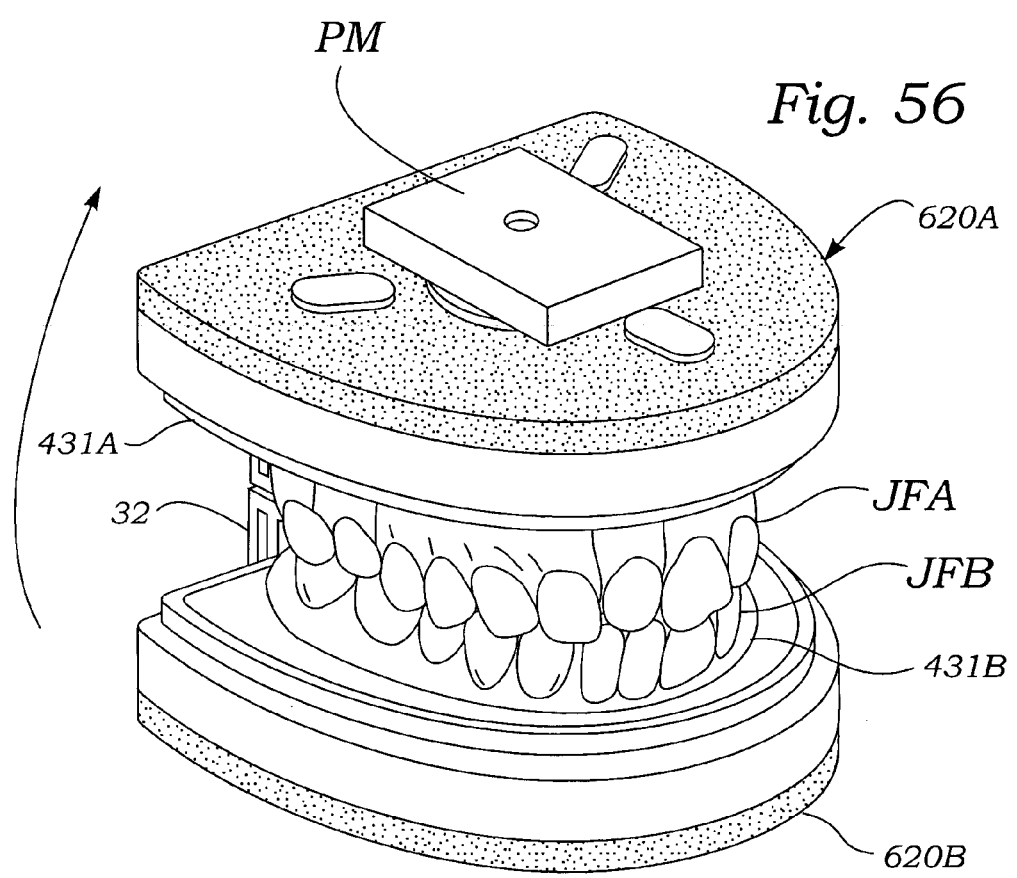
FIG. 56 is a perspective view showing a second step for attaching the lower slide receptacle of FIG. 55 to the lower articulator arm.

Semi-elliptically curved flange wall 632, and radially inwardly disposed lip 636 which protrudes perpendicularly inwards from the flange wall have inner adjacent vertical and horizontal surfaces 641, 642, respectively, which together with upper surface 622 of receptacle base plate 621 form a semi-elliptically curved channel 643 that is of the proper size and shape to slidably receive semi-elliptically curved lower base surface 434 of a full-arch tray 431. Thus, as shown in FIG. 54, to removably install a tray 431 in receptacle 620, base surface 434 of a full-arch tray 431 is placed on upper surface 622 of the receptacle and slid forward on that surface, into channel 643, the upper surface of anterior abutment flange 455 sliding forward on lower surface 644 of lip 636. Tray 431 is slid sufficiently far forward within the channel 643 for vertex 455V of anterior abutment flange 455A to abut the vertex 645 of inner vertical surface 646 of vertical flange wall 642. Thus positioned, opposed transverse corners of rear abutment flange 455B of tray 432 frictionally wedge between retainer enlargements 640A, 640B, respectively, of flange wall 632, thus retaining tray 431 securely fixed within channel 643 of slide receptacle 620.

Figure 57:
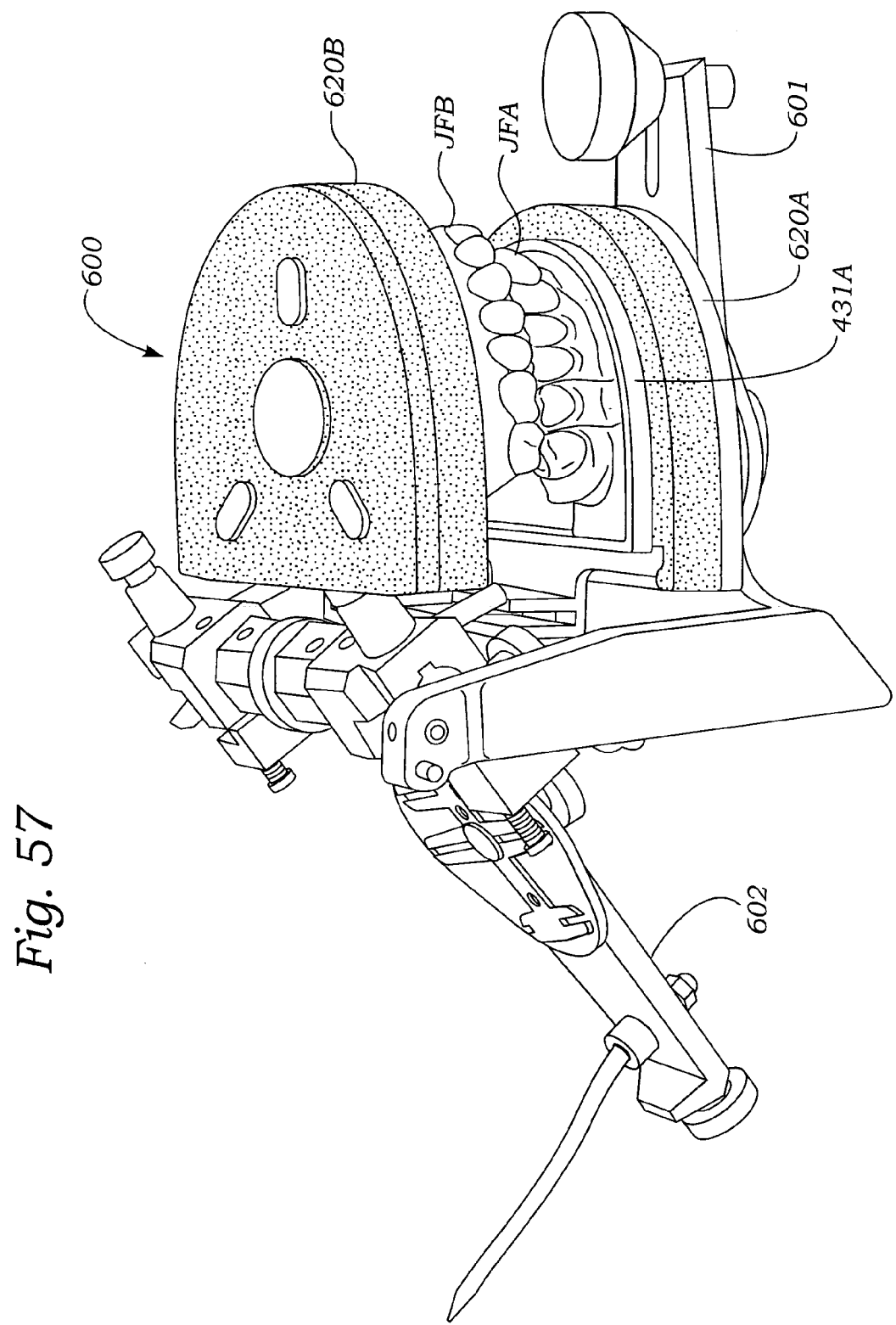
FIG. 57 is a lower perspective view showing a third step in attaching the lower slide receptacle to the lower articulator arm.

FIGS. 54-62 illustrate the manner of using full-arch tray slide receptacle 620. As shown in FIG. 54A, 54B, a pair of lower and upper full-arch dental model trays 431A, 431B containing lower and upper dental model casts JFA, JFB, and joined by an articulator hinge mechanism 32 are slidably mounted in a pair of lower and upper slide receptacles 620A, 620B, in the manner described above. Next, as shown in FIGS. 56A, 56B, a relatively thick layer of viscous semi-liquid die stone is applied to the upper surface 604 of a first, lower arch mounting base plate 603, and the base plate is attached to lower arm 601 of articulator 600 by means of a lower arm thumbscrew 608A. Then, as shown in FIG. 57, a pot magnet PM is magnetically attached to disk 627 of lower slide receptacle 620A. Following this step, as shown in FIGS. 57A and 57B, a relatively thick layer of semi-liquid die stone is applied over pot magnet PM and the lower surface of inverted slide receptacle base plate 621. Lower slide receptacle 620A containing lower full-arch tray 431A and dental model cast JFA is then, uprighted, and the semi-liquid die stone layer on the lower surface of the slide receptacle pressed into the semi-liquid die stone layer on the upper surface of lower mounting base plate 603. Time is then allowed for the two die stone layers to cohere and harden into a unitary mass.

Figure 58B:
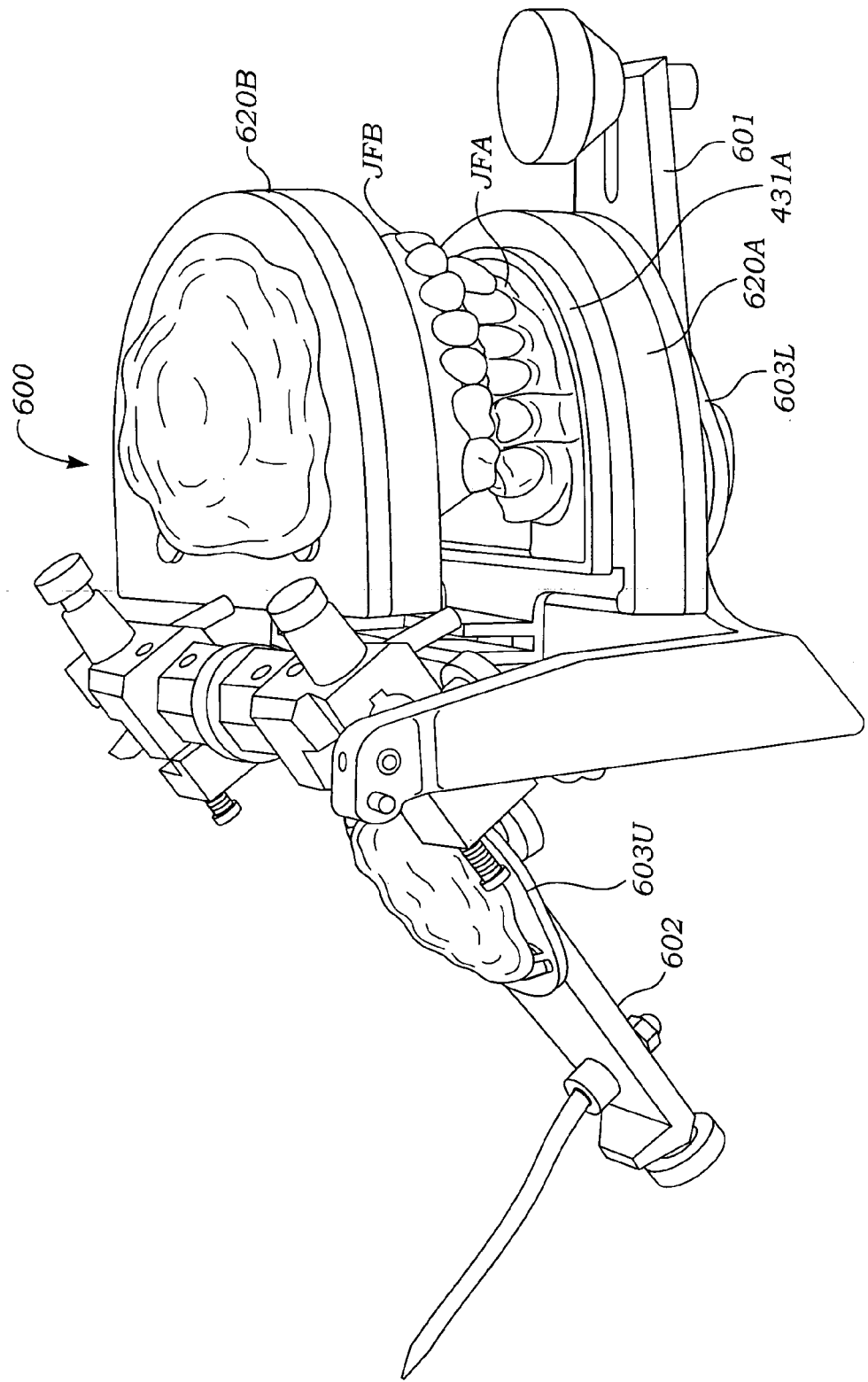
FIG. 58B is a perspective view showing the upper slide receptacle of FIG. 58A, to which a pot magnet has been magnetically attached, and semi-liquid die stone applied to the upper surface of the slide, and to the lower obverse surface of a second plastic mounting plate attached to the upper pivotable articulator arm preparatory to pivoting the arm downwardly to press the semi-liquid die-stone coated surfaces together to cohere and harden.
Figure 59:
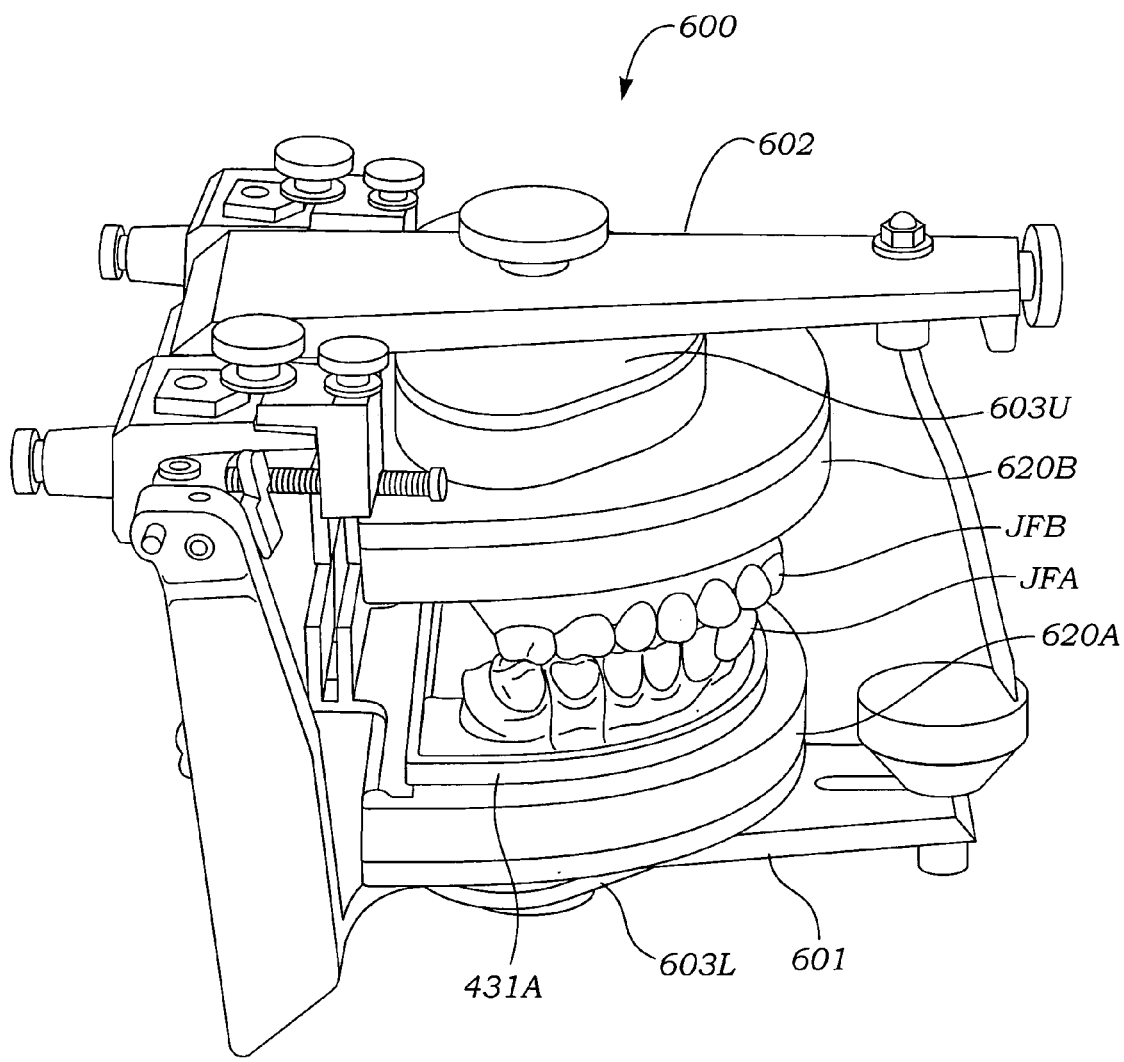
FIG. 59 is a perspective view showing a finished pair of upper and lower full-arch dental model casts contained in a pair of trays mounted in a pair of slide receptacles magnetically attached to upper and lower arms of the 3-D articulator.

As shown in FIGS. 58 and 59, the steps described above for attaching a lower full-arch dental model cast JFA contained in tray 431A temporarily slidably mounted in a first lower slide receptacle 620A are repeated to attach a second, upper slide receptacle 620B holding an upper full-arch tray 431B and upper full-arch dental model cast JFB to upper articulator arm 602, thus making a complete articulated dental model as shown in FIG. 59.

Figure 60:
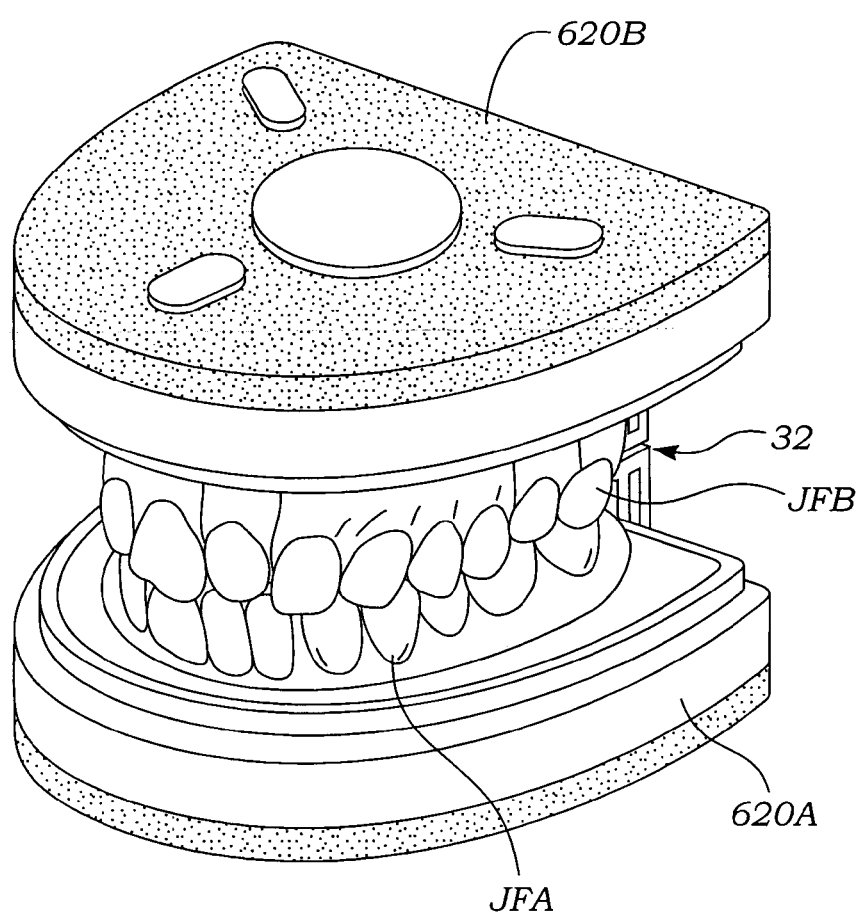
FIG. 60 is a perspective view showing full-arch dental model casts, trays and slide receptacles removed from the articulator of FIG. 59.
Figure 61:
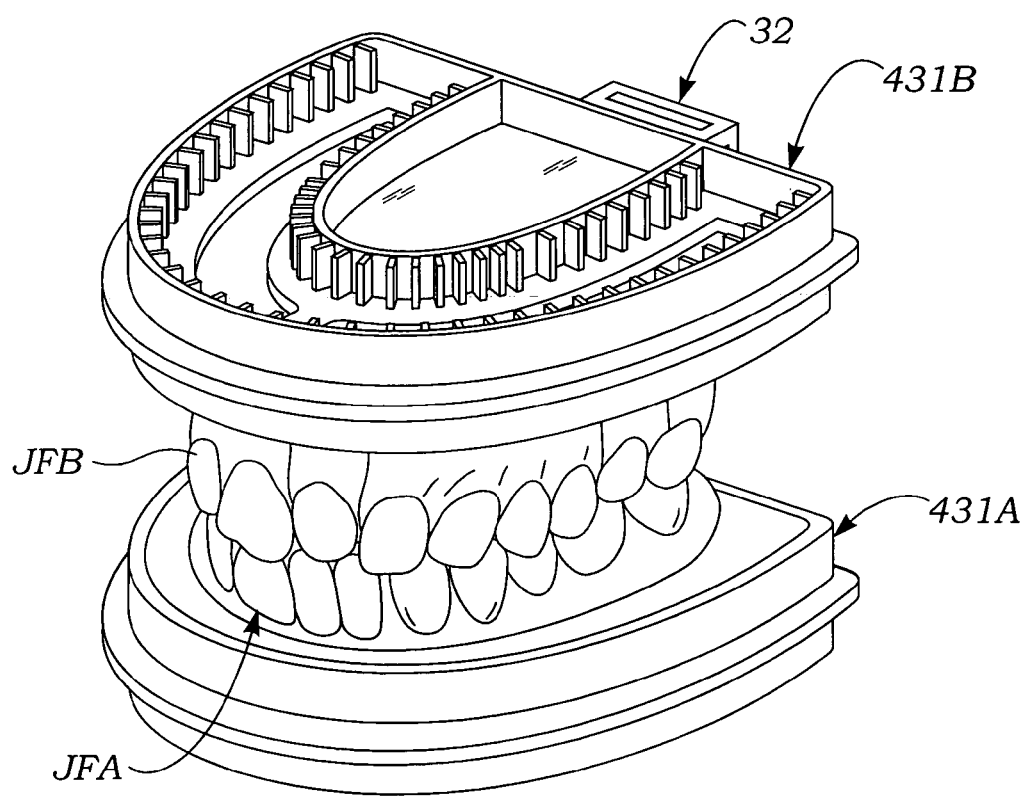
FIG. 61 is a view showing a pair of full-arch dental model casts contained in trays removed from the slide receptacles of FIG. 60 and joined together by a hinge mechanism for viewing approximate occlusal relationship, by a dentist and patient, yet returnable to a precisely re-locatable occlusal relationship in the 3-D articulator by re-inserting the trays into slide receptacles and magnetically adhering the slide receptacles to arms of the 3-D articulator.

By employing magnetic attachment means for mounting lower and upper full-arch slide receptacles 620A, 620B to lower and upper articulator arms 601, 602, the slide receptacles may be separately and repeatedly removed from 3-D articulator 600 to enable various laboratory processing operations required for the manufacture of dental prostheses to be performed on dental model casts JFA, JFB, and the slide receptacles re-attached to the articulator arms in precisely pre-determined positions enabled by indexing ribs 629 seating in cavities formed in die stone and adhered to base plates 603L, 603U of articular 600, which provide proper occlusal relationship which provide proper occlusal relationship between the models. Moreover, upon completion of laboratory processing of dental models and prostheses made therefrom using full-arch slide receptacles 620 according to the present invention, slide receptacles 620A, 620B containing lower and upper full-arch trays 431A, 431B and dental models JFA, JFB can be quickly and easily removed from the articulator, as shown in FIG. 60, and the trays quickly and easily slidably removed from the slide receptacles, as shown in FIG. 61. The trays 431A, 431B containing the full-arch lower and upper dental model casts JFB, JFB can then be returned to the dentist's office where they are readily connectable by a low-cost articulator hinge mechanism 32 to form an articulated full-mouth dental model which has a proper occlusal relationship of sufficient precision, for inspection by the dentist and viewing by his or her patient, as shown in FIG. 61.

Figure 63:
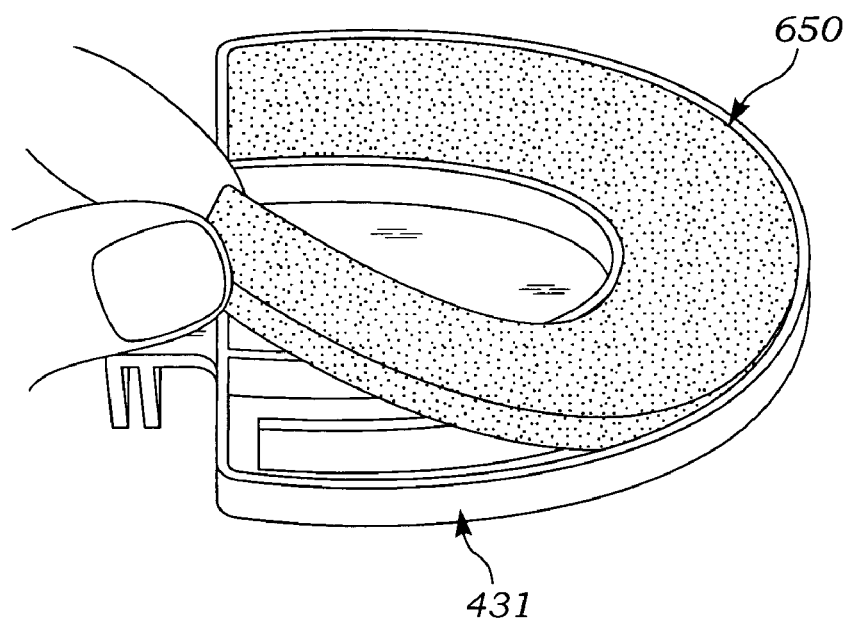
FIG. 63 is a lower plan view of the insert of FIG. 62 and tray of FIG. 36, showing a method of installing and removing the insert in a lower well portion of the tray.
Figure 62:
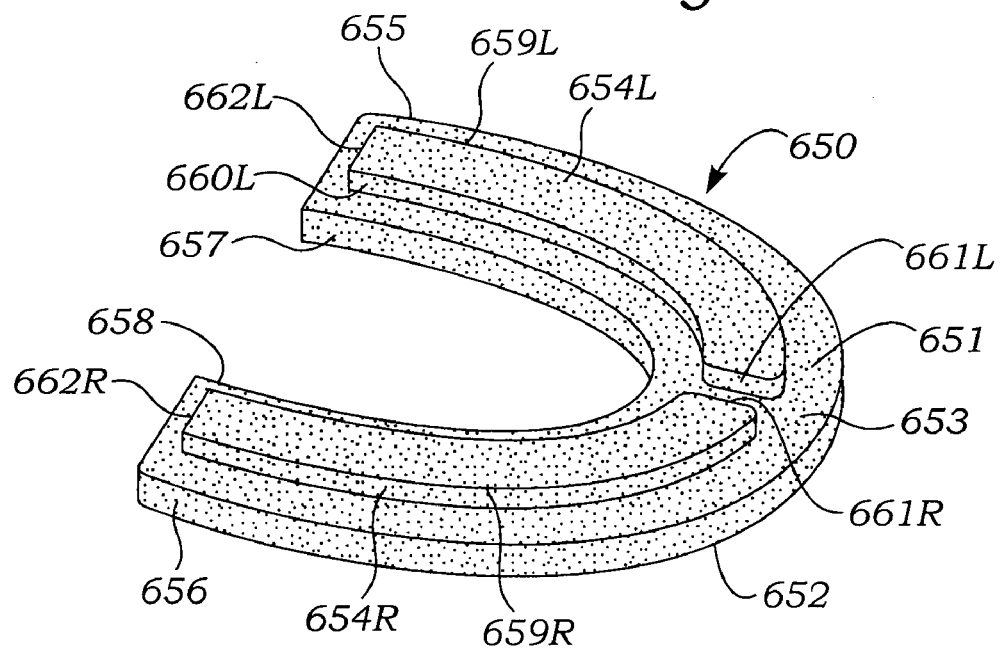
FIG. 62 is an upper perspective view of an insert for use with a tray of the type shown in FIG. 36, modified by removal of break-away panels from the tray.

FIGS. 62-65 illustrate the structure and function of an insert 650 for use with a full-arch modeling tray 431 according to the present invention. As shown in FIGS. 62-65, insert 650 has a flat, longitudinally elongated, semi-elliptical arch-shaped plan-view base plate 651. As shown in FIGS. 62 and 63, base plate 651 of insert 650 has a generally uniform thickness, and has flat and parallel lower and upper surfaces 652, 653, respectively. Referring to FIG. 62, insert 650 may be seen to include a pair of longitudinally elongated, quarter-elliptically-shaped plan view bosses 654L, 654R, which protrude upwardly from upper surface 653 of insert base plate 651, the bosses being concentrically located with respect to convex outer, inner and concave inner and left and right rear transverse perimeter wall surfaces 655, 656, 657 and 658, respectively, of the base plate. As shown in FIG. 62, bosses 654L, 654R of insert 650 have generally vertically disposed outer convex and inner concave side walls 659, 660, and front and rear transverse side walls 661, 662, which are inclined towards a vertical, longitudinally disposed mid plane of the boss.

Figure 65:
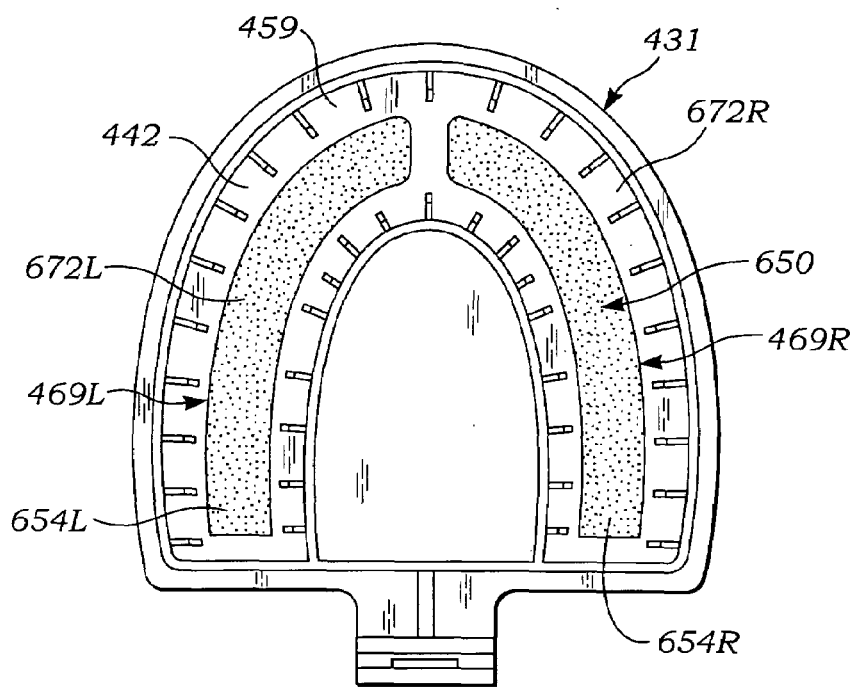
FIG. 65 is an upper plan view of the tray and insert of FIG. 64.
Figure 64:
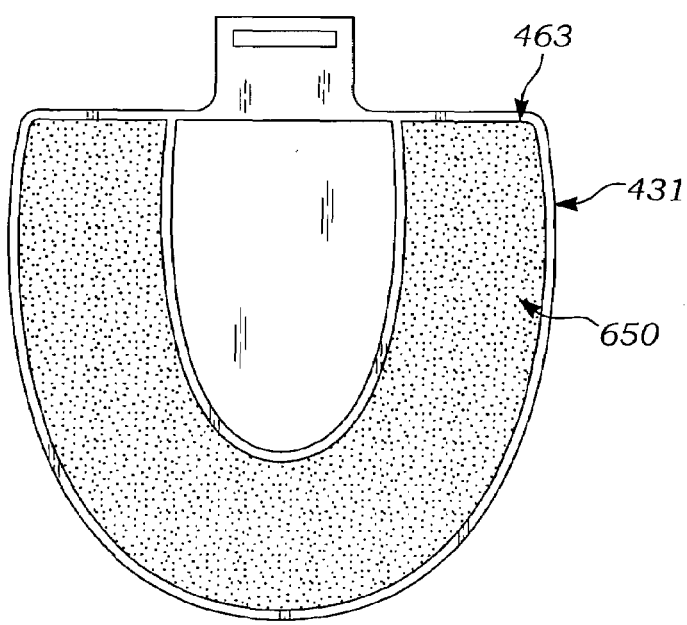
FIG. 64 is a lower plan view of the tray and installed insert of FIG. 63.

Referring now to FIGS. 63-65, it may be seen that insert 650, constructed as described above, is adapted to be fitted into lower well 463 of tray 431, with bosses 654L, 654R fitting conformally within apertures 469L, 469R through base wall 442 of the tray. Thus positioned, upper surfaces 672L, 672R are substantially flush with upper surface 459 of base wall 442 of tray 431.

In a preferred embodiment, tray insert 650 is made of a resilient material, e.g., an elastomeric polymer such as polyurethane. This choice of materials enables bosses 654L, 654R to fit resiliently within apertures 469L, 469R through base wall 442 of tray 431 in a liquid tight seal therewith. Liquid die stone may then be poured into upper wells 439L, 439R of tray 431 to form the base of a dental model cast, in the manner shown and described above. After liquid die stone has hardened to form a cast, insert 650 is readily withdrawn from lower wells 463L, 463R of tray 431, by grasping an edge of base plate 301 and exerting a downwardly directed parting force relative to the tray, as for example, by grasping an edge of the tray and an edge of the insert base plate between a thumb and forefinger and exerting a pinching force thereon. Following removal of insert 650 from tray 431, a dental prostheses may be fabricated according to the steps shown and described above.

FIGS. 66-72 illustrate modifications of the dental tray and inserts shown in FIGS. 1-3, 30-32, and 36-38 and described above. The modifications consist of additional structural elements which are effective in forming grooves in the bottom surfaces of dental model casts made using the modified trays and inserts. As is explained in detail below, a groove formed in the base of a dental model cast facilitates drilling bores into the base for receiving manipulating pins.

Figure 66:
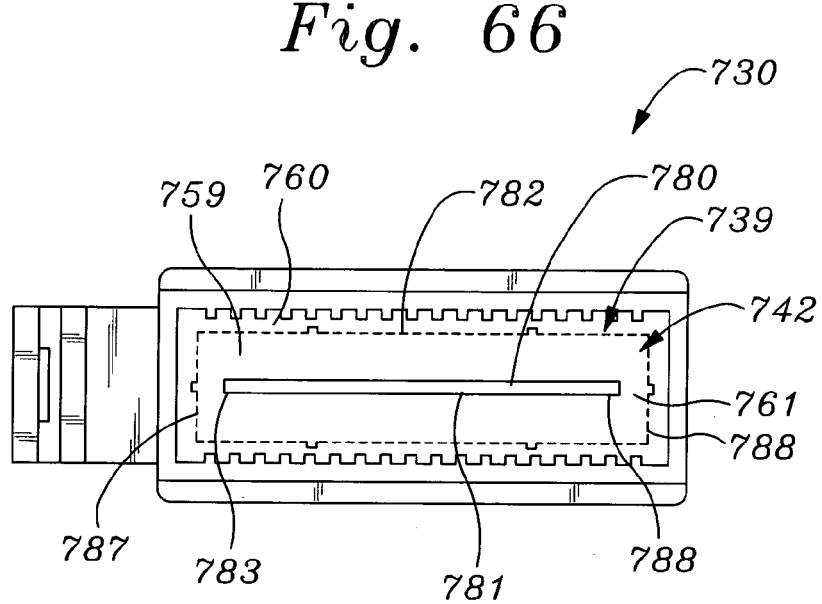
FIG. 66 is an upper perspective view of a modification of the quadrant modeling tray shown in FIGS. 1-3, which has a ribbed break-away panel.

Referring first to FIG. 66, a modified dental modeling or molding tray 730 for use in forming dental model casts from liquid die stone poured into the tray and into a dental impression of a quadrant portion of a patient's mouth may be seen to be identical in every respect to the quadrant tray 30 depicted in FIG. 1-3 and described above, with the following single exception. As shown in FIG. 66, break-away base wall panel 761 portion of base wall 742 of modified quadrant tray 730 is provided with a straight, longitudinally elongated, rectangular cross-section rib 780 which protrudes upwardly from upper surface 759 of the break-away base panel. As shown in FIG. 66, rib 780 is located midway between front and rear longitudinally disposed edge walls 781, 782 of break-away panel 761. As is also shown in FIG. 66, left and right edges 783, 784 of rib 780 are preferably spaced short equal distances inwardly from left and right side 787, 788, a height less than the depth of upper well 739 of tray 730, and preferably has a height of about respectively of the break-away panel. Although the exact dimensions of rib 780 are not critical, the rib has ¼ inch.

FIG. 64 is a lower plan view of modified quadrant tray 730, in which a break-away panel 780 thereof has been removed after the tray has been used to pour a dental model cast J, the lower surface M of the base of which is visible through an aperture formed in base wall 742 of the tray by removal of the break-away panel. As shown in FIG. 64, the lower base surface M of dental model cast base J has protruding inwardly thereof a longitudinally disposed groove Q which was molded into the base by rib 780 of break-away panel 781, and which therefore has a shape complementary to that of rib 780 of break-away panel 761. As is also shown in FIG. 64, base M of dental model cast J has been cut by a pair of saw cuts T1, T2 to sever an individual die segment U of the type shown in FIG. 17, from the cast.

Referring still to FIG. 64, it may be seen that dental model cast die segment U has installed into lower surface N thereof a manipulating pin 120. The presence of groove Q in the lower surface M of dental model cast J facilitates drilling pin bores at selected locations into the dental model cast, without the requirement for a drilling fixture, in the following manner. Having selected a desired location for a manipulating pin to be installed in a dental model cast J, e.g., approximately midway between opposite transverse sides of a die segment U as shown in FIGS. 17 and 63, the tip of a drill bit is inserted into groove Q in cast base surface M at the desired lateral location. Since groove Q is located midway between front and rear longitudinal sides of the cast, the drill bit is also located midway between front and rear sides of the cast. Also, since the groove has vertical side walls which preferably taper inwardly to a smaller relative spacing, a drill bit which has a diameter slightly less than the entrance width of the groove will be snugly aligned within the groove when inserted into the groove, whereupon, rotation means such as a motor may be energized to quickly and easily drill one or more pin bores into the base surface M of the dental model cast J, the bores being substantially well centered in the bases off pie segments.

Figure 67:
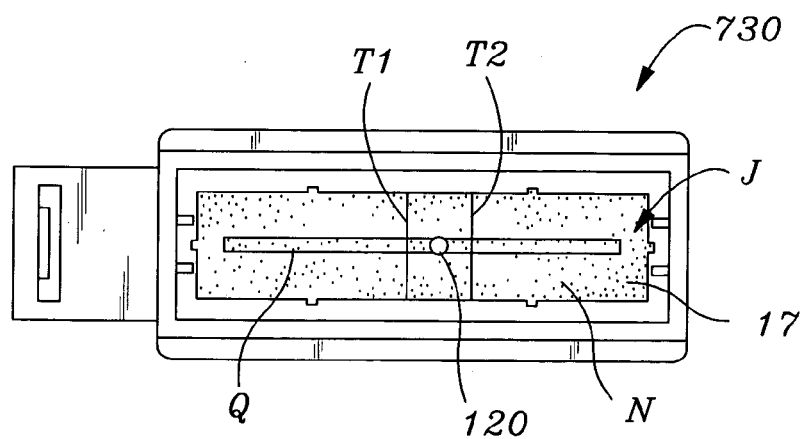
FIG. 67 is a lower plan view of the tray of FIG. 66, showing a break-away panel thereof removed after pouring a dental model cast in the upper well of the tray, a groove formed in the lower surface of the cast by a rib protruding upwardly from the break-away panel, saw cuts made in the cast to sever a die segment from the cast, a pin bore drilled into the base of the segment using the groove as a pilot for a drill bit, and a manipulating pin installed in the pin bore.

FIGS. 65-67 illustrate a modification 800 of the quadrant modeling tray insert shown in FIGS. 30-32. Modified quadrant tray insert 800 is identical in structure and function to insert 300 depicted in FIGS. 30-32, with the following exception. As shown in FIGS. 65-66, modified insert 300 is provided with a straight, longitudinally elongated, rectangular cross-section rib 880 which protrudes upwardly from upper surface 822 of the insert. When modified insert 800 is installed in a modeling tray 231 of the type shown in FIGS. 28 and 29, and used to pour a dental model cast in the manner described above, a groove Q is molded into the base of the cast by rib 880. Groove Q is exactly similar to groove Q shown in FIG. 64, and affords the same advantages of guiding a drill bit to drill a pin bore as described above.

Figure 71:
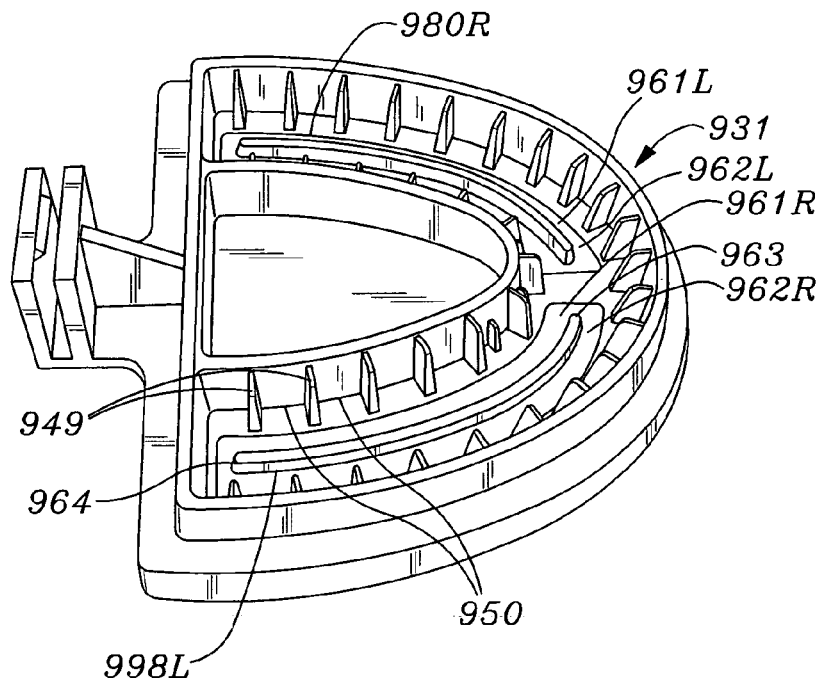
FIG. 71 is an upper perspective view of a modification of the full-arch dental modeling tray of FIG. 36, which has ribbed break-away panels.
Figure 72:
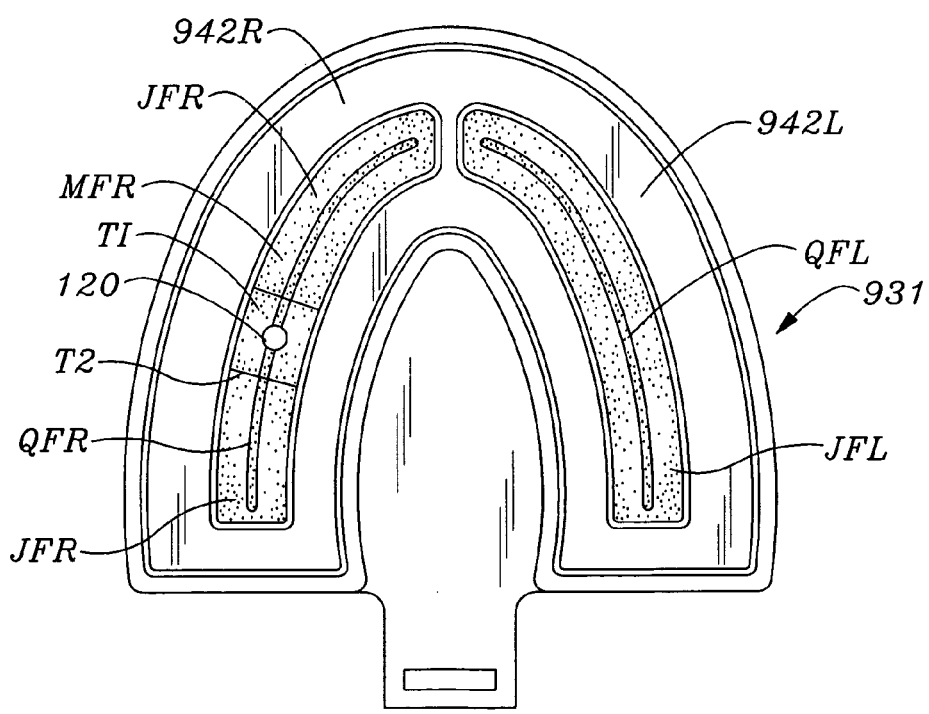
FIG. 72 is a lower plan view of the tray of FIG. 68 showing a break-away panel thereof removed after pouring a dental model cast in the upper well of the tray, a groove formed in the lower surface of the cast by a rib protruding upwardly from the break-away panel, saw cuts made in the cast to sever a die segment from the cast, a pin bore drilled into the base of the segment using the groove as a pilot for a drill bit, and a manipulating pin installed in the pin bore.

FIGS. 71 and 72 illustrate a modification 931 of a full-arch dental modeling tray 431 shown in FIGS. 36-38 and described above. Modified full arch tray 931 is substantially similar in structure and function to full arch tray 431, with the following exceptions.

Figure 68:
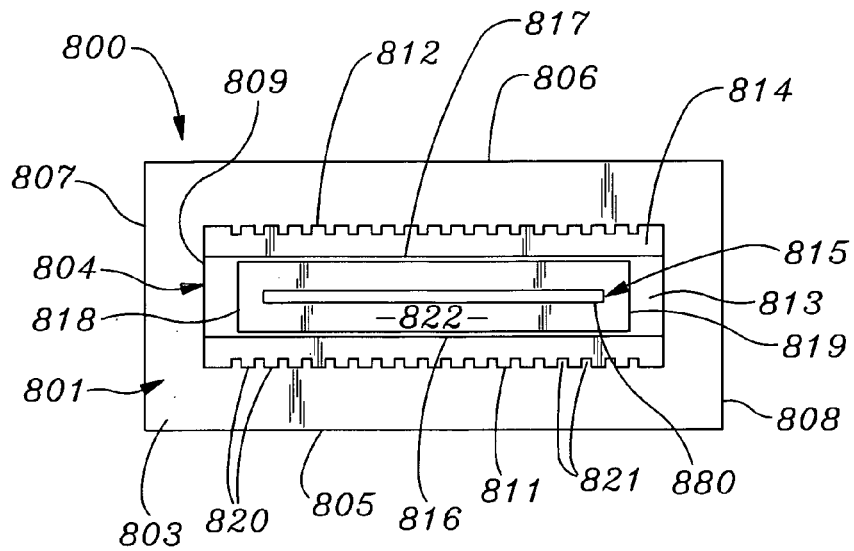
FIG. 68 is an upper plan view of a modification of the quadrant modeling tray insert shown in FIGS. 30-32, which is provided with a pilot groove-forming rib.
Figure 69:
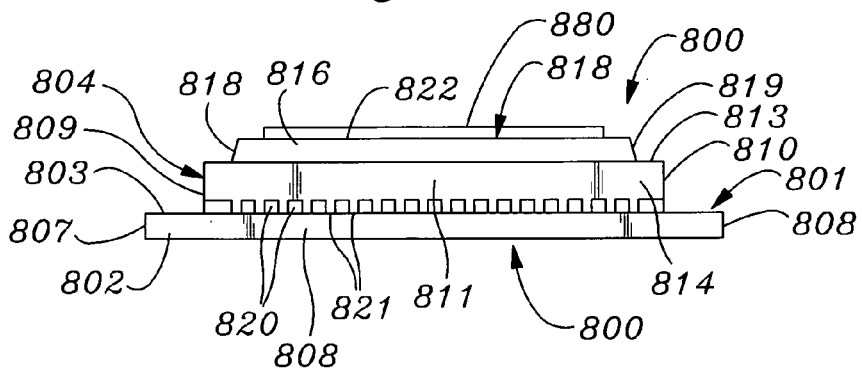
FIG. 69 is a front elevation view of the modified insert of FIG. 68.
Figure 70:
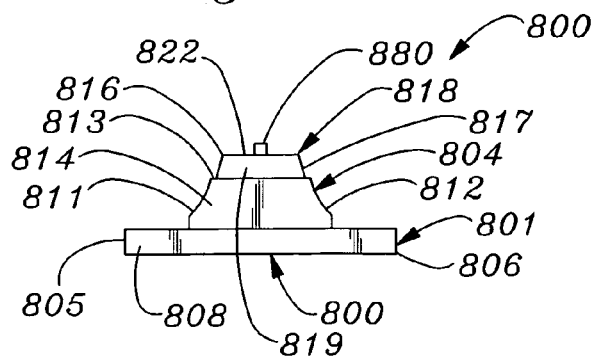
FIG. 70 is a right side elevation view of the insert of FIG. 69, the left side elevation view being identical to the right side elevation view.

As shown in FIG. 71, modified full arch dental modeling tray 931 has arcuately curved left and right break-away center panels 961L, 961R which have protruding upwardly from upper surfaces 962L, 962R thereof arcuately curved, longitudinally elongated, generally rectangular cross section ribs 980L, 980R, respectively. As shown in FIG. 68, each rib 980L, 980R is located midway between anterior front and posterior rear arcuately curved inner wall surfaces 445U, 446U, of upper peripheral ring portion 441 of tray 931. As is also shown in FIG. 71, front and rear edges 963, 964 of rib 980 are preferably spaced short equal distances inwardly from front rear transverse sides 965, 966, respectively, of each break-away panel 961. Although the exact dimensions of rib 980 are not critical, the rib has a height less than the depth of upper well 949 of tray 931, and preferably has a height of about ¼ inch.

FIG. 72 is a lower plan view of modified full-arch tray 931, in which break-away panels 961L, 961R have been removed after the tray has been used to pour a dental model cast JF, the lower surface MFR of the right-hand base of which is visible through an aperture formed in base wall 942R of the tray by removal of the break-away panel. As shown in FIG. 71, the lower base surface MFR of right-hand dental model cast JFR has protruding inwardly thereof an arcuately curved, longitudinally disposed groove QFR which was molded into the base by rib 980R of break-away panel 961R, and which therefore has a shape complementary to that of the rib. As shown in FIG. 72, base MFR of dental model cast JFR has been cut by a pair of saw cuts T1, T2 to sever an individual die segment U of the type shown in FIG. 17, from the cast.

Referring still to FIG. 72, it may be seen that dental model cast die segment U has installed into lower surface N thereof a manipulating pin 120. Drilling of a bore for insertably receiving pin 120 is facilitated by the presence of groove Q in a manner exactly analogous to that described above in conjunction with a description of modified quadrant tray 730.

Referring again to FIG. 71, it may be seen that modified full-arch tray 931 includes, in addition to ribs 980L, 980R, an additional structure modification which may optionally be included in full-arch tray 431 shown in FIGS. 36-38 and described above. As shown in FIG. 71, front and rear inner wall surfaces 945U, 946U of upper peripheral ring 940 of tray 931 have formed therein a plurality of vertically disposed ribs 949 which protrude radially inwardly towards a longitudinal center line of upper well 939. Ribs 949 protrude vertically upwardly of base wall 942, and form between each adjacent pair of ribs a vertically disposed notch or groove 950. As shown in FIG. 71, ribs and grooves 949, 950, respectively have in elevation view the shape of a narrow vertically disposed upright and inverted triangles, or wedges, respectively. Preferably, as shown in FIG. 71, ribs 949 have a width less than that of grooves 980. This arrangement enables sufficient expansion of solidified die stone in the grooves to exert circumferentially outwardly directed forces on inner facing walls of ribs 949, thereby helping to retain die stone segments in tray 931 when the tray is inverted.

What is claimed is:

1. A device for detaching a break-away panel part of a dental model molding tray from a hollow body part of said tray which encloses said break-away panel, said break-away panel being located between upper and lower surfaces of said body of said molding tray and being joined by frangible members to horizontally aligned flange walls which protrude inwardly towards said panel from inner sides of a peripheral wall of said hollow tray body, said device including;

a. a template comprising a body which includes,
  (I) a base
  (ii) a peripheral flange wall which protrudes upwardly from said base,
  (iii) a recess formed between an upper surface of said base and inner surfaces of said peripheral flange wall, said recess being of a proper size and shape to vertically downwardly receive therein said hollow body of said tray, with said lower surface of said tray body parallel to and above said upper surface of said template base, and with outer upstanding surfaces of said tray perimeter wall adjacent to said inner facing upstanding surfaces of said peripheral flange wall of said template, and
  (iv) at least one rib-shaped lug which protrudes upwardly from said upper surface of said template base, said lug having a flat upper surface which is located a greater distance above said upper surface of said template base than the distance between a lower surface of said break-away panel and said lower surface of said hollow tray body, whereby said lug supports said break-away panel to thereby locate said lower surface of said hollow tray body above said upper surface of said template, and b. force exerting means for exerting a downwardly directed force on at least a first abutment flange which protrudes outwardly from said tray body relative to said template, whereby a reaction force is exerted upwardly on said break-away panel relative to said tray body sufficient to break said frangible members joining said break-away panel to said flanges, said force exerting means including a knock-out tool which has a plurality of at least three circumferentially spaced apart, downwardly protruding lower abutment flange-contacting members for contacting an upper surface of said abutment flange of said tray, and an upper anvil surface rigidly coupled to said flange-contacting members and adapted to receive a downwardly directed impact.

2. The device of claim 1 wherein said recess of said template is further defined as having in plan-view the shape of a semi-ellipse.

3. A drilling alignment fixture for facilitating drilling blind bores for the receipt of manipulating pins into bases of die segments of a dental model cast contained in a molding tray, said alignment fixture comprising an elongated body which includes;

a. a base plate which has a generally flat lower surface and a generally flat upper surface parallel to said lower surface, said upper surface having formed therein an elongated, shallow recess which is adapted to receive vertically downwardly therein a lower portion of a molding tray, with a lower surface of said tray supported on said upper surface of said base plate, b. a drill guide bushing disposed through said upper and lower surfaces of said base plate, c. indexing means for visually aligning a vertical center line of said drill guide bushing with a selected longitudinal position of a dental model casting contained in said tray, said position corresponding to a desired longitudinal location for drilling a pin bore into said dental model cast, and d. means for moving said tray horizontally on said upper surface of said base plate to thereby align said selected location of said dental model cast with said indexing means and said drill bit guide bushing.

4. The drilling alignment fixture of claim 3 wherein said indexing means for visually aligning a vertical center line of said drill bit guide bushing with a selected longitudinal position of a dental model casting in said tray is further defined as an aperture through said tray located below a void left in said cast by removal of die stone segment which is to have a pin bore drilled in the base thereof.

5. The drilling alignment fixture of claim 3 wherein said recess in said upper surface of said base plate is further defined as being a generally rectangular shaped channel which is adapted to longitudinally slidably receive a rectangular shaped dental modeling tray.

6. The drilling alignment fixture of claim 3 wherein said base plate is further defined as having a plan-view perimeter shaped generally like a semi-ellipse.

7. The drilling alignment fixture of claim 6 wherein said recess in said upper surface of said base plate is further defined as having a generally semi-elliptical plan-view shape of the proper size and shape to vertically downwardly receive therein a semi-elliptically shaped tray, with said upper surface of said base plate supporting a lower surface of said tray.

8. The drilling alignment fixture of claim 7 wherein said base plate is further defined as having through its thickness dimension a semi-elliptical sector-shaped aperture which has an outer semi-elliptically shaped wall located radially inwardly of and generally parallel to a perimeter of said base plate, and an inner semi-elliptically shaped wall located radially inwardly of and generally parallel to said outer aperture wall, said aperture orbitally holding said drill bit guide bushing.

9. The drilling alignment fixture of claim 8 further including a radially disposed arm which has an inner radial end portion pivotably fastened to a lower surface of said base plate, an outer radial portion which includes indexing means for aligning said arm with a selected circumferential portion of said perimeter wall of said base plate, and an intermediate portion which has therethrough a bore which receives therein a lower portion of said drill bit guide bushing.

10. The drilling alignment fixture of claim 7 wherein said indexing means is further defined as including a pointed end portion of said arm which is radially aligned with said center line of said drill bit guide bushing and which protrudes radially outwardly of said base plate.

11. The drilling alignment fixture of claim 10 wherein said indexing means if further defined as a gnomon which protrudes perpendicularly upwardly from said pointed end portion of said arm, in radial alignment with said center line of said drill bit guide bushing.

12. A slide receptacle for releasably holding a full-arch dental model tray and cast and attaching said receptacle to an arm of an articulator apparatus, said slide receptacle comprising;

a. a base plate, b. means for releasably attaching a dental model tray containing a dental model cast to said base plate, said means comprising in combination, (i) a horizontally disposed abutment flange which protrudes from a perimeter wall of said base plate of said tray, and (ii) means attached to said base plate for frictionally engaging said abutment flange in response to sliding lower surface of said tray on an upper surface of said base plate, c. means for releasably attaching said base plate to an arm of an articulator apparatus, said means including a ferromagnetic member recessed in a lower surface of said base plate, d. a plurality of indexing members which protrude downwardly from a lower surface of said base plate, and whereby said dental model cast tray is repeatedly fixable in a pre-determined position on said articulator arm for proper occlusal relationship of said dental model cast to an opposing arch, without requiring application of plaster or other attachment means to said tray, and whereby said tray is removable from said receptacle and connectable via hinge coupling means to comprise with an opposing dental model cast in an opposing tray an articulatable full-mouth dental model not requiring use of said articulator apparatus.

13. The slide receptacle of claim 12 wherein at least a portion of said base plate thereof is further defined as having a semi-elliptical shape.

14. The slide receptacle of claim 12 wherein said releasable attachment means is further defined as a magnetic member attachable to said arm of said articulator apparatus.

15. A method for manipulating a pair of opposed dental model casts held in separate dental model trays comprising the steps of:

a. providing a separate receptacle for each of a pair of trays holding a master dental model cast and an opposing dental model cast, b. releasably attaching each of said trays holding master and dental model casts to a separate one of said receptacles, c. releasably attaching each of said receptacles to a separate one of an upper and lower arm of a three-dimensional dental model laboratory articulator apparatus, d. effecting relative movement between said arms of said articulator to confirm proper occlusal relationship between a dental prosthesis fabricated from at least one of said dental model casts, e. removing said receptacles from said arms of said articulator, f. removing said dental model casts and prostheses from said receptacles, and g. attaching together said dental model trays holding said dental model casts and said prosthesis by a hinge coupler which enables said master and opposing dental model casts to be pivoted towards and away from one another, whereby occlusion of said dental models and prosthesis may be viewed without requiring use of said articulator.

16. The method of claim 15 wherein said receptacle slidably receives said dental model tray.

17. The method of claim 16 wherein said attaching of said receptacle to said articulator arms employs means which enable a receptacle to be repeatedly attached to and removed from said articulator arm at a precisely repeatable location.

18. The method of claim 17 wherein said means enabling repeated removal and re-attachment of said receptacle at a precisely repeatable location of said articulator arm is further defined as including magnetically attachable means on said receptacle and said articulator arm.

19. A slide receptacle for releasably holding a full-arch dental model tray and cast and attaching said receptacle to an arm of an articulator apparatus, said slide receptacle comprising;
   a. a base plate,
   b. means for releasably attaching a dental model tray containing a dental model cast to said base plate, said means comprising in combination,
      (i) a horizontally disposed abutment flange which protrudes from a perimeter wall of said base plate of said tray, and
      (ii) means attached to said base plate for frictionally engaging said abutment flange in response to sliding lower surface of said tray on an upper surface of said base plate, said means for frictionally engaging said abutment flange including a channel structure fixed to said base plate and forming therewith a channel having an opening adapted to insertably receive said abutment flange of said base plate of said tray in response to sliding said lower surface of said tray on said upper surface of said base plate, said channel structure comprising in combination a flange wall which protrudes upwardly from said upper surface of said base plate, said flange wall having a lip which protrudes inwardly from an upper edge of said flange wall towards a center of said base plate, said flange wall thereby forming with said base plate a C-shaped cross section, open channel, said channel having a transversely disposed rear opening adjacent to a transversely disposed rear edge wall of said base plate and a pair of laterally opposed side segments, said side segments having rear portions which are disposed forward of said rear transverse edge wall of said base plate, and a front abutment stop affixed to said base for limiting forward sliding motion of said base of said tray to a predetermined forward limit position,
   c. means for releasably attaching said base plate to an arm of an articulator apparatus, and
   d. whereby said dental model tray is repeatedly fixable in a pre-determined position on said articulator arm for proper occlusal relationship of said dental model cast to an opposing arch, without requiring application of plaster or other attachment means to said tray, and whereby said tray is removable from said receptacle and connectable via hinge coupling means to comprise with an opposing dental model cast in an opposing tray an articulatable full-mouth dental model not requiring use of said articulator apparatus.

20. A slide receptacle for releasably holding a full-arch dental model tray and cast and attaching said receptacle to an arm of an articulator apparatus, said slide receptacle comprising;
   a. a base plate,
   b. means for releasably attaching a dental model tray containing a dental model cast to said base plate, said means comprising in combination,
      (i) a horizontally disposed abutment flange which protrudes from a perimeter wall of said base plate of said tray, and
      (ii) means attached to said base plate for frictionally engaging said abutment flange in response to sliding lower surface of said tray on an upper surface of said base plate, said means for frictionally engaging said abutment flange including a channel structure fixed to said base plate and forming therewith a channel having an opening adapted to insertably receive said abutment flange of said base plate of said tray in response to sliding said lower surface of said tray on said upper surface of said base plate, said channel structure comprising in combination a flange wall which protrudes upwardly from said upper surface of said base plate, said flange wall having a lip which protrudes inwardly from an upper edge of said flange wall towards a center of said base plate, said flange wall thereby forming with said base plate a C-shaped cross section, open channel, said channel having a transversely disposed rear opening adjacent to a transversely disposed rear edge wall of said base plate and a pair of laterally opposed side segments, said side segments having rear portions which are disposed forward of said rear transverse edge wall of said base plate, and a front transversely disposed segment,
   c. means for releasably attaching said base plate to an arm of an articulator apparatus, and
   d. whereby said dental model tray is repeatedly fixable in a pre-determined position on said articulator arm for proper occlusal relationship of said dental model cast to an opposing arch, without requiring application of plaster or other attachment means to said tray, and whereby said tray is removable from said receptacle and connectable via hinge coupling means to comprise with an opposing dental model cast in an opposing tray an articulatable full-mouth dental model not requiring use of said articulator apparatus.

21. The slide receptacle of claim 20 wherein said front transversely disposed channel segment joins at laterally opposed outer portions thereof front portions of said laterally opposed side channel segments.

22. The slide receptacle of claim 21 wherein said front and side channel segments are joined together to form a continuous channel.

23. The slide receptacle of claim 22 wherein said channel has an arcuately curved plan-view shape.

24. The slide receptacle of claim 23 wherein said channel has a semi-oval plan-view shape.

* * * * *